(12) United States Patent
Friend et al.

(10) Patent No.: US 7,013,221 B1
(45) Date of Patent: Mar. 14, 2006

(54) ITERATIVE PROBE DESIGN AND DETAILED EXPRESSION PROFILING WITH FLEXIBLE IN-SITU SYNTHESIS ARRAYS

(75) Inventors: Stephen H. Friend, Philadelphia, PA (US); Roland Stoughton, San Diego, CA (US); Peter S. Linsley, Seattle, WA (US); Julja Burchard, Marysville, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 0 days.

(21) Appl. No.: 09/561,487

(22) Filed: Apr. 28, 2000

Related U.S. Application Data

(63) Continuation-in-part of application No. 09/364,751, filed on Jul. 30, 1999, now abandoned.

(60) Provisional application No. 60/144,382, filed on Jul. 16, 1999.

(51) Int. Cl.
*G01N 33/48* (2006.01)
*C12Q 1/68* (2006.01)

(52) U.S. Cl. ............................. 702/20; 702/19; 435/6

(58) Field of Classification Search ................ 702/19, 702/20; 435/6
See application file for complete search history.

(56) References Cited

U.S. PATENT DOCUMENTS

| | | | |
|---|---|---|---|
| 4,946,778 A | 8/1990 | Ladner et al. | |
| 5,422,242 A * | 6/1995 | Young | 435/6 |
| 5,445,934 A | 8/1995 | Fodor et al. | |
| 5,510,270 A | 4/1996 | Fodor et al. | |
| 5,539,083 A | 7/1996 | Cook et al. | |
| 5,552,270 A | 9/1996 | Khrapko et al. | |
| 5,556,749 A | 9/1996 | Mitsuhashi et al. | |
| 5,556,752 A | 9/1996 | Lockhart et al. | |
| 5,569,588 A | 10/1996 | Ashby et al. | |
| 5,578,832 A | 11/1996 | Trulson et al. | |
| 5,716,785 A | 2/1998 | van Gelder et al. | |
| 5,723,320 A | 3/1998 | Dehlinger | |
| 5,744,305 A | 4/1998 | Fodor et al. | |
| 5,817,461 A | 10/1998 | Austin et al. | |
| 5,837,832 A | 11/1998 | Chee et al. | |
| 5,856,103 A | 1/1999 | Gray et al. | |
| 5,965,352 A | 10/1999 | Stoughton et al. | |
| 6,027,890 A | 2/2000 | Ness et al. | |
| 6,040,138 A | 3/2000 | Lockhart et al. | |
| 6,110,676 A | 8/2000 | Coull et al. | |
| 6,132,969 A | 10/2000 | Stoughton | |
| 6,146,593 A | 11/2000 | Pinkel et al. | |
| 6,146,830 A | 11/2000 | Friend et al. | |
| 6,156,502 A | 12/2000 | Beattie | |
| 6,251,588 B1 * | 6/2001 | Shannon et al. ................ 435/6 |
| 6,344,316 B1 | 2/2002 | Lockhart et al. ................ 435/6 |
| 6,361,937 B1 * | 3/2002 | Stryer ............................ 435/6 |

FOREIGN PATENT DOCUMENTS

| | | |
|---|---|---|
| WO | WO 88/09810 | 12/1988 |
| WO | WO 90/11364 | 10/1990 |
| WO | WO 98/38329 | 9/1998 |
| WO | WO 98/41531 | 9/1998 |
| WO | WO 99/11820 | 3/1999 |
| WO | WO 00/43942 | 7/2000 |
| WO | WO 00/53811 | 9/2000 |

OTHER PUBLICATIONS

Altschul et al., 1997, Nucl. Acids Res. 25:3389-3402.
Altschul et al., 1990, J. Mol. Biol. 215:403-410.
Anderson et al., 1994, Adv. Immunol. 56:171-178.
Belshaw et al., 1996, Proc. Natl. Acad. Aci. USA 93:4604-4607.
Bernoist and Chambon, 1981, Nature 290:304-310.
Biocca and Cattanco, 1995, Trends Cell Biol. 5:248-252.
Blanchard et al., 1996, Nat. Biotech. 14:1649.
Blanchard et al., 1996, Biosensors and Bioelectronics 11: 687-690.
Blanchard, 1998, *Synthetic DNA Arrays in Genetic Engineering* (Plenum Press, New York) vol. 20 pp. 111-123.
Boguski and Schuler, 1995, Nat. Gen. 10:369-371.
Bradbury et al., 1995, *Antibody Engineering* (IRL Press) vol. 2 pp. 295-361.

(Continued)

*Primary Examiner*—Marianne P. Allen
(74) *Attorney, Agent, or Firm*—Jones Day

(57) ABSTRACT

Methods and compositions are provided that are useful for detecting and reporting a plurality of different target polynucleotide sequences in a sample, such as polynucleotides corresponding to a plurality of different genes expressed by a cell or cells. In particular, the invention provides methods for screening a plurality of candidate polynucleotide probes to evaluate both the sensitivity and the specificity with which each candidate probe hybridizes to a target polynucleoide sequence. Candidate polynucleotide probes can then be ranked according to both their sensitivity and specificity, and probes that have optimal sensitivity and specificity for a target polynucleotide sequence can be selected. In one embodiment, polynucleotide probes can be selected according to the methods described herein to prepare "screening chips" wherein a large number of target polynucleotide sequences are detected using a single microarray have a few (e.g., 1–5) probes for each target polynucleotide sequence. In a particularly preferred embodiment, the invention provides a screening chip that can detect genetic transcripts from the entire genome of an organism. In an alternative embodiment, polynucleotide probes can be selected according to the methods described herein to prepare "signature chips" to more accurately detect certain selected "signature genes" using several polynucleotide probes (e.g., 10–20) for each signature gene. The invention additionally provides microarrays containing polynucleotide probes for a large number of genes expressed by a cell or organism. Further, methods for detecting a plurality of polynucleotide molecules, including a large number of genes expressed by a cell or organism, are also provided.

90 Claims, 24 Drawing Sheets

OTHER PUBLICATIONS

Brinster et al., 1982, Nature 296:39-42.
Burke et al., 1984, Cell 36:847-858.
Bussey et al., 1995, Proc. Natl. Acad. Sci. USA 92:3809-3813.
Cech et al., 1987, Science 236:1532-1539.
Chetverin and Kramer, 1994, Bio/Technology 12:1093-1099.
Chirgwin et al., 1979, Biochem. 18:5294-5299.
Claverie, 1996, Meth. Enzymol. 266:212-227.
Cole et al., 1985, *Monoclonal Antibodies and Cancer Therapy* (Alan R. Liss, Inc.) Pp. 77-96.
Cotten and Birnstiel, 1989, EMBO J. 8:3861-3866.
DeRisi et al., 1996, Nat. Gen. 14:457-460.
Dohmen et al., 1994, Science 263:1273-1276.
Dujon et al., 1994, Nature 369:371-378.
Egholm et al., 1993, Nature 363:566-568.
Feldman et al., 1994, EMBO J. 13:5795-5809.
Ferguson et al., 1996, Nat. Biotech. 14:1681-1684.
Fodor et al., 1991, Science 251:767-773.
Froehler et al., 1986, Nucl. Acids Res. 14:5399-5407.
Galibert et al., 1996, EMBO J. 15:2031-2049.
Gari et al., 1997, Yeast 13:837-848.
Gautier et al., 1987, Nucl. Acids Res. 15:6625-6641.
Gibson, 1996, Cancer and Metastasis Rev. 15:287-299.
Goffeau et al., 1996, Science 274:546-567.
Good et al., 1997, Gene Ther. 4:45-54.
Gossen et al., 1995, Proc. Natl. Acad. Sci. USA 89:5547-5551.
Grassi and Marini, 1996, Ann. Med. 28:499-510.
Griffiths et al., 1994, EMBO J. 13:3245-3260.
Guo, 1996, Dissertation, University of Wisconsin.
Haseloff and Gerlach, 1988, Nature 334:585-591.
Hayden et al., 1997, Curr. Opin. Immunol. 9:210-212.
Hershkowitz, 1987, Nature 329:219-222.
Hoffman et al., 1996, Proc. Natl. Acad. Sci. USA 83:5185-5190.
Hoffman et al., 1997, Nucl. Acids. Res. 25:1078-1079.
Huse et al., 1989, Science 246:1275-1281.
Hyndman et al., 1996, Biotechniques 20:1090-1096.
Inoue et al., 1987, FEBS Lett. 215:327-330.
Inoue et al., 1987, Nucl. Acids Res. 15:6131-6148.
Johnston et al., 1994, Science 265:2077-2082.
Johnston et al., 1984, Mol. Cell. Biol. 4:1440-1448.
Kerjan et al., 1986, Nucl. Acids Res. 14:7861-7871.
Khrapko et al., 1991, J. DNA Sequencing and Mapping 1:375-388.
Khrapko et al. 1991, Molecular Biology 25:581-591.
Ko et al., 1993, Mol. Cell. Biol. 13:638-648.
Kohler and Milstein, 1975, Nature 256:495-497.
Koizumi et al., 1988, FEBS Lett. 228:228-230.
Koizumi et al., 1988, FEBS Lett. 239:285-288.
Kozbor and Roder, 1983, Immunol. Today 4:72.
Lemaitre et al., 1989, Proc. Natl. Acad. Sci. USA 84:648-652.
Lockhart et al., 1996, Nat. Biotech. 14:1675-1680.
Lodish et al., 1995, *Molecular Biology of the Cell* (W.H. Freeman and Co., New York) Chapter 8.
Marks et al., 1992, J. Biol. Chem. 267:16007-16010.
Mascorro-Gallardo et al., 1996, Gene 172:169-170.
Maskos and Southern, 1992, Nucl. Acids Res. 20:1679-1684.
McBride and Caruthers, 1983, Tertahedron Lett. 24:245-248.
Miyoshi et al., 1995, Nucl. Acids Res. 23:2762-2769.
Morgan et al., 1988, Immunol. Today 9:84-86.
Morrison et al., 1984, Proc. Natl. Acad. Sci. USA 81:6851-6855.
Mumberg et al., 1994, Nucl. Acids Res. 22:5767-5768.
Neuberger et al., 1984, Nature 312-:604-608.
Nguyen et al., 1995, Genomics 29:207-216.
No et al., 1996, Proc. Natl. Acad. Sci. USA 93:3346-3351.
Nocka et al., 1990, EMBO J. 9:1805-1813.
Paulus et al., 1996, J. Virol. 70:62-67.
Pease et al., 1994, Proc. Natl. Acad. Sci. USA 91:5022-5026.
Perlmutter and Alberola, 1996, Curr. Opin. Immunol. 8:285-290.
Pettitt et al., 1996, Dev. 122:4149-4157.
Press et al., 1992, "Solution of Linear Algebraic Equations" *Numerical Recipes in C* (Cambridge University Press) Chapter 2.
Ramirez-Solis et al., 1993, Meth. Enzymol. 225:855-878.
Ray et al., 1997, Proc. Natl. Acad. Sci. USA 94:3229-3234.
Santa Lucia, 1998, Proc. Natl. Acad. Sci. USA 95:1460-1465.
Sarin et al., 1988, Proc. Natl. Acad. Sci. USA 85:7448-7451.
Sarver et al., 1990, Science 247:1222-1225.
Schena et al., 1996, Proc. Natl. Acad. Sci. USA 93:10614.
Schena et al., 1995, Science 270:467-470.
Schuler, 1997, J. Mol. Med. 75:694-698.
Schuler et al., 1996, Science 274:540-546.
Shalon et al., 1996, Genome Res. 6:639-645.
Shimizu et al., 1992, J. Biochem. 111:272-277.
Southern et al., 1992, Genomics 13:1008-1017.
Southern et al., 1994, Nucl. Acids. Res. 22:1368-1373.
Spencer, 1996, Trends Gen. 12:181-187.
Spradling et al., 1995, Proc. Natl. Acad. Sci. USA 92:10824-10830.
Stein et al., 1988, Nucl. Acids Res. 16:3209.
Straus and Weiss, 1992, Cell 70:585-593.
Takeda et al., 1985, Nature 314:452-454.
Thomas and Capecchi, 1987, Cell 51:503-512.
van der Krol et al., 1988, BioTechniques 6:958-976.
Wagner et al., 1981, Proc. Natl. Acad. Sci. USA 78:1441-1445.
Yamamoto et al., 1980, Cell 22:787-797.
Zhang and Madden, 1997, Genome Res. 7:649-656.
Zon, 1988, Pharm. Res. 5:539-549.
Lipshutz et al., 1999, Nature Genetics Supplement 21:20-24.
Khrapko, 1999, "Harvard Nathan Shock Center: High Throughput Technology Core" http://www.hms.harvard.edu/aging/nathan/high.html.
Khrapko et al., 1999, Poster Abstract, Chips to Hits '99 Conference, Nov. 2-5, 1999.
MaGall et al., 1996, Proc. Natl. Acad. Sci. USA 93:13555-13560.

* cited by examiner

ITERATIVE PROBE DESIGN AND DETAILED EXPRESSION PROFILING WITH FLEXIBLE IN-SITU SYNTHESIS ARRAYS

This is a continuation-in-part application of U.S. patent application Ser. No. 09/364,751, filed on Jul. 30, 1999, now abandoned which claims benefit under 35 U.S.C. § 119(e) of now abandoned U.S. Provisional Patent Application Ser. No. 60/144,382, filed on Jul. 16, 1999, each of which is incorporated herein by reference in its entirety.

1. FIELD OF THE INVENTION

The field of this invention relates to materials and methods to detect and report polynucleotide sequences, including genomic sequences, genomic transcript sequences (e.g., mRNAs from cells and/or cDNA sequences derived therefrom), copy numbers and SNPs. In particular, the invention relates to methods for detecting polynucleotide sequences using sets of polynucleotide probes that have been selected for optimum sensitivity and specificity. The invention also relates to methods for selecting sets of polynucleotide probes for optimum sensitivity and specificity which may be used, e.g., to detect and report gene expression changes in a cell or cells. The invention further relates to sets of polynucleotide probes, including microarrays comprising such sets of polynucleotide probes, which are selected for optimum sensitivity and specificity and are therefore useful, e.g., to detect and report gene expression changes in a cell or cells.

2. BACKGROUND

Within the past decade, several technologies have made it possible to monitor the expression level of a large number of genetic transcripts at any one time (see, e.g., Schena et al., 1995, *Science* 270:467–470; Lockhart et al., 1996, *Nature Biotechnology* 14:1675–1680; Blanchard et al., 1996, *Nature Biotechnology* 14:1649; Ashby et al., U.S. Pat. No. 5,569,588, issued Oct. 29, 1996). For example, techniques are known for preparing microarrys of cDNA transcripts (see, e.g., DeRisi et al., 1996, *Nature Genetics* 14:457–460; Shalon et al., 1996, *Genome Res.* 6:689–645; and Schena et al., 1995, *Proc. Natl. Acad. Sci. U.S.A.* 93:10539–11286). Alternatively, high-density arrays containing thousand of oligonucleotides complementary to defined sequences, at defined locations on a surface using photolithographic techniques for synthesis in situ are described, e.g., Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270). Methods for generating arrays using inkjet technology for oligonucleotide synthesis are also known in the art (see, e.g., Blanchard, International Patent Publication WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123).

Applications of this technology include, for example, identification of genes which are up regulated or down regulated in various physiological states, particularly diseased states. Additional exemplary uses for transcript arrays include the analyses of members of signaling pathways, and the identification of targets for various drugs. See, e.g. Friend and Hartwell, International Publication No. WO 98/38329 (published Sep. 3, 1998); Stoughton, U.S. patent application Ser. No. 09/099,722 (filed Jun. 19, 1998); Stoughton and Friend, U.S. patent application Ser. No. 09/074,983 (filed May 8, 1998); Friend and Stoughton, U.S. Provisional Application Ser. Nos. 60/084,742 (filed May 8, 1998), 60/090,004 (filed Jun. 19, 1998), and 60/090,046 (filed Jun. 19, 1998).

However, several factors limit the number of genetic transcripts that can be detected on a single microarray "chip." In particular, the "reporting density" (i.e., the number of genes detected per unit of surface area) for a microarray is limited, e.g., by the density with which polynucleotide probes may be laid down as well as by the number of polynucleotide probes required per gene. A plurality of probe pairs, which are both matched to and intentionally mismatched to a target sequence, are required in order to empirically distinguish signal arising from a target polynucleotide sequence of interest (e.g., a particular mRNA sequence of interest) from signal arising from cross-hybridization with other polynucleotide sequences. Currently, in situ synthesized microarray chips require more than 20 oligonucleotide probe pairs per gene or gene region reported (Lockhart et al., supra). On the other hand, the number of polynucleotide probes that may be laid down on a microarray chip is limited by the technology used to produce the microarray. Photolithographic techniques discussed above for producing oligonucleotide microarrays having a high spatial density of probes are expensive to synthesize and therefore require a large capital investment. Oligonucleotide microarrays produced using the above discussed inkjet technology methods are, by contrast, much cheaper and faster to produce both per chip design and per chip. Thus, such microarrays are generally preferred for detecting genetic transcripts in cells. However, microarray chips produced by such inkjet technology have a limited probe density that is only a fraction of the probe density of chips produced by photolithography methods. Thus, at present the number of genetic transcripts that may be detected on a single microarray chip is limited to about 10,000 gene transcripts using expensive, photolithographic arrays, and only about 750 to 2,500 gene transcripts using less expensive, inkjet arrays.

There exists therefore a need for materials and methods which may be used to efficiently detect large numbers of different genetic transcripts and thereby detect changes in a large number of genetic transcripts in a cell or cells. In particular, there is a need for materials and methods which may be used to detect changes in genetic transcription across the entire genome of a cell, including cells of complex organisms such as mammalian cells and, in particular, human cells.

There also exists, however, a need for materials and methods which may be used to accurately detect charges in genetic transcripts in cells, e.g., in response to some environmental change or perturbation. In particular, there is a need to accurately detect changes in the expression levels of those particular genetic transcripts that exhibit the largest changes, e.g., in response to an environmental change or perturbation, and which are therefore most relevant in understanding the effect of the environmental change or perturbation on the cell or cells.

Discussion or citation of a reference herein shall not be construed as an admission that such reference is prior art to the present invention.

3. SUMMARY OF THE INVENTION

The present invention provides methods and compositions that efficiently detect and accurately report gene expression changes in an organism. In particular, the methods and compositions of the invention may be used to detect and report gene expression changes in a cell or organism that occur, e.g., in response to some change or "perturbation" to the cell or organism and/or to its environment, such as exposure of the cell or organism to one or more drugs.

The compositions and methods of the invention use "screening chips," which may be used, e.g., to detect changes in gene expression among a large number of genes or gene transcripts. For example, in particularly preferred embodiments, the screening chips may be used to detect changes in gene expression in the entire genome of an organism. Such screening chips are therefore provided as part of the present invention, as well as methods for making and using such screening chips, e.g., to screen the entire genome of an organism for changes in response to one or more perturbations.

The compositions and methods of the invention also provide "signature chips" which may be used to accurately detect changes in gene expression in a smaller number of genes. For example, the signature chips of the invention may be used to accurately detect changes in the expression of certain "signature genes." In preferred embodiments, the signature genes are those genes whose expression changes the most in response to a particular perturbation or in response to a particular type or set of perturbations (e.g., responses to several doses of a drug or responses to several different, but related drugs). For example, signature genes may be identified using the screening chips of the invention to identify those genes whose expression changes the most in response to a particular perturbation or perturbations. In one preferred embodiment, the signature chips of the invention comprise at least a first probe and a second probe for each signature gene to be detected, wherein the first probe for a particular signature gene is a matched probe having a polynucleotide sequence that is complementary to the particular signature gene or to a portion thereof, and wherein the second probe for a particular signature gene is a mismatch probe having a polynucleotide sequence that is a variant of a sequence which is complementary to the particular signature gene. In another preferred embodiment the signature chips of the invention comprise a plurality of matched probes for each signature gene to be detected, wherein each matched probe for a particular signature gene has a polynucleotide sequence that is complementary to the particular signature gene or to a portion thereof.

The invention also provides methods and compositions for ranking and/or selecting probes according to other parameters including, but not limited to: (a) probe size or length; (b) binding energies, including both the perfect match duplex (i.e., of a probe and its target, complementary nucleotide sequence) and cross-hybridization binding energies; (c) base composition, including, for example, the relative amount or percentage of one or more particular nucleotide bases (e.g., adenine, guanine, thymine or cytosine) in a probe sequence, as well as the relative amount or percentage of any combination of such nucleotide bases; (d) the position of a probe's complementary sequence in the sequence of its "target" polynucleotide or gene sequence; and (e) probe sequence complexity, including the presence or lack of common repetitive elements such as polynucleotide repeats (i.e., simple, contiguous repeats of one or more nucleotide bases) as well as more complicated repetitive elements that are well known in the art. Still other exemplary parameters which can be used in the methods and compositions of the invention for ranking and/or selecting oligonucleotide probes include: (f) self dimer binding energy (i.e., the tendency for a particular probe to hybridize to its own sequence); (g) the structure content of the complementary, target polynucleotide sequence for a particular probe (e.g., the presence or absence of certain structural features or motifs); and (h) the information content of a probe's nucleotide sequence.

The invention is based, at least in part, on the discovery that the number of probe sequences required to reliably and accurately report a particular polynucleotide sequence, such as the sequence of a particular gene, may be reduced to as few as one probe by carefully selecting probes according to the methods and/or having the particular lengths disclosed herein. Accordingly, the invention also provides methods by which probes (i.e., probe sequences) may be ranked and/or selected according to their reporting properties, including, for example, their specificity and sensitivity for a particular sequence (e.g., for the sequence of a particular gene or gene transcript).

The invention thus provides methods for selecting one or more different polynucleotide probes from a plurality of polynucleotide probes according to the sensitivity and specificity with which each different polynucleotide probe hybridizes to a target polynucleotide. In one embodiment, the methods comprise: (a) identifying polynucleotide probes in the plurality of different polynucleotide probes that hybridize to the target polynucleotide with a sensitivity above a threshold sensitivity level; (b) ranking the identified polynucleotide probes according to the specificity with which each identified polynucleotide probe hybridizes to the target polynucleotide; and (c) selecting one or more different polynucleotide probes from the ranked polynucleotide probes. In another embodiment, the methods comprise: (a) identifying polynucleotide probes in the plurality of different polynucleotide probes that hybridize to the target polynucleotide with a specificity above a threshold specificity level; (b) ranking the identified polynucleotide probes according to the sensitivity with which each identified polynucleotide probe hybridizes to the target polynucleotide; and (c) selecting one or more different polynucleotide probes from the ranked polynucleotide probes. In still another embodiment, the methods comprise: (a) ranking the plurality of different polynucleotide probes according to the sensitivity with which each polynucleotide probe hybridizes to the target polynucleotide so that a sensitivity rank is obtained for each different polynucleotide probe; (b) ranking the plurality of different polynucleotide probes according to the specificity with which each polynucleotide probe hybridizes to the target polynucleotide so that a specificity rank is obtained for each different polynucleotide probe; (c) obtaining a combined rank for each different polynucleotide probe, wherein the combined rank is determined by determining the sum of the sensitivity rank and the specificity rank for each different polynucleotide probe; and (d) selecting one or more different polynucleotide probes from the plurality of different polynucleotide probes according to the combined rank of the different polynucleotide probes. In one aspect of this particular embodiment, the sum of the sensitivity rank and the specificity rank for each different polynucleotide probe can be, e.g., a weighted sum of the sensitivity rank and the specificity rank for each different polynucleotide probe.

The invention provides numerous different aspects of these different embodiments, for example, the invention provides aspects of the above embodiments wherein the sensitivity with which a particular polynucleotide probe hybridizes to the target is provided by determining the binding energy with which the target polynucleotide hybridizes to the particular polynucleotide probe, e.g., according to the nearest neighbor model. The invention also provides aspects of the above embodiments wherein the sensitivity with which a particular polynucleotide probe hybridizes to the target polynucleotide is provided by a method comprising determining the level of hybridization of the target polynucleotide sequence to the particular polynucleotide probe; e.g., by calculating the level of hybridization of the target polynucleotide to the polynucleotide probe from the binding energy with which the target polynucleotide hybridizes to the particular polynucleotide probe.

In another aspect of the methods of the invention, the specificity with which a particular polynucleotide probe hybridizes to the target polynucleotide is provided, e.g., by: (a) determining the level of hybridization of the target polynucleotide to the particular polynucleotide probe; and (b) determining the level of cross-hybridization of non-target polynucleotides to the particular probe.

In still other embodiments, the methods of the invention comprise: (a) hybridizing a reference polynucleotide sample comprising molecules of the target polynucleotide to the plurality of different polynucleotide probes under conditions such that the hybridization intensity of each different polynucleotide probe to the reference sample correlates with the sensitivity and specificity with which the each different polynucleotide probe hybridizes to the target polynucleotide; and (b) selecting polynucleotide probes in the plurality of different polynucleotide probes that have the highest hybridization intensity. For example, the invention provides particular aspects of this embodiment wherein the hybridization is within 5° C. or within 2° C. of the mean melting temperature of the plurality of different polynucleotide probes from the target polynucleotide.

The invention also provides a preferred embodiment wherein the specificity of a particular polynucleotide probe is provided by a method which comprises selecting, from a plurality of binding energies, a binding energy that indicates the specificity of the particular polynucleotide probe. Specifically, in such a preferred embodiment, the provided plurality of binding energies are binding energies for hybridization of the particular polynucleotide probe to each of a plurality of different polynucleotides, wherein each polynucleotide in the plurality of different polynucleotides is different from the target polynucleotide. The selected binding energy is the largest binding energy in the plurality of binding energies.

For example, in one aspect of this preferred embodiment, the binding energies provided for hybridization of the particular polynucleotide probe to each of the plurality of polynucleotides is provided according to a nearest neighbor model. In one aspect the plurality of polynucleotides comprise polynucleotides expressed by a cell or organism of interest. In one aspect, the plurality of polynucleotides consists of polynucleotides having sequences with a selected level of identity or homology to a complementary sequence of the particular polynucleotide probe. For example, in one aspect, the sequences having the selected level of identity or homology to the complementary sequence of the probe are identified by means of a BLAST or PowerBLAST algorithm. In various aspects, the plurality of polynucleotides consists of polynucleotides having sequences that are at least 50%, at least 60%, at least 70%, at least 80%, at least 90%, at least 95% or at least 99% identical to the complementary sequence of the particular polynucleotide probe.

In still other embodiments, which are both more general and more preferred embodiments, the polynucleotide or oligonucleotide probes are ranked and/or selected according to a combination of two or more of the properties (a)–(h) listed above and, optionally, the sensitivity and/or specificity with which each probe hybridizes to a target polynucleotide. For example, in one embodiment the invention provides methods for selecting one or more different polynucleotide probes from a plurality of polynucleotide probes be a method comprising: (a) identifying those polynucleotide probes in the plurality of polynucleotide probes that have particular values (or a particular range of values) of one, two, three or more properties or parameters (e.g., selected among the properties and parameters listed hereinabove); and (b) selecting the polynucleotide probes identified in step (a).

In another general embodiment, the methods of the invention comprise: (a) ranking the polynucleotide probes in a plurality of different polynucleotide probes according to each of two or more selected properties or parameters (e.g., selected from the properties and parameters recited hereinabove) so that a rank is obtained for each of the two or more selected parameters; and (b) obtaining a combined rank for each different polynucleotide probe, wherein the combined rank is determined from the sum of the ranks obtained for each of the two or more selected properties or parameters. One or more different polynucleotide probes can then be selected from the plurality of different polynucleotide probes according to the combined rank of the different polynucleotide probes.

In yet another general embodiment, the methods of the invention comprise: (a) identifying those polynucleotide probes in the plurality of polynucleotide probes that have particular values (or a particular range of values) of one, two, three or more properties or parameters (e.g., selected among the properties and parameters listed hereinabove); (b) ranking the identified polynucleotide probes according to each of two or more selected properties or parameters (e.g., selected among the properties and parameters listed hereinabove) so that a rank is obtained for each of the two or more selected parameters; and (c) obtaining a combined rank for each identified polynucleotide probe, wherein the combined rank is determined from the sum of the ranks obtained for each of the two or more selected properties or parameters. One or more different polynucleotide probes can then be selected from the identified polynucleotide probes according to the combined rank of the identified polynucleotide probes.

In such a general embodiment, the properties or parameters used to rank the identified probes in step (b) can be either the same as or, more preferably, different from the properties or parameters used to identify those polynucleotide probes in step (a). Also, in certain aspects of embodiments such as the general embodiments described above, the sum of the ranks obtained for each of the two or more selected properties or parameters can be, e.g., a weighted sum of the ranks obtained for each of the two or more selected properties or parameters.

The invention provides certain preferred aspects of the above methods wherein the steps of the methods are iteratively repeated, e.g., to select no more than 20, 10, 5 or 1 different polynucleotide probe or probes. The invention also provides preferred aspects of these methods wherein the polynucleotide probes comprise polynucleotide sequences that are, e.g., between 15–500, 20–100 or 40–60 bases in length.

The invention also provides, in still other embodiments, screening chips and signature chips that comprise arrays of polynucleotide probes selected according to the methods of the invention. Specifically, the screening chips of the invention comprise an array of a plurality of different polynucleotide probes for a plurality of different target polynucleotides, wherein each different polynucleotide probe in the plurality of different polynucleotide probes is selected by any one of the above described methods. In preferred embodiments, the screening chips comprise, e.g., at least 4000, 10000, 15000, 20000, 80000, or 100000 different polynucleotide sequences. In other preferred embodiments, the screening chips of the invention comprise no more than 10, 2 or 1 different polynucleotide probes that hybridize to a particular target polynucleotide.

In yet other embodiments, the screening chips comprise an array of a plurality of different polynucleotide probes for a plurality of different target polynucleotides, wherein each different polynucleotide probe is selected according to any one of the methods of the invention and wherein the plurality of different target polynucleotides comprise polynucleotide sequences of, e.g., at least 50%, 75%, 80%, 85%, 90%, 95%, 99% or 100% (i.e., all) of the genes in the genome of a cell or organism; including particular embodiments wherein the cell or organism is a human cell or organism.

The signature chips of the invention comprise an array of a plurality of different polynucleotide probes for one or more target polynucleotides, wherein each different polynucleotide probe is selected by one of the methods of the invention. In preferred embodiments, the target polynucleotides comprise one or more signature genes which comprise one or more genetic transcripts of a cell or organism whose abundances change in response to one or more changes or perturbations to the cell or organism.

In one preferred embodiment, the signature chips of the invention comprise, for each target polynucleotide, at least one pair of polynucleotide probes wherein each pair comprises: (a) a match probe that is complementary to a particular target polynucleotide; and (b) an intentional mismatch probe that differs from the match probe in at least one nucleotide. In another preferred embodiment, the signature chips of the invention comprise, for each target polynucleotide, at least one set of polynucleotide probes, with each set comprising: (a) a match probe that is complementary to a particular target polynucleotide; and (b) a plurality of (for example between 4 and 20) different intentional mismatch probes which differ from the match probe in at least one nucleotide.

The invention also provides, in still other embodiments, methods for preparing signature chips comprising an array of polynucleotide probes for one or more signature genes, wherein the methods comprise: (a) identifying one or more target polynucleotides corresponding to gene transcripts of a cell or organism that change expression or abundances in response to one or more particular changes or perturbations to the cell or organism, said one or more target polynucleotides being said one or more signature genes; (b) selecting a plurality of different polynucleotide probes for each of said one or more signature genes from a plurality of candidate polynucleotide probes according to the sensitivity and specificity with which each candidate polynucleotide probe hybridizes to one of said signature genes; and (c) preparing a microarray comprising an array of the selected polynucleotide probes for each of said one or more signature genes, wherein said microarray is a signature chip. In one preferred aspect of this embodiment, the one or more particular target polynucleotides are identified using a screening chip, wherein the screening chip comprises an array of different polynucleotide probes for a plurality of different target polynucleotides, and wherein each different polynucleotide probe of said screening chip is selected according to the sensitivity and specificity with which each different polynucleotide probe hybridizes to one of said plurality of target polynucleotides.

In yet other embodiments, the invention further provides arrays of polynucleotide probes. The arrays comprise a support with at least one surface and at least 100 different polynucleotide probes, each different polynucleotide probes comprising a different polynucleotide sequence and being attached to the surface of the support in a different location on the surface. The nucleotide sequence of the different polynucleotide probes is in the range of 40 to 80 nucleotides in length, and in preferred embodiments is in the range of 50 to 70, or 50 to 60 nucleotides in length. In preferred aspects of this embodiment, the arrays comprise polynucleotide probes of at least 4000, 10000, 15000, 20000, 50000, 80000, or 100000 different nucleotide sequences. Preferably, each polynucleotide probe on the array is specific for a particular target polynucleotide sequence. More preferably, the nucleotide sequence of each different polynucleotide probe of the array is specific for a different target polynucleotide sequence. Preferably, the target polynucleotide sequences comprise expressed polynucleotide sequences of a cell or organism, such as a mammalian cell or organism (e.g., a human cell or organism), and the nucleotide sequences of the different probes of the array are specific for at least 50%, 75%, 80%, 85%, 90%, 95%, 99% or 100% (i.e., all) of the genes in the genome of the cell or organism.

In still other preferred embodiments, the arrays comprise at least 100, at least 1000, or at least 2500 different probes per 1 $cm^2$. In other preferred embodiments the array is a positionally addressable array. In yet other preferred embodiments, the different polynucleotide probes comprise sets of polynucleotide probes, each set of polynucleotide probes comprising: (a) a match probe having a nucleotide sequence that is complementary to a particular target polynucleotide sequence, and (b) at least one intentional mismatch probe having a nucleotide sequence which differs from the nucleotide sequence of the match probe in at least one nucleotide, and more preferably in one to three nucleotides.

The invention still further provides, in other embodiments, systems (e.g., computer systems) for executing the methods of the invention. In particular, a computer system of the invention comprises a memory and a processor interconnected with the memory, wherein the memory encodes one or more programs causing the processor to perform one or more of the above-related methods. The invention also provides computer program products for using in conjunction with a computer having a memory and a processor. The computer program products of the invention comprise a computer readable storage medium having a computer program mechanism encoded thereon, wherein the computer program mechanism may be loaded into the memory of a computer and causes a processor of the computer to execute the steps of one or more of the above-recited methods.

In addition, the present invention also provides methods for detecting whether a plurality of polynucleotide molecules is present in a sample. Such methods comprise steps of: (a) contacting a sample comprising polynucleotide molecules to an array of the invention under conditions that permit the polynucleotide molecules in the sample to hybridize to the array; and (b) detecting any hybridization of polynucleotide molecules in the sample to polynucleotide probes of the array. Hybridization of a particular polynucleotide molecules to a polynucleotide probe of the array then indicates the presence of that particular polynucleotide molecule in the sample. In particularly preferred aspects of this embodiment, the methods are used to detect polynucleotides expressed by a cell or organism (e.g., expressed by at least 50%, 75%, 85%, 90%, 95% or 99% of the expressed genes in the genome of the cell or organism). In particular, in such preferred aspects the sample comprises polynucleotide molecules, such as mRNA molecules, expressed by the cell or organism, or polynucleotide molecules such as cDNA molecules or cRNA molecules that are derived therefrom.

It yet another embodiment, the invention also provides methods for detecting whether a plurality of polynucleotide molecules is present in a sample. The methods comprise: (a) contacting a sample comprise polynucleotide molecules to an array under conditions that permit polynucleotide molecules in said sample to hybridize to polynucleotide probes of said array; and (b) detecting any hybridization of polynucleotide molecules in the sample to polynucleotide probes of the array. Hybridization of a particular polynucleotide molecule to a polynucleotide probe of the array indicates the presence of the particular polynucleotide molecule in the sample. In preferred aspects of this embodiment, the array comprises a support with at least one surface and having at least 100 different polynucleotide probes. Each different polynucleotide probe: (i) comprises a different nucleotide sequence, (ii) is attached to the surface of the support at a different location on the surface, and (iii) has a nucleotide sequence 40 to 80 nucleotides in length.

4. BRIEF DESCRIPTION OF THE DRAWINGS

FIG. 1 provides a flow chart illustrating an exemplary embodiment of the general methods of the present invention.

FIG. 2 depicts the predicted "melting curve," i.e., the fraction of target polynucleotide molecules bound to an oligonucleotide probe as a function of the hybridization temperature, for perfect match polynucleotide molecules (PM), one base mismatch polynucleotide molecules (1MM), and two base mismatch polynucleotide molecules (2MM); also depicted as a function of temperature are the hybridization ratios of perfect match polynucleotide molecules to 1 base mismatch polynucleotide molecules (Ratio PM/1MM) and of perfect match polynucleotide molecules to 2 base mismatch polynucleotide molecules (Ratio PM/2MM).

FIGS. 3A–D show experimental data demonstrating that hybridization specificity of a collection of probes is optimized at or slightly above the mean melting temperature of the probes; specifically FIG. 3A shows the mean hybridization intensity ratio of perfect-match to single mismatch (PM/SM, ———) and perfect-match to double mismatch (PM/DM, ----) vs. the hybridization temperature observed for a collection of 22-mer oligonucleotide probes; FIG. 3B is a histogram showing the distribution of perfect match melting temperatures ($T_m$) predicted for the 22-mer probes; FIG. 3C shows the mean hybridization intensity ratio of perfect-match to single mismatch (PM/SM, ———) and perfect-match to double mismatch (PM/DM, ----) vs. the hybridization temperature observed for a collection of 35-mer oligonucleotide probes; FIG. 3D is a histogram showing the distribution of perfect match melting temperatures ($T_m$) predicted for the 35-mer probes.

FIG. 4 plots the schematic behavior of the intensity and specificity of hybridization for polynucleotide probes as a function of their binding energies $\Delta G$.

FIGS. 5A–C show the amount of target and non-targeted hybridization observed for individual probes targeted for the S. cerevisiae gene YER019W, individual probes are identified according to their "tiling position"; FIG. 5A plots the mean normalized hybridization intensity for a polynucleotide sample which contains only YER019W polynucleotides ("targeted hybridization"); FIG. 5B plots the mean normalized hybridization intensity for a polynucleotide sample derived from an S. cerevisiae strain deleted for the gene YER019W ("non-targeted hybridization"); FIG. 5C plots the ratio of targeted to non-targeted hybridization intensities shown in FIGS. 5A–B; those probes which are predicted to have the highest specificity are marked with an (X) symbol.

FIGS. 6A–C show the amount of target and non-targeted hybridization observed for individual probes targeted for the S. cerevisiae gene HXT3, individual probes are identified according to their "tiling position"; FIG. 6A plots the mean normalized hybridization intensity for a polynucleotide sample which contains only HXT3 polynucleotides ("targeted hybridization"); FIG. 6B plots the mean normalized hybridization intensity for a polynucleotide sample derived from an S. cerevisiae strain deleted for the gene HXT3 ("non-targeted hybridization"); FIG. 6C plots the ratio of targeted to non-targeted hybridization intensities shown in FIGS. 6A–B; those probes which are predicted to have the highest specificity are marked with an (X) symbol.

FIGS. 7A–B show plots of binding energy and specificity for a plurality of oligonucleotide probes to the S. cerevisiae genes YER019W and YAR010C using binding energy and specificity values calculated according to the methods described hereinbelow; FIG. 7A is a plot of the energy score (i.e., the binding energy) vs. the cross-hybridization score (i.e., the specificity) of probes to the gene YER019W; FIG. 7B is a plot of the energy score (i.e., the binding energy) vs. the cross-hybridization score (i.e., the specificity) of probes to the gene YAR010C.

FIGS. 8A–B show plots of hybridization intensity vs. specificity for a plurality of oligonucleotide probes to the S. cerevisiae genes YER019W and HXT3, using the experimental data displayed in FIGS. 5 and 6; FIG. 8A plots the observed hybridization intensities vs. specificity for oligonucleotide probes to the gene YER019W; FIG. 8B plots the observed hybridization intensities vs. specificity for oligonucleotide probes to the gene HXT3.

Figure 14A:
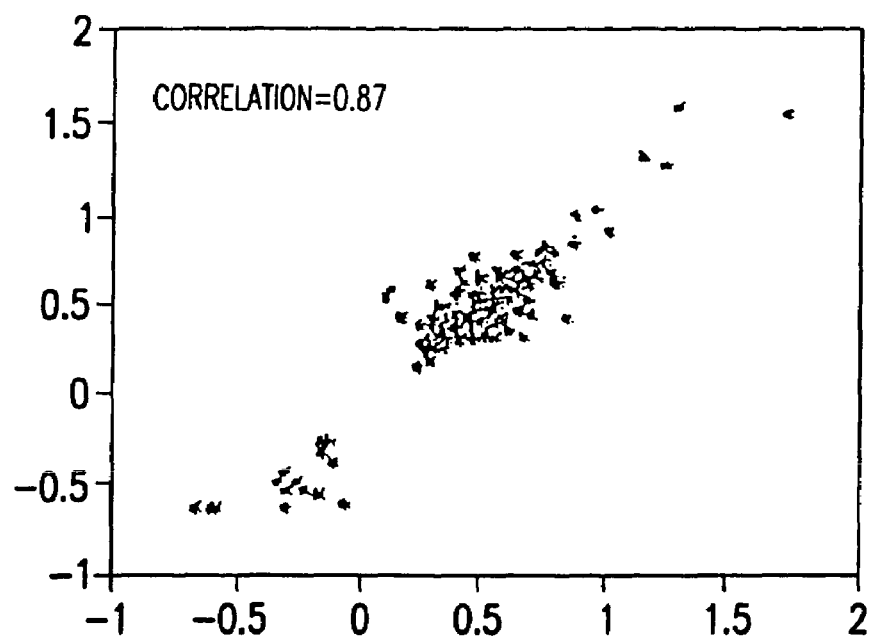
Figure 14B:
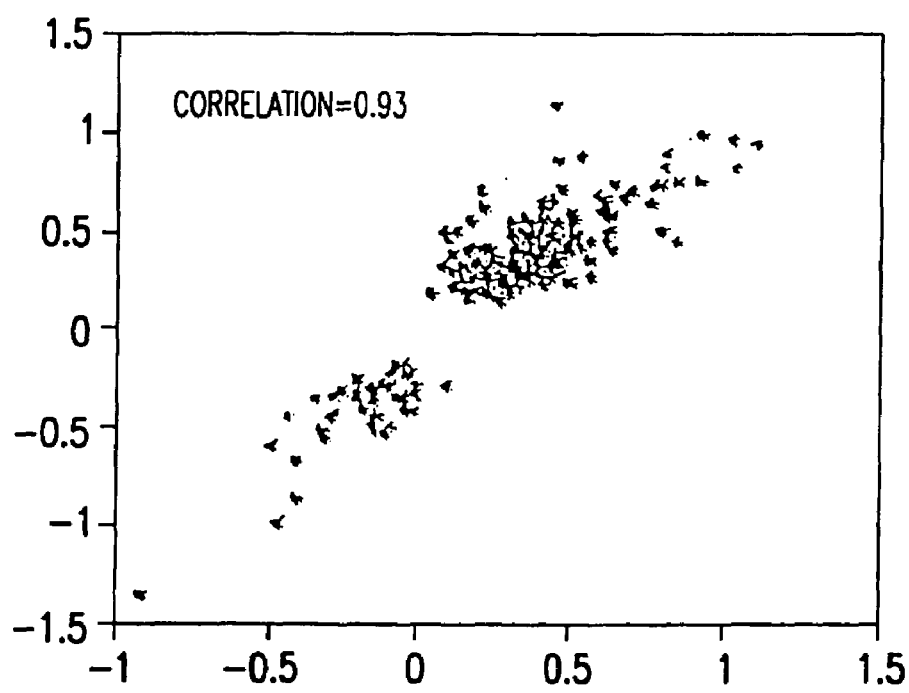
Figure 14C:
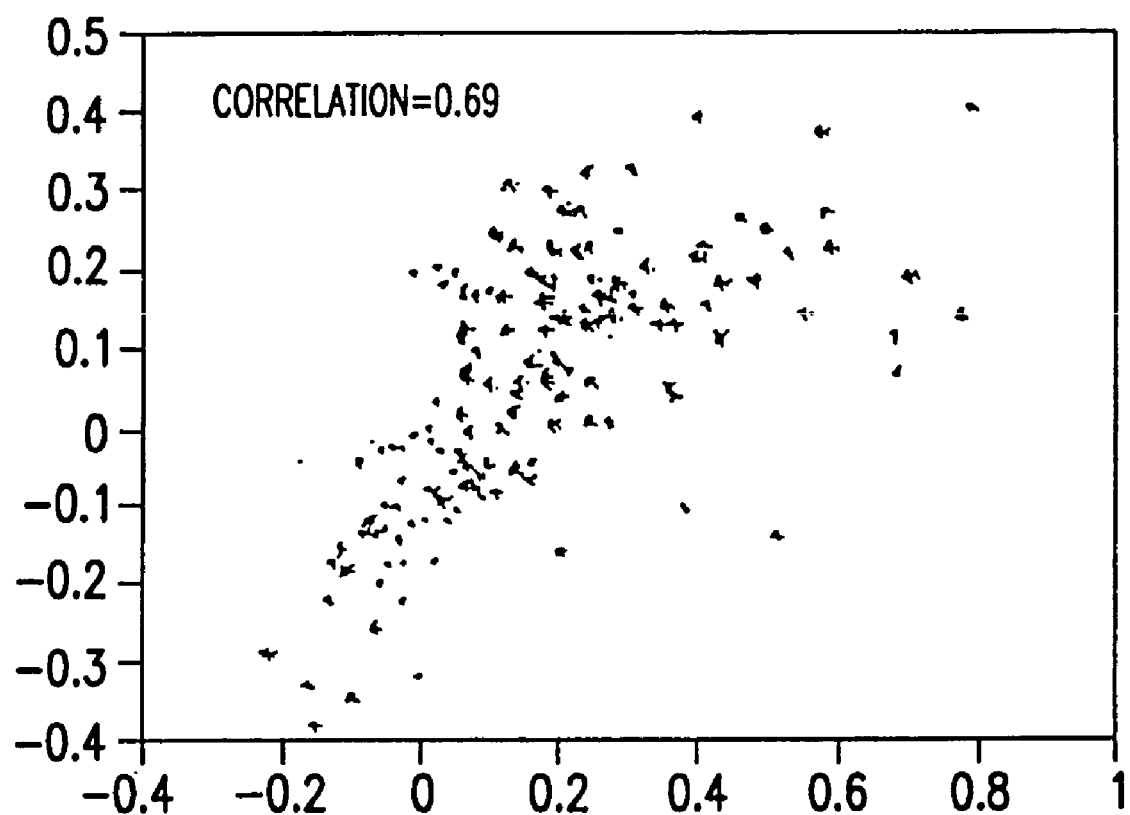

FIGS. 14A–C are scatter plots comparing the changes in "signature" genes in samples of RNA from unactivated to activated human lymphocytes; the horizontal axis indicates changes measured using a signature chip of the invention with an average of 17 oligonucleotide probes per gene; the vertical axis indicates changes measured using a screening chip with only one oligonucleotide probe per gene; FIG. 14A is a scatter plot comparing data for 164 genes for which significant changes were detected with both a screening chip of the invention and a traditional "spotter chip;" FIG. 14B is a scatter plot comparing data for 237 genes for which significant changes were observed with a screening chip but not on a spotter chip; FIG. 14C is a scatter plot comparing data for 149 genes for which significant changes were not observed with a screening chip but were observed with a spotter chip.

Figure 15A:
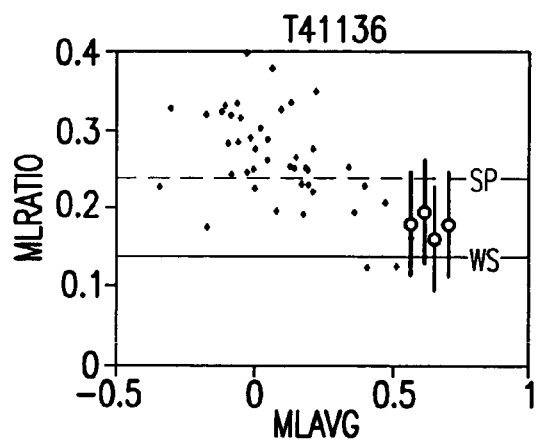
Figure 15B:
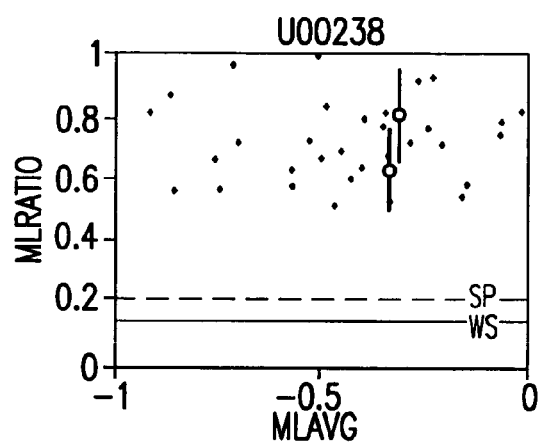
Figure 15C:
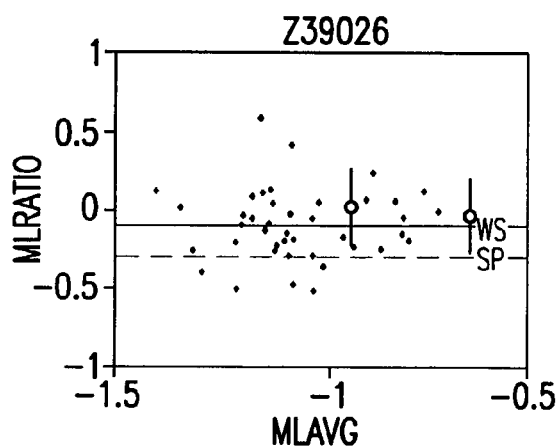
Figure 15D:
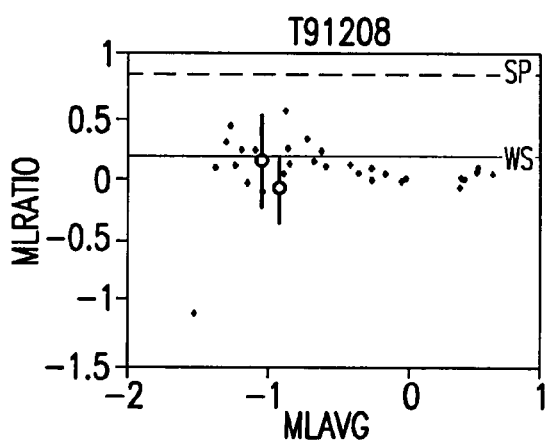

FIGS. 15A–D are exemplary signature plots from four signature genes of the 149 depicted in FIG. 14C for which significant changes were observed in experiments using traditional spotter chips but not in experiments using screening chips; the genes were categorized into four separate classes; FIG. 15A is an exemplary signature plot of a gene (L11066) in Class 1; FIG. 15B is an exemplary signature plot of a gene (M76541) in Class 2; FIG. 15C is an exemplary signature plot of a gene (U33017) in Class 3; FIG. 15D is an exemplary signature plot of a gene (X17620) in Class 4.

Figure 16:
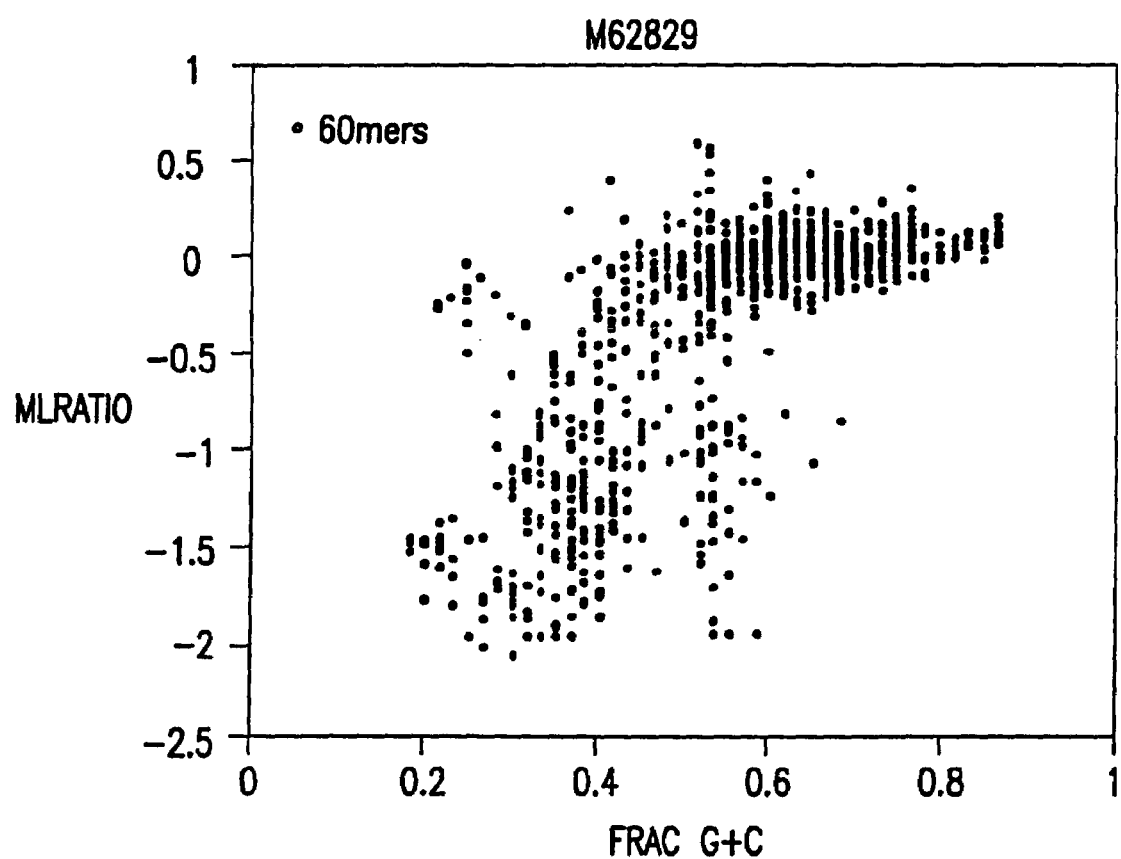

FIG. 16 shows the ratio of ETR103 expression in activated and unactivated human lymphoblast cells reported by exemplary candidate oligonucleotide probes (vertical axis), plotted against the fraction of guanine (G) and cytosine (C) nucleotide bases in each probe.

Figure 17:
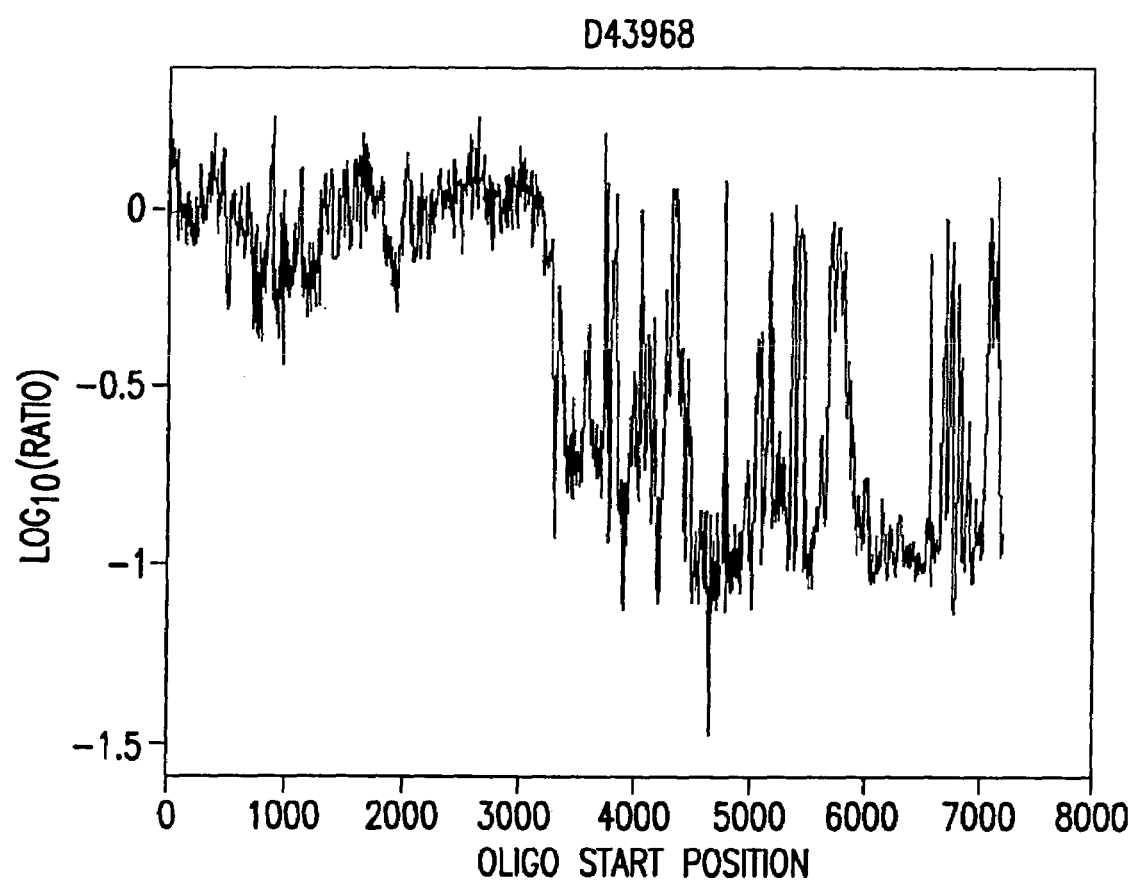

FIG. 17 shows a plot of the ratio of AML1b expression in Jurkat to K562 cells reported by exemplary candidate oligonucleotide probes (vertical axis) verses the position of the each probe's complementary sequence in the AML1b gene.

Figure 18A:
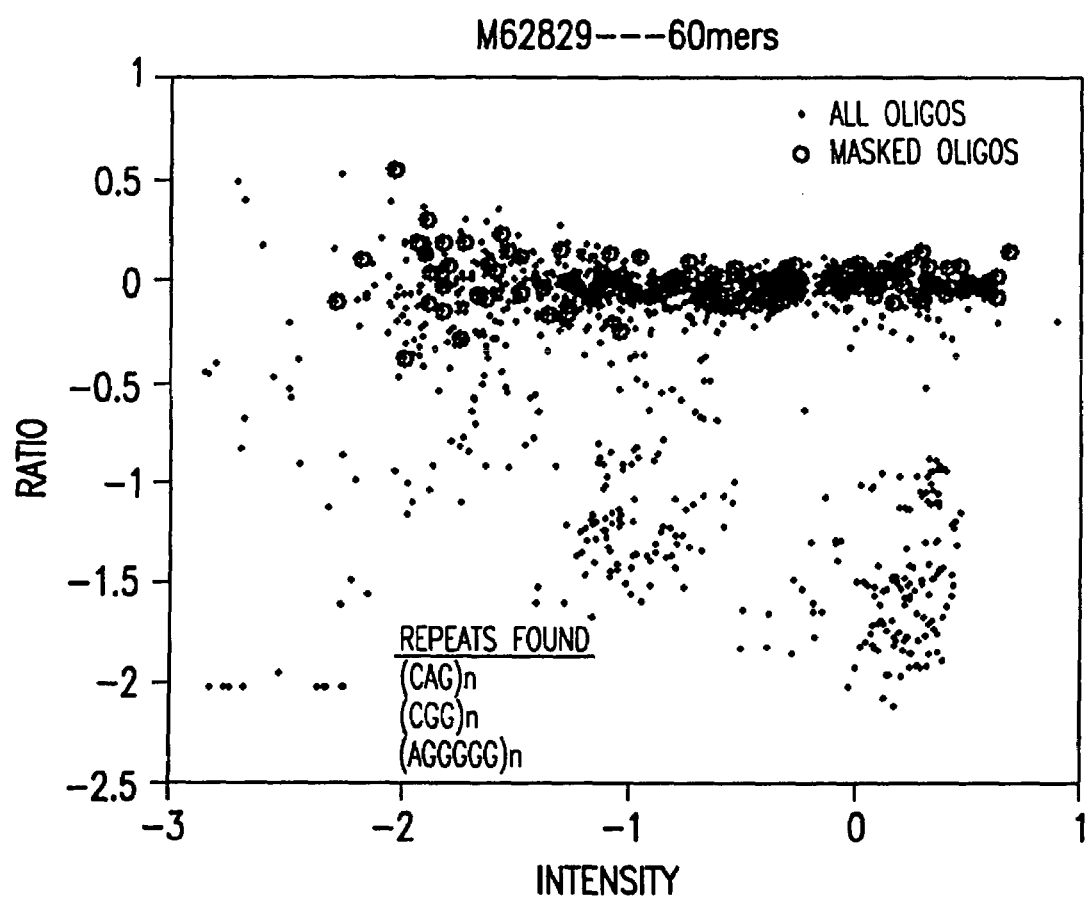
Figure 18B:
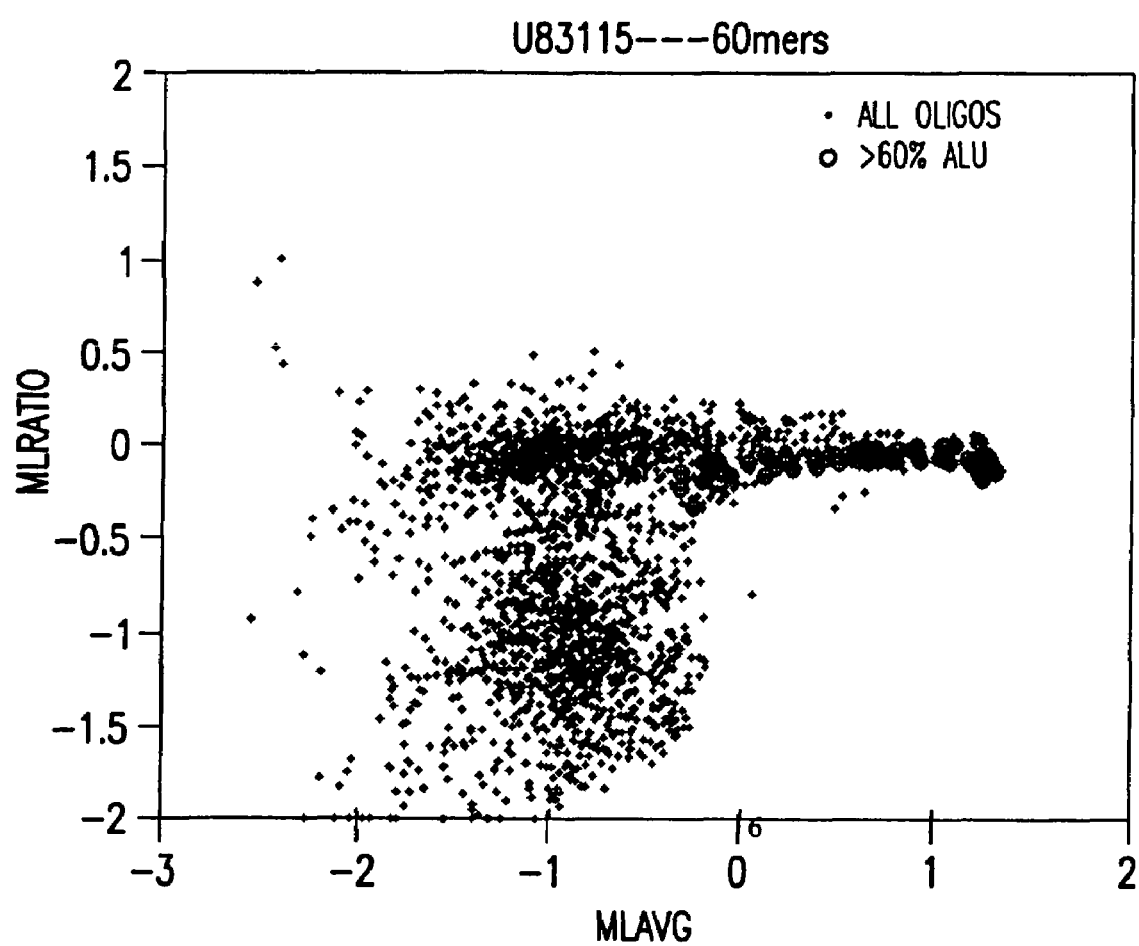

FIGS. 18A–B illustrate the effect of simple and complex repetitive sequence elements on oligonucleotide probe specificity; FIG. 18A plots the reported differential hybridization of exemplary candidate probes to the ERT103 gene (vertical axis) plotted against the hybridization intensity of each probe (horizontal axis) with probes containing one or more of the repetitive elements $(CAG)_n$, $(CGG)_n$ and $(AGGGGG)_n$ indicated by open circles; FIG. 18B plots the reported differential hybridization of exemplary candidate probes to the AIM1 gene (vertical axis) plotted against the hybridization intensity of each probe (horizontal axis) with probes for which greater than 60% of the probe sequence is contained within an ALU repeat identified in the AML1b gene being indicated by open circles.

Figure 19:
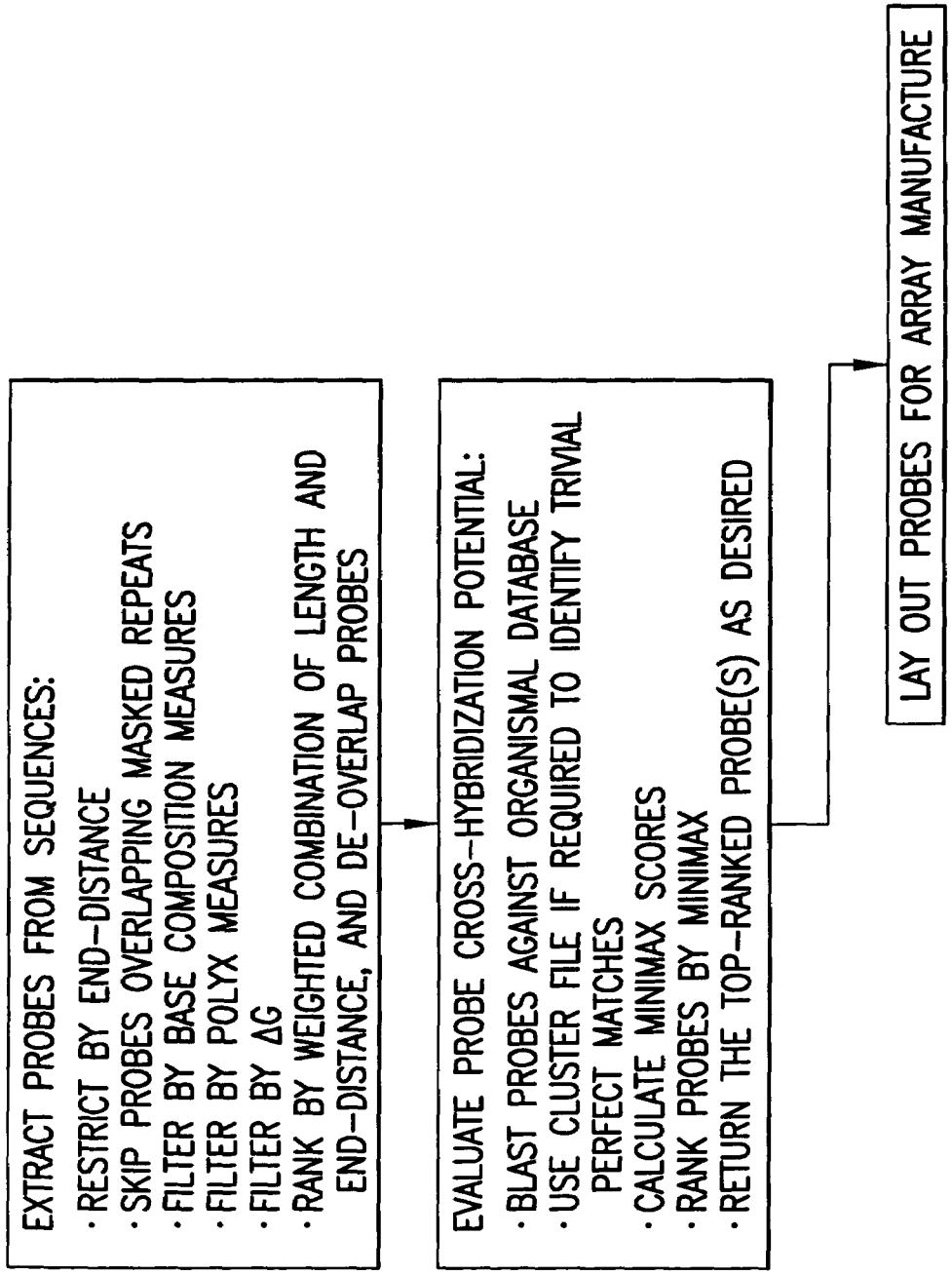

FIG. 19 shows a flow chart illustrating a preferred, exemplary embodiment of the ranking methods of the invention.

5. DETAILED DESCRIPTION

The present invention provides methods and compositions for detecting and reporting changes in gene expression in a cell or cells. In particular, the invention provides methods and compositions that may be used to efficiently and accurately detect a plurality of target polynucleotides in a sample, e.g., by hybridization to a microarray. The invention therefore relates to hybridization of samples comprising a plurality of different target polynucleotides to a plurality of different probes for those target polynucleotides.

Exemplary target polynucleotides which may be analyzed by the methods and compositions of the present invention include, but are not limited to DNA molecules such as genomic DNA molecules, cDNA molecules, and fragments thereof including oligonucleotides, ESTs, STSs, etc. Target polynucleotides which may be analyzed by the methods and compositions of the invention also include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA) and messenger RNA is purified from the total extracted RNA. cDNA is then synthesized from the purified mRNA using, e.g., oligo-dT or random primers. In another preferred embodiment, the target polynucleotides are cRNA prepared from purified messenger RNA extracted from cells (see, e.g., U.S. Pat. Nos. 5,891,636, 5,716,785 and 5,545,522; see also, U.S. patent application Ser. No. 09/411,074, filed Oct. 4, 1999 by Linsley and Schelter). Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}P$, $^{35}S$, $^{14}C$, $^{15}N$ and $^{125}I$. Fluroescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carobxy-X-rhodamine ("ROX"), HEX, TET, IRD40, and IRD41. Fluroescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

The target polynucleotides which are analyzed (e.g., detected) by the methods and compositions of the invention are contacted to a probe or to a plurality of probes under conditions such that polynucleotide molecules having sequences complementary to the probe hybridize thereto. As used herein, a "probe" refers to polynucleotide molecules of a particular sequence and to which target polynucleotide molecules having a particular polynucleotide sequence (generally a sequence complementary to the probe sequence) are capable of hybridizing such that hybridization of the target polynucleotide molecules to the probe can be detected. The polynucleotide sequences of the probes may be, e.g., DNA sequences, RNA sequences, or sequences of a copolymer of DNA and RNA. For example the polynucleotide sequence of the probes may be full or partial sequences of genomic DNA, mRNA sequences extracted from cells, cDNA sequences reverse transcribed from RNA (e.g., mRNA) sequences, or cRNA sequences transcribed from cDNA sequences. The polynucleotide sequences of the probes may also be synthesized, e.g., by oligonucleotide synthesis. The probe sequences can also be synthesized enzymatically in vivo, enzymatically in vitro (e.g., by PCR), or non-enzymatically in vitro.

Preferably, the probes used in the methods of the present invention are immobilized to a solid support or surface such that polynucleotide sequences which are not hybridized or bound to the probe or probes may be washed off and removed without removing the probe or probes and any polynucleotide sequence bound or hybridized thereto. For example, the probes may comprise double-stranded DNA comprising genes or gene fragments or sequences derived therefrom bound to a solid support or surface such as a glass surface or a blotting membrane (e.g., a nylon or nitrocellulose membrane). In one particular embodiment, the probes will comprise an array of distinct oligonucleotide sequences bound to a solid support or surface, such as a glass surface. Preferably, the array of sequences is an addressable array. Specifically, each particular probe (or rather each particular probe sequence) is preferably located at a particular, known location on the surface or support.

Generally, the oligonucleotide sequences will be between 15 and 500 nucleotide bases in length, more preferably between 20 and 100 nucleotide bases in length. However, larger oligonucleotide sequences (i.e., between 40 and 80 bases in length) are particularly preferred. Thus, for example, in certain preferred embodiments the oligonucleotide probe sequences can be between 40–80, 45–80, 50–80, 55–80 bases in length or, alternatively, between 40–75, 40–70, 40–65, 40–60, 40–55, 4014 50, 45–75, 45–70, 45–60, 45–55, 50–75, 50–70, 50–65, 50–60, 55–75, 55–70, 55–65 and 55–60 bases in length. Specific, exemplary oligonucleotide sequence lengths which may be used as probes in the present invention include oligonucleotide sequences which are 20, 25, 30, 35, 40, 45, 50, 55 and 60 bases in length. Sequences of about 50 to 60 bases in length are particularly preferred.

Figure 13:
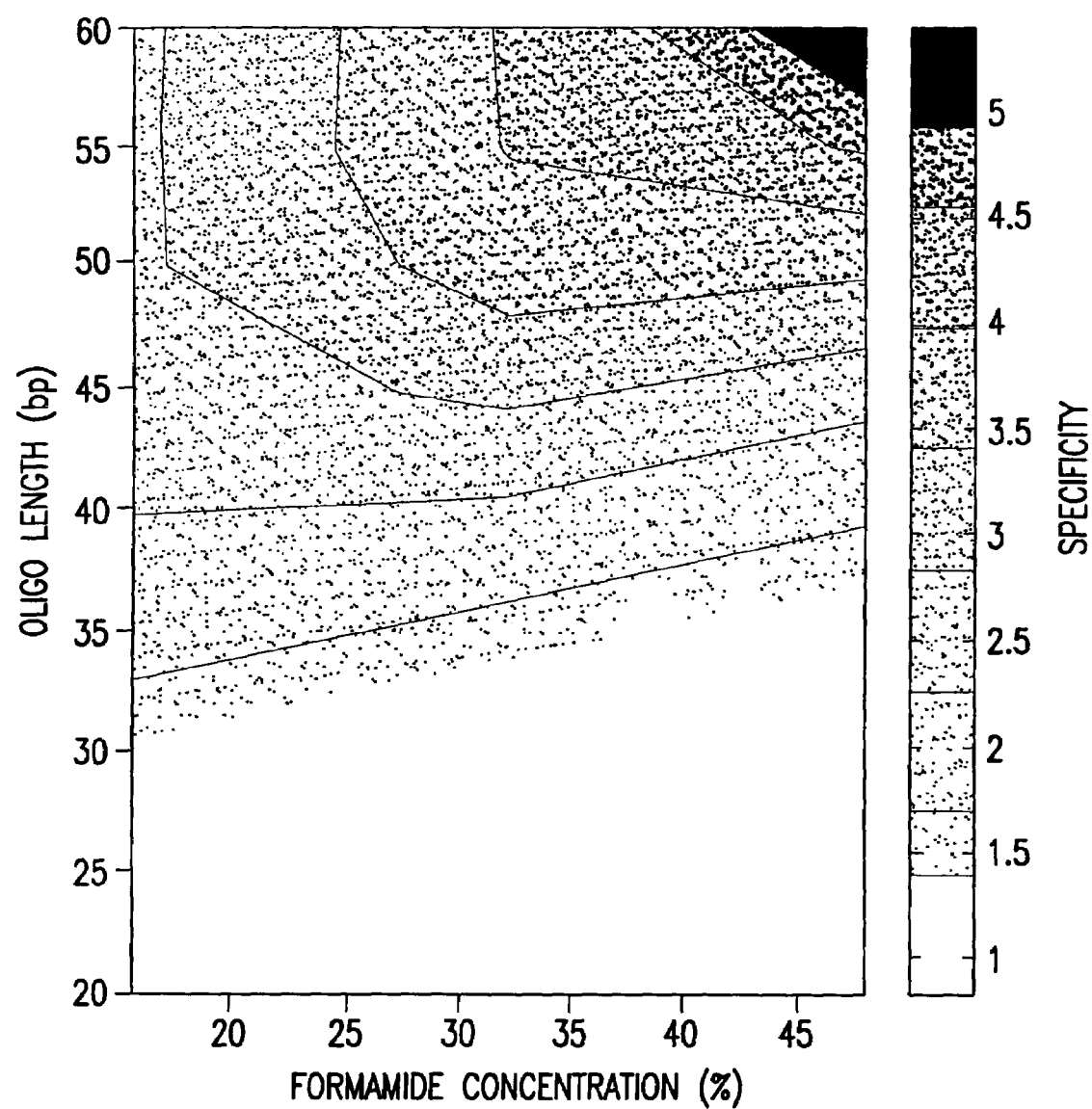
FIG. 13 is a plot showing the specificity of oligonucleotide probes for both sequence length (vertical axis) and hybridization stringency (horizontal axis).

Longer oligonucleotide sequences can be readily identified which hybridize both more specifically and more sensitively to a particular target polynucleotide sequence than do shorter oligonucleotide sequences (e.g., less than 40 bases in length) and longer full length DNA sequences (e.g., full length cDNA sequences). FIG. 13, which plots the specificity of oligonucleotide probes of various lengths and under various levels of hybridization stringency, demonstrates this point by way of example. Specifically, oligonucleotide microarrays were synthesized, according to the methods described in Section 5.3 below, which comprised an overlapping series of different length oligonucleotides from the S. cerevisiae gene HXT3 (Ko et al., 1993, Mol. Cell. Biol. 13:638–648; GenBank Accession No. L07080). The oligonucleotides included sequences 20, 25, 30, 35, 40, 45, 50, 55 or 60 bases in length and beginning at every third position in the sequence so that oligonucleotide sequences of each specific length "tile" through the complete HXT3 gene sequence (e.g., 20mers that spanned positions 1–20, 4–23, 7–26, etc.). The microarrays were simultaneously hybridized with a Cy3-labeled cRNA sample from an strain of S. cerevisiae bearing a homozygous deletion in the HXT3 gene (i.e., an HXT3 gene non-specific sample) and with a Cy5-labeled cRNA sample corresponding the HXT3 gene sequence (i.e., an HXT3 gene specific sample) in the presence of increasing concentrations of formamide (16%, 32% and 48%) which correlate with hybridization stringency. The absolute hybridization intensity and the ratio of hybridization intensity of the HXT3 gene specific to the non-specific sample were determined, as described, e.g., in Section 5.2 below and in FIG. 6. In particular, the ratio of the HXT3 gene specific to non-specific hybridization, which is a measure of hybridization specificity, is plotted in FIG. 13 for the different probe lengths and hybridization intensities. As can be seen from the figure, longer oligonucleotide probes (e.g., greater than about 40 bases in length and more preferably 55–60 bases in length) are significantly more specific for the target polynucleotide sequence, particularly under hybridization conditions of higher stringency (e.g., higher levels of formamide).

The invention is based, at least in part, on the discovery that the number of probe sequences required to reliably and accurately report a particular polynucleotide sequence, such as the sequence of a particular gene, may be reduced to as few as one oligonucleotide probe by carefully selecting probes according to the methods described herein. Thus a user can both efficiently and accurately detect, e.g., expression levels of a large number of genes and/or gene products by minimizing the number of probes required to detect each gene or gene transcript according to the methods described herein. For example, using the ranking and/or selection methods of the invention, a user can select specific probes, e.g., for "screening chips" that may be used to screen for expression levels a substantial portion, or even all of the genes or gene transcripts of a particular organism. The invention therefore also provides such screening chips as well as methods for obtaining such screening chips. In certain preferred embodiments, such screening chips will have probes specific to least about 50% of the genes in the genome of an organism, more preferably to at least about 75%, still more preferably to at least about 85%, even more preferably to at least about 90%, and still more preferably to at least about 99%. In fact most preferably, the screening chips of the invention have probes specific to all of the genes (i.e., 100%) in the genome of an organism. In other embodiments, however, the screening chips have probes specific for those particular genes expressed by a particular cell or cell type of interest. In such embodiments, a screening chip will therefore preferably have probes specific for all of the genes expressed by the cell or cell type of interest, which will often be substantially less than 50% of the genes in the entire genome of the cell or organism (e.g., 20%).

The organism may be of any species, including procaryotic organisms, such as *E. coli* and other bacteria, and eukaryotic organisms including, but not limited to, *Saccharomyces cerevisiae*. The organism may also be a higher, multi-cellular organism such as a plant or animal, including mammalian animals such as humans. Preferably the screening chips of the invention comprise no more than 10, more preferably no more than 5 and most preferably only one probe for each target polynucleotide.

In preferred embodiments, such "screening chips" may be used to identify "signature genes," i.e., those genes or gene transcripts that are of particular interest to a user. For example, signature genes can comprise those genes or gene transcripts that are most responsive to a particular perturbation or to a particular class of perturbations. Exemplary types and classes of perturbations including, exposure to one or more drugs, including drugs from a particular family of drugs. Other exemplary types and classes of perturbations can include viral infection, including infection by a particular type or family of virus, or certain types or classes of disease, such as cancer and immune disorders, to name a few.

The ranking and/or selection methods of the invention may be used to select particular probes for efficiently and accurately detecting changes in the expression levels of those signature genes, e.g., on a "signature chip." Thus, such signature chips are also provided by the present invention. In specific embodiments, a signature chip of the invention can contain probes specific for as many as 2,000 or more of the genes most responsive to a particular change or perturbation to the cell or organism. More preferably, however, signature chips comprise probes specific for the 5, 20, 50, 100 or more of the genes most responsive to a particular change or perturbation to the cell or organism. In certain preferred embodiments, the signature chips comprise at least two probes (i.e., one probe pair) for each target polynucleotide: a "match sequence" probe, which is complementary to a particular target polynucleotide; and at least one "mismatch sequence" probe, whose polynucleotide sequence is only partially complementary (e.g., contains 1–3 mismatched bases) to the particular target polynucleotide. In such embodiments, the signature chips preferably comprise at least five match sequence probes for each target polynucleotide, more preferably at least 10 match sequence probes, still more preferably at least 20 match sequence probes. In such embodiments, the signature chips comprise at least 1 mismatch sequence probe for each match sequence probe. More preferably, however, the signature chips comprise a plurality of mismatch sequence probes (e.g., 4 to 10) for each match sequence probe.

In other, more preferred embodiments, the signature chips comprise only match sequence probes for each target polynucleotide. In such embodiments, the signature chips preferably comprise at least 5, more preferably at least 10, and still more preferably at least 15 (e.g., between 15–20), match sequence probes for each target polynucleotide.

The methods and compositions of the invention are described, in detail, below. In particular, Section 5.1 provides a general overview of the ranking and selection methods of the invention, as well as the screening chips and signature chips which are designed according to such methods. Section 5.2 describes, in detail, the preferred analytical systems used to practice the methods described in Section 5.1. Section 5.3 provides exemplary systems, such as microarrays, which can be used to measure hybridization and/or cross hybridization levels and which can therefore be used in the methods of the present invention.

The detailed description is by way of several exemplary illustrations, in increasing detail and specificity, of the general methods and compositions of the invention. These examples are non-limiting and related variants that will be apparent to one skilled in the art are intended to be encompassed by the appended claims.

5.1. Overview of the Invention

Figure 1:
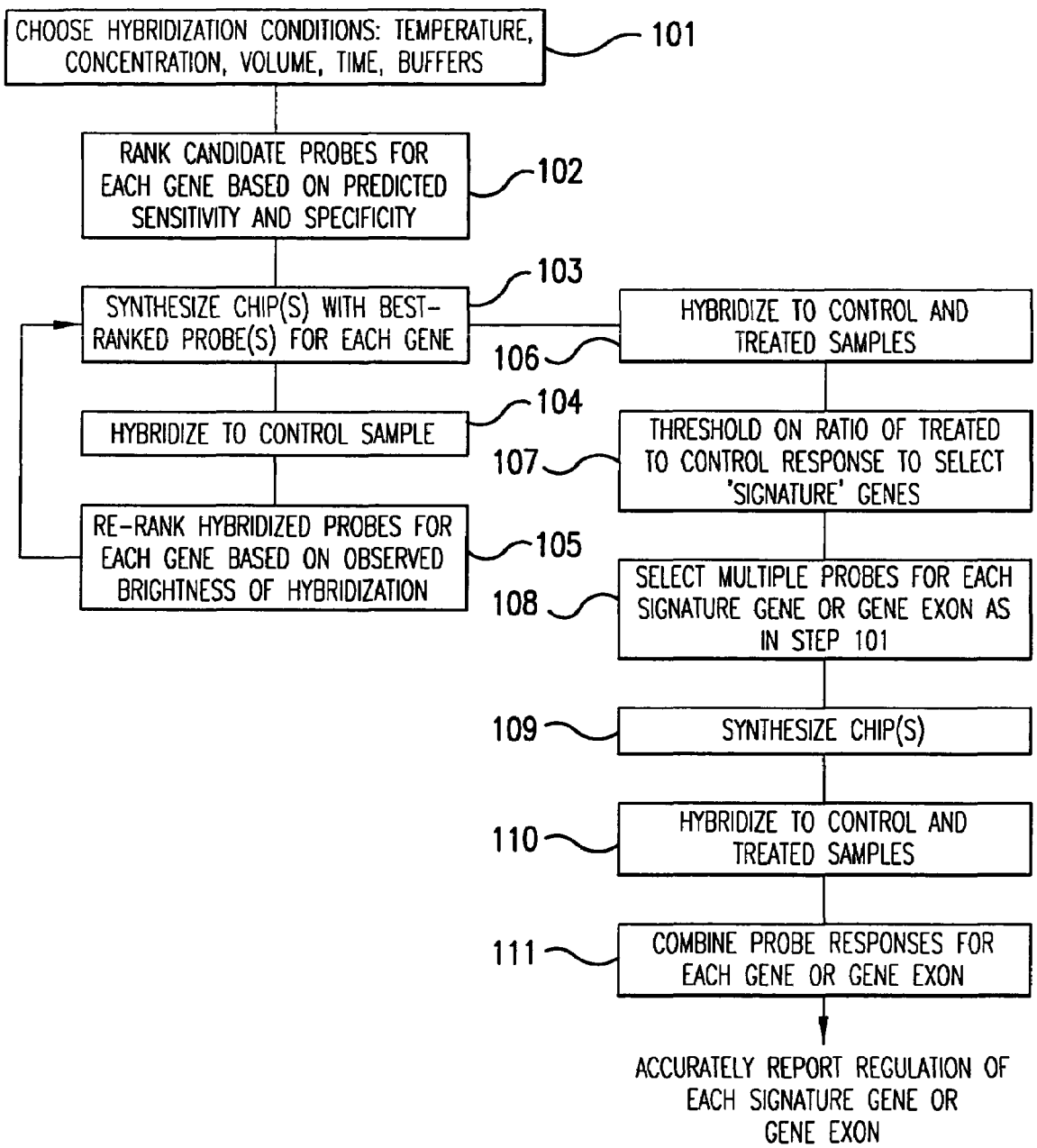

A flow chart illustrating an exemplary, non-limiting embodiment of the general methods of the present invention is shown in FIG. 1. In this particular embodiment, hybridization conditions are first provided or determined (101), as described in subsection 5.1.1 below, to optimize the specificity of each probe for its target polynucleotide sequence. Candidate oligonucleotide probes are then ranked and/or selected (102), according to the methods described below in subsection 5.1.2, based on their sensitivity and specificity for their target sequences, and screening chips are then synthesized (103) using the selected probes. In preferred embodiments, the candidate probes are further ranked and selected according to empirical, iterative methods (FIG. 1; steps 104–105) which are described below in subsection 5.1.3. For example, in preferred embodiments, no more than 10, no more than 5, no more than 4, no more than 3, or no more than 2 candidate probes are identified for each target polynucleotide. Most preferably, one candidate probe is identified for each target polynucleotide. The ranking and/or selection methods described herein are particularly useful to design both screening chips and signature chips which may be used, e.g., to examine changes in genetic expression in cells. Briefly, the screening chips of the invention are particularly useful for applications wherein a sample must be screened for a large number of polynucleotide sequences, e.g., the entire genome of an organism or a substantial fraction thereof. By contrast the signature chips of the invention are most useful for obtaining an accurate measurement of changes in the level of a relatively small number of polynucleotide sequences in a sample, such as changes in the expression of certain specific genes of interest to a user. Such screening and signature chips are therefore also considered a part of the present invention and are described below in Sections 5.1.4 and 5.1.5, respectively.

5.1.1. Hybridization Conditions

Hybridization conditions, such as conditions of salt and temperature, that are appropriate for hybridizing target polynucleotide molecules to one or more probe sequences are generally well known in the art. For example, conditions of higher temperature and lower salt concentration, or "high stringency," are generally preferred to minimize cross-hybridization. Exemplary highly stringent conditions comprise hybridization to filter-bound DNA in 5×SSC, 1% sodium dodecyl sulfate (SDS), 1 mM EDTA at 65° C. followed by post hybridization washing in 0.1×SSC/0.1% SDS at 68° C.

(Ausubel et al., Eds., 1989, *Current Protocols in Molecular Biology*, Vol. 1, Green Publishing Associates, Inc., and John Wiley & Sons, Inc., New York at p. 2.10.3). Conditions of high stringency can also be produced by addition of a denaturant such as formamide. Particularly preferred hybridization conditions comprise: incubation for 12–24 hours at, e.g., 40° C., in 1 M NaCl, 50 mM MES buffer (pH 6.5), 0.5% sodium sarcosine and 30% formamide.

Figure 2:
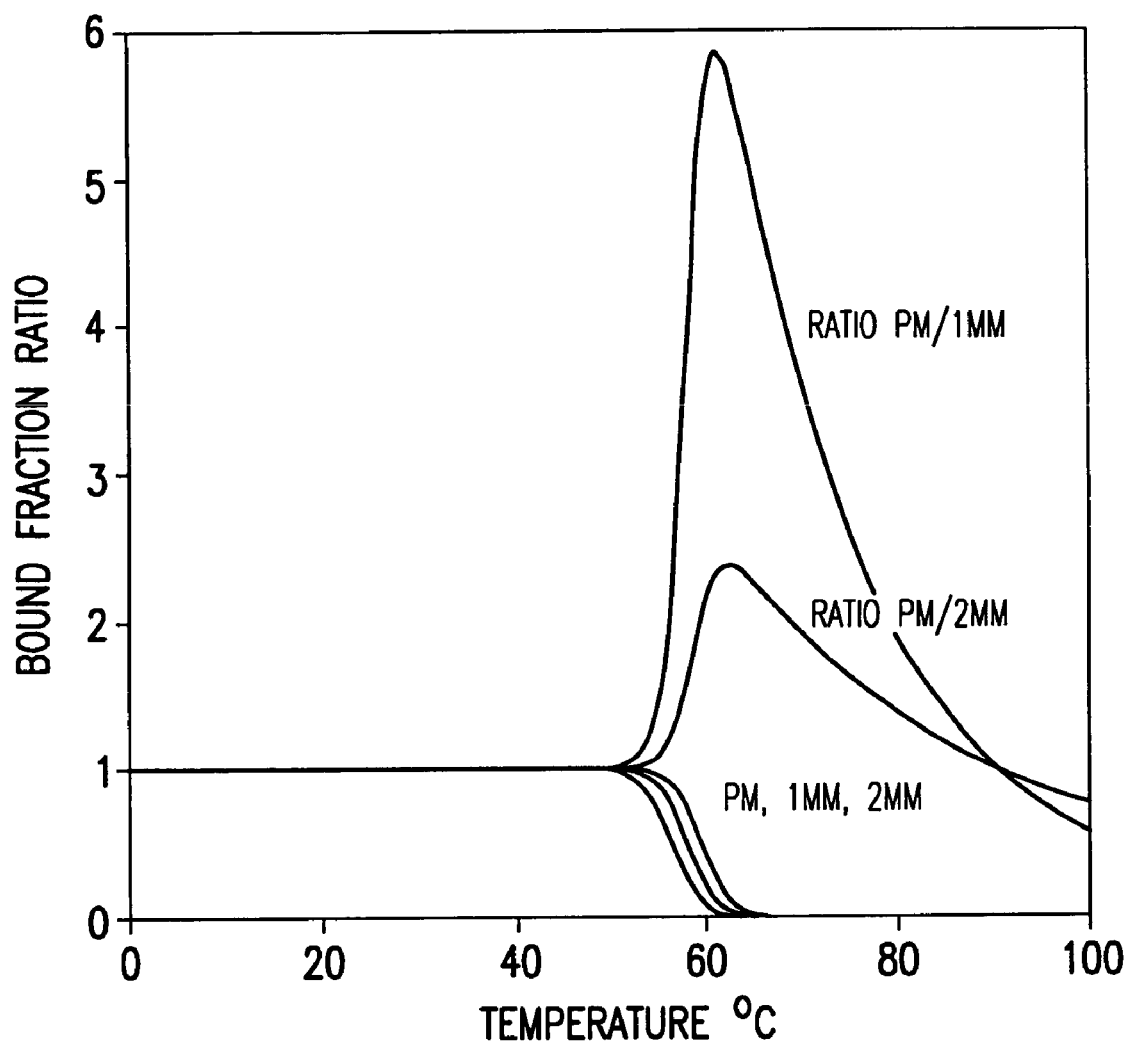
Figure 3A:
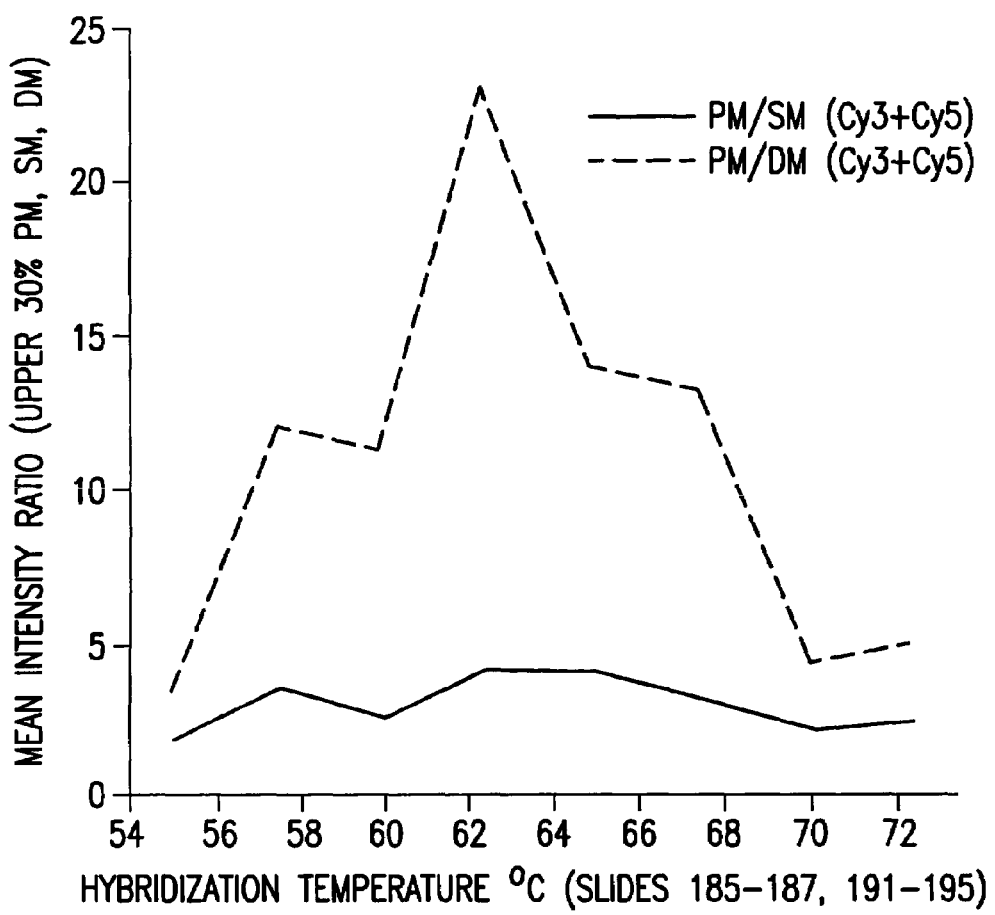
Figure 3B:
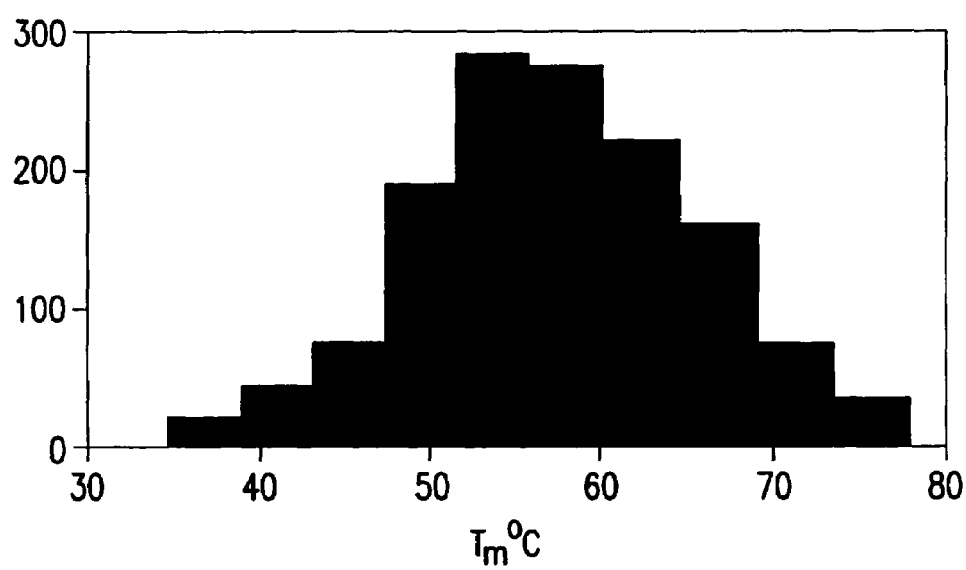
Figure 3C:
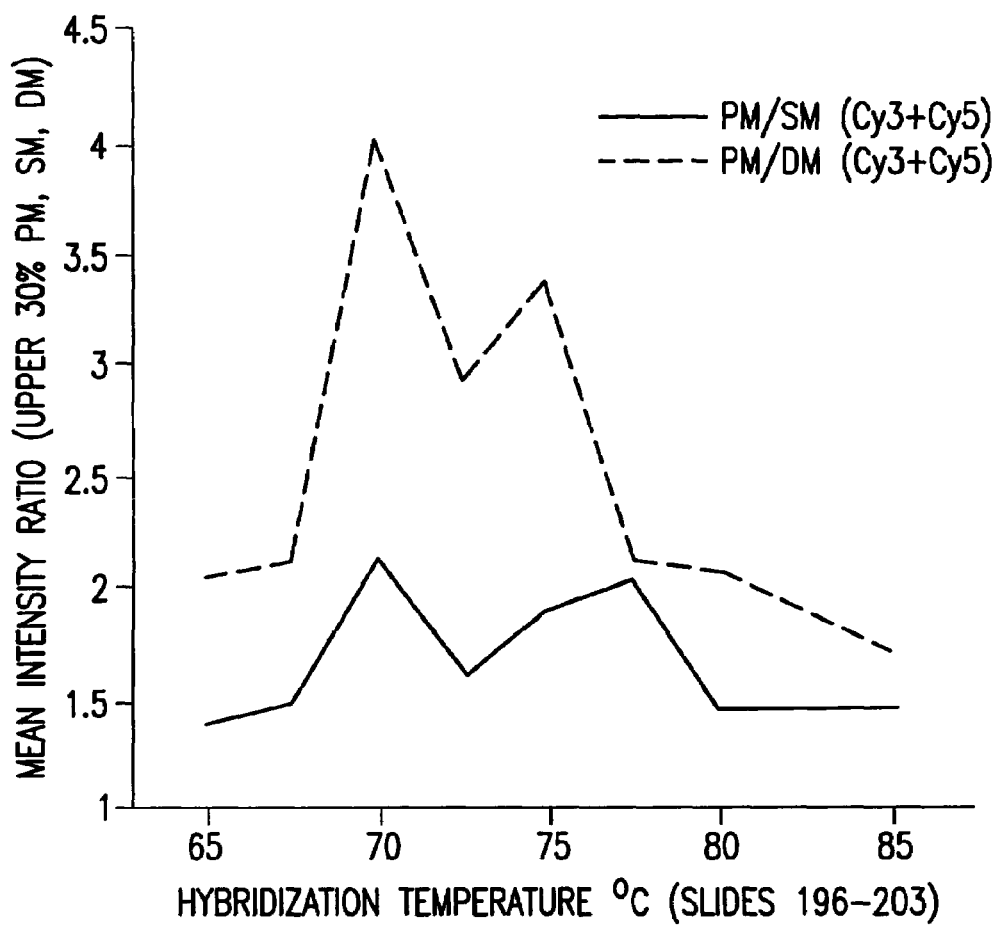
Figure 3D:
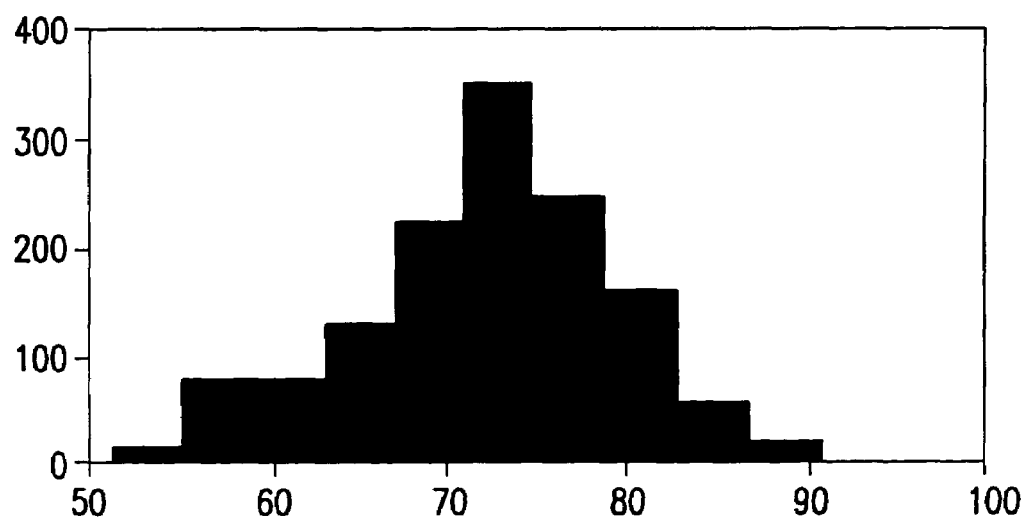

In particular, the hybridization conditions used in the methods of the invention are preferably such that the amount of specific hybridization is maximized while the amount of cross-hybridization or non-specific hybridization is minimized. In those preferred embodiments where target polynucleotides hybridize to oligonucleotide probes, specificity may be maximized by hybridizing at a temperature that is at or near (e.g., within 2° C. or within 5° C.) the melting temperature ("$T_m$") of the target polynucleotide and probe. This fact is illustrated, e.g., in FIGS. 2 and 3. FIG. 2 shows an exemplary, calculated "melting curve" for a perfect match and two imperfect match duplexes. Specifically, FIG. 2 depicts a plot of the predicted fraction of target polynucleotides bound to an oligonucleotide probe as a function of the hybridization temperature. The "melting temperature" of any given target polynucleotide to the probe is defined in the art to mean the temperature at which exactly one-half (i.e., 50%) of the target polynucleotide molecules in a sample are bound to the probe. Thus, the melting temperature is the point on the melting curve at which the bound fraction of polynucleotide molecules is 0.5 (e.g., 58° C. for the perfect-match duplex in FIG. 2).

The plot depicted in FIG. 2 shows, not only the predicted fraction of perfect match target polynucleotide molecules bound to the probe (PM), but also the fraction of bound polynucleotides having one base mismatch (1MM) or two base mismatches (2MM) to the probe. The plot depicted in FIG. 2 also shows the ratio of bound perfect match to bound 1 base or 2 base mismatch target polynucleotides at a given temperature. By maximizing these ratios, the amount of specific (i.e., PM) hybridization is maximized while minimizing cross hybridization, e.g., from 1MM and 2MM in FIG. 2. Inspection of FIG. 2 reveals that these ratios are maximized at about 62° C., i.e., slightly above the melting temperature of the perfect match duplex.

FIG. 3 shows the experimental verification of this principle. Specifically, oligonucleotide probes of either 22 or 35 nucleotides in length (i.e., 22-mer's or 35-mers) were synthesized using standard inkjet printing techniques known in the art (see Blanchard, International Patent Publication WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123). Each of the synthesized probes was either a perfect match, single or double base mismatch to a specific target polynucleotide sequence. FIG. 3A shows a plot of the observed ratio of hybridization intensities to this target polynucleotide sequence between the perfect match and single mismatch 22-mer probes (PM/SM, solid line) and between the perfect match and double mismatch 22-mer probes (PM/DM, dashed line). A histogram showing the predicted perfect-match melting temperature for each 22-mer probe is shown in FIG. 3B. FIGS. 3C and 3D show an identical analysis of the hybridization and predicted melting temperatures of the 35-mer probes. In both FIGS. 3A and 3C, the highest ratio (and hence highest specificity) between perfect match and mismatch probes is obtained at a hybridization temperature that is equal to or slightly above the median melting temperature in FIGS. 3B and 3D, respectively.

Methods for determining the melting temperature of a particular polynucleotide duplex are well known in the art and include, e.g., predicting the melting temperature using well known physical models adapted to experimental data (see, e.g., SantaLucia, J., 1998, *Proc. Natl. Acad. Sci. U.S.A.* 95:11460–1465 and the references cited therein). Mathematical algorithms and software for predicting melting temperatures using such models are readily available as described, e.g., by Hyndman et al., 1996, *Biotechniques* 20:1090–1096. For example, the melting temperature for an RNA/DNA duplex 25 base pairs in length in 1 M salt solution is between about 60 to about 70° C.

In preferred embodiments, the methods of the invention are practiced using a plurality of oligonucleotide probes, e.g., in a microarray such as those described in Section 5.3 below. In such embodiments, it is generally not feasible or desirable to select and/or use individual hybridization conditions that are optimized for each individual probe. Rather, a single set of hybridization conditions is preferably selected and used that optimizes hybridization of polynucleotide molecules overall to all of the oligonucleotide probes. For example, in such embodiments the melting temperatures of the perfect match polynucleotide molecules from each probe will typically fall within some range of temperatures. In such embodiments, therefore, the hybridization temperature is selected to be near or at the upper limit of this range.

5.1.2. Properties Affecting Target and Cross-Hybridization

Candidate oligonucleotide probes are ranked and/or selected based on at least two, and preferably on a plurality of properties and/or parameters. For example, in the exemplary embodiment illustrated in FIG. 1, candidate oligonucleotide probes are ranked and/or selected (102) based on both their sensitivity and specificity for their target polynucleotide sequence. As used herein, the "sensitivity" of a probe refers to the fraction of molecules of the probe that hybridize to polynucleotide molecules (or that have polynucleotide molecules hybridized thereto) under a particular set of hybridization conditions (e.g., the selected or provided hybridization conditions). The "specificity" of a probe, as used herein, is understood to refer to the ratio of target (e.g., perfect match) polynucleotide molecules to non-target polynucleotide molecules hybridized to the probe under a particular set of hybridization conditions (e.g., the selected or provided hybridization conditions).

Other properties and parameters by which candidate oligonucleotide probes can be ranked including, but are not limited to: (a) probe size or length; (b) binding energies, including both the perfect match duplex (i.e., of a probe and its target, complementary nucleotide sequence) and cross-hybridization binding energies; (c) base composition, including, for example, the relative amount or percentage of one or more particular nucleotide bases (e.g., adenine, guanine, thymine or cytosine) in a probe sequence, as well as the relative amount or percentage of any combination of such nucleotide bases; (d) the position of a probe's complementary sequence in the sequence of its "target" polynucleotide or gene sequence; and (e) probe sequence complexity, including the presence or lack of common repetitive elements such as polynucleotide repeats (i.e., simple, contiguous repeats of one or more nucleotide bases) as well as more complicated repetitive elements that are well known in the art. Still other exemplary parameters which can be used in the methods and compositions of the invention for ranking and/or selecting oligonucleotide probes include: (f) self dimer binding energy (i.e., the tendency for a particular probe to hybridize to its own sequence); (g) the structure content of the complementary, target polynucleotide sequence for a particular probe (e.g., the presence or absence of certain structural features or motifs); and (h) the information content of a probe's nucleotide sequence. Each of these properties is discussed, in detail, hereinbelow.

Preferably, the target polynucleotide sequence of a candidate probe is its "perfect match" sequence, i.e., to polynucleotide molecules that comprise the nucleotide sequence that is complementary to the sequence of the oligonucleotide probe and which, therefore, hybridize to the probe with no mismatches.

Figure 4:
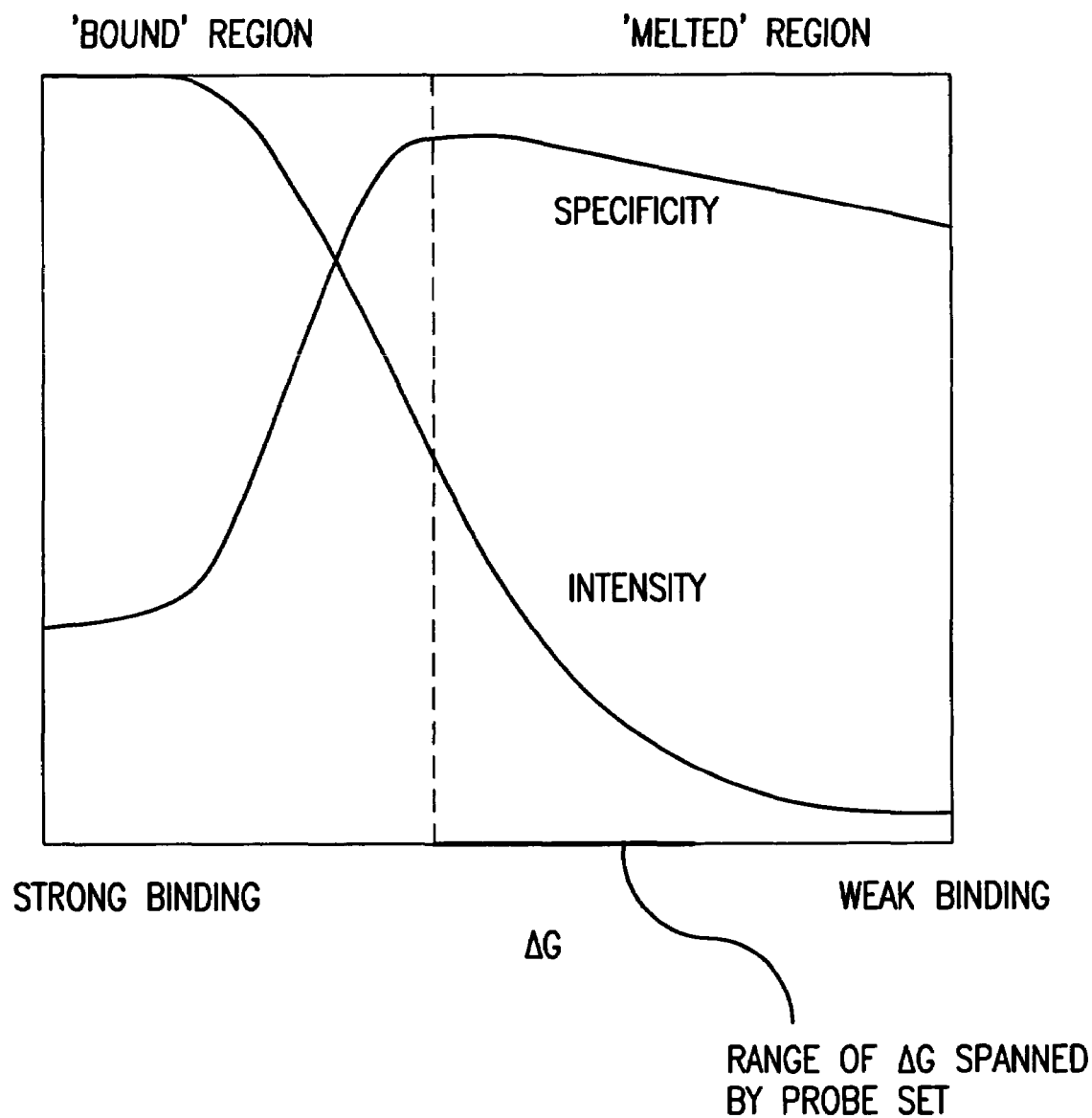

Evaluating Binding Energy:

Both the sensitivity and specificity of a particular probe depends upon the binding energies, $\Delta G$, of polynucleotide molecules to the probe, as shown in FIG. 4. In particular, the hybridization intensity traces a sigmoidal curve which follows the melting curve of the probe, decreasing as the binding energy increases. Specificity, however, is maximum at or slightly above the melting temperature of the probe (i.e., at a binding energy that is equal to or slightly greater than zero). Thus, in preferred embodiments, the sensitivity and/or specificity are determined or predicted from the binding energies.

It is noted that the skilled artisan readily appreciates that the term "binding energy," as used herein, refers to the difference of the energy of polynucleotide molecules (e.g., a target polynucleotide and a polynucleotide probe) when they are in a bound state (i.e., when they are bound or hybridized to each other) from when they are in an unbound state. This definition is readily expressed mathematically by the formula $\Delta G = G_{bound} - G_{unbound}$. Thus, a polynucleotide that has the "largest" binding energy to a particular probe is one for which the difference between the energies of the bound and unbound polynucleotide is greatest. In particular and as the skilled artisan also readily appreciates, because the energy of polynucleotides in a bound state is ordinarily lower than the energy of the unbound polynucleotides, the binding energy (i.e., $\Delta G$) will ordinarily be a negative number. Thus, as used herein, the polynucleotide having the "largest" binding energy to a particular probe will, in fact, be the polynucleotide for which $\Delta G$ is the most negative.

Binding energies for polynucleotide duplexes, and particularly for oligonucleotide duplexes in solution, may be readily obtained or predicted, at least in part, by using theoretical models known in the art, including, e.g., "nearest-neighbor" models such as those described by SantaLucia, 1998, *Proc. Natl. Acad. Sci. U.S.A.* 95:1460–1465. Such models assume that the stability (i.e., the binding energy) of individual base-pairs in a polynucleotide duplex depends upon the identity and orientation of the neighboring base pairs. The binding energy $\Delta G$ is therefore expressed as a sum of the free energies of the individual dimer duplexes and "initiation factors" for duplex formation. Thus, for example, for DNA/RNA complexes there are 16 unique Watson-Crick dimer duplexes which are listed in Table I, below.

TABLE I

| DNA/RNA WATSON-CRICK DIMER DUPLEXES | | | |
|---|---|---|---|
| 5'-A.A-3' | 5'-T.A-3' | 5'-C.A-3' | 5'-G.A-3' |
| 3'-U.U-5' | 3'-A.U-5' | 3'-G.U-5' | 3'-C.U-5' |
| 5'-A.T-3' | 5'-T.T-3' | 5'-C.T-3' | 5'-G.T-3' |
| 3'-U.A-5' | 3'-A.A-5' | 3'-G.A-5' | 3'-C.A-5' |

TABLE I-continued

| DNA/RNA WATSON-CRICK DIMER DUPLEXES | | | |
|---|---|---|---|
| 5'-A.C-3' | 5'-T.C-3' | 5'-C.C-3' | 5'-G.C-3' |
| 3'-U.G-5' | 3'-A.G-5' | 3'-G.G-5' | 3'-C.G-5' |
| 5'-A.G-3' | 5'-T.G-3' | 5'-C.G-3' | 5'-G.G-3' |
| 3'-U.C-5' | 3'-A.C-5' | 3'-G.C-5' | 3'-C.C-5' |

Thus, for example, the binding energy of a particular 16-mer polynucleotide duplex may be determined, according to a nearest neighbor model, by the equation:

$$\Delta G = \sum_{i=1}^{16} q_i \Delta g_i + q_{17} \Delta g_{17} + q_{18} \Delta g_{18} \quad \text{(Eq. 1)}$$

In particular, in Equation 1 above, $\Delta g$ is the binding energy of the i'th individual dimer duplex and $q_i$ is the number of occurrences of the i'th individual dimer duplex in the polynucleotide complex of interest. Two "initiation parameters" $\Delta g_{17}$ and $\Delta g_{18}$ are also used in the model, and $q_{17}$ and $q_{18}$ are the number of terminal (i.e., end) base pairs that are A/T and G/C base pairs, respectively. Generally, the individual dimer-duplex binding energies and initiation parameters have values that are already known in the art (see, e.g., SantaLucia, supra). Alternatively, such parameters can be experimentally determined, e.g., by a user, as explained below.

It is understood that the nearest neighbor models used in the methods of the present invention may comprise additional binding energy terms besides the initiation parameters and dimer binding energies discussed above. In particular, the nearest neighbor models of the invention can also be used to calculate or predict the binding energy of polynucleotide duplexes comprising one or more mismatched base pairs by including binding energy terms for additional dimer-duplexes that contain a base-pair mismatch. Dimer-duplex binding energies for such mismatch dimer-duplexes can be obtained or determined according to the same methods as those used to obtain or determine the binding energy terms for Watson-Crick dimer duplexes, including the methods described hereinbelow.

In more preferred embodiments of the invention wherein surface bound polynucleotides are employed, such as in microarrays, binding energies can also be estimated from experiments using the same surface-bound polynucleotide probes. Thus, in particularly preferred embodiments wherein the methods of the invention are used to design microarray "chips," the binding energies for oligonucleotide probes can be estimated using the same chips that are being designed. For example, in certain particular, but non-limiting, embodiments, the binding energies of a set of oligonucleotide probes, p=1 to N, on a microarray of N probes can be determined by "spiking" polynucleotide molecules corresponding to a particular sequence into the hybridization solution. Specifically, a concentration, c, of polynucleotide molecules corresponding to the particular sequence is hybridized to the probes of the microarray, and the hybridization level, $I_p$, of the particular polynucleotide molecules to each probe p is measured. Under the preferred hybridization conditions (i.e., high stringency) of the present invention, the hybridization level is related to the polynucleotide concentration and the binding energy, $\Delta G_p$, according to Equation 2:

$$I_p = s \cdot M(c_p) \cdot e^{\Delta G_p / RT} \tag{Eq. 2}$$

wherein R denotes the ideal gas constant (1.9872 kcal/mol·°K), and T is the hybridization temperature (in degrees Kelvin). s denotes a correction factor, e.g., for detector and label incorporation efficiencies, and $M(c_p)$ is a function related to the concentration of the polynucleotide molecules corresponding to the known sequence. Pursuant to Equation 2 above, the log(intensity) of hybridization is linearly related to the binding energy, i.e.,:

$$\log(I_p) = \log[s \cdot M(c_p)] + \frac{\Delta G_p}{RT} \tag{Eq. 3}$$

In one embodiment, therefore, the hybridization level may be measured or determined for a fixed concentration, $c_p$, of polynucleotide molecules at a plurality of hybridization temperatures T. The binding energy $\Delta G_p$ can then be determined from the slope of the line $\log(I_p)$ v. 1/T. More preferably, however, Equation 3 can also be used to determine the parameters $\Delta g_i$ for use in a nearest neighbor model (i.e., in Equation 1, above). In particular, by using the expression for $\Delta G$ provided in Equation 1, Equation 3 can also be expressed as:

$$\log(I_p) = \log[s \cdot M(c)] + \sum_{i=1}^{18} \frac{q_{i,p}}{RT} \Delta g_i \tag{Eq. 4}$$

wherein $q_{p,i}$ denotes the number of occurrences of the i'th individual dimer duplex in the polynucleotide complex of probe p.

As one skilled in the art readily appreciates, the binding energies of individual dimer duplexes and the initiation parameters (i.e., the $\Delta g_i$) may be determined from Equation 4 above using techniques of mathematical analysis known in the art. For example, Equation 4 may also be represented as an equation of vectors and matrices:

$$\log(I) = \log[s \cdot M(c)] + Q \cdot \Delta g \tag{Eq. 5}$$

Specifically, I in Equation 5 denotes the vector of hybridization intensities $\{I_p\}$ for each probe p of the microarray. $\Delta g$ denotes the "dimer binding energy vector," i.e., the vector of binding energies of individual dimer duplex and initiation parameters (i.e., $\{\Delta g_i\}$), and Q is the matrix of elements $\{q_{p,i}\}$. Thus, provided hybridization intensities for individual probes of a microarray, the dimer binding energy vector may be readily determined, e.g., from a least-squares solution:

$$\Delta g_{LSQ} = (Q^T Q)^{-1} Q^T \log(I) \tag{Eq. 6}$$

in which $Q^T$ denotes the transpose of the matrix Q. Alternatively, a conditioned least squares solution may be used as provided by the equation:

$$\Delta g_{LSQ} = (Q^T Q + \Lambda)^{-1} Q^T \log(I) \tag{Eq. 7}$$

wherein $\Lambda$ is a scaled version of the identity matrix which is optionally used, e.g., to keep the sizes of the elements of $\Delta g$ to within limits, e.g., determined or provided. For example, generally a user will prefer to keep the elements of $\Delta g$ less than or equal to about 8 kcal/M in magnitude. As will be appreciated by one skilled in the art, it is understood that in Equations 6 and 7 above, the constant term s $M(c_p)$ is subsumed into the definition of $\Delta g$. Numerical techniques for solving linear equations such as Equations 6 and 7 above are well known in the art and include, e.g., the numerical methods and algorithms described by Press et al. (1992, *Numerical Recipes in C*, Chapter 2: "Solution of Linear Algebraic Equations," Cambridge University Press).

Although the expression cannot be readily expressed in a linear form as in Equation 3 above, under less preferred hybridization conditions (e.g., of low stringency or moderately stringent hybridization conditions), as one skilled in the art readily appreciates, binding energies and binder parameters (i.e., the $\Delta G$ and $\Delta g$ terms in Equations 3 and 4 above) can nevertheless be obtained or determined from similar systems of equations using methods of analytical and numerical analysis known in the art.

Prediction of Probe Sensitivity and Specificity:

Once binding energies for polynucleotide molecules to the probes are provided or determined, e.g., using a nearest-neighbor model with appropriate parameters $\Delta g_i$, both the sensitivity and specificity of a probe can be readily predicted, e.g., using theoretical models. As discussed above, the level of hybridization of a particular polynucleotide sequence p to a given probe is directly related to the binding energy $\Delta G_p$ of that sequence to the probe. More specifically, the level of "target" hybridization $T_p$, i.e., the level of hybridization of a target polynucleotide sequence p to a particular probe is specified by:

$$T_p = s \cdot M(c_p) \sum_k \exp\left(\frac{\Delta G_{kp}}{RT}\right) \tag{Eq. 8}$$

wherein $\neq G_{k,p}$ is the binding energy of the duplex between the probe and the sequence starting at position k on the target polynucleotide. $M(c_p)$ is the concentration (i.e., abundance) of the target polynucleotide in the hybridization sample, and s denotes a correction factor as explained supra. Likewise the level of cross-hybridization of all other "non-target" polynucleotide sequences $j \neq p$ is specified by:

$$X_p = s \cdot \sum_{j \neq p} M(c_j) \cdot \left[\sum_k \exp\left(\frac{\Delta G_{kj}}{RT}\right)\right] \tag{Eq. 9}$$

wherein $\Delta G_{k,j}$ is the binding energy of the probe starting at position k on the non-target polynucleotide j, and $M(c_j)$ is the concentration (i.e., abundance) of the polynucleotide j in the hybridization sample. Thus, the specificity of the probe for the sequence p is provided by:

$$S_p = \frac{T_p}{X_p} \tag{Eq. 10}$$

As will be readily appreciated by one skilled in the art, it is understood that the specificity provided by $S_p$ in Equation 10 above is independent of the value of the correction factor s in Equations 8 and 9.

In many embodiments, the actual abundance $M(c_j)$ of at least some polynucleotide sequences in a sample will not be known. In such embodiments, it is preferable to set the value of the abundances to unity when evaluating Equations 8–10, above. Also, in many embodiments, the methods and compositions of the invention are used to evaluate polynucleotide expression in cells, such as mammalian cells, whose genomes contain repetitive sequences (see, e.g., Claverie, 1996, *Methods in Enzymology* 266:212–227). In such embodiments, it is preferable to eliminate candidate probes corresponding to such repetitive sequences before evaluating candidate probe sensitivities and specificities. It is still further preferable to eliminate candidate probes corresponding to other sequences of low information content, as explained hereinbelow, before evaluating the sensitivity and specificity of candidate probes.

In most preferred embodiments of the invention, i.e., wherein the methods and compositions of the invention are used to evaluate the entire genome of an organism, complete evaluation of Equation 8–10 requires the evaluation of more than $10^{14}$ exponential terms. Therefore, it is preferable to make certain approximations before evaluating these equations so that the number of numerical calculations is reduced to a manageable size. For example, in certain embodiments, probe candidates are first selected on the basis of their determined or predicted binding energy $\Delta G$, so that only probes having or predicted to have at least a certain minimum binding energy or within some interval of binding energies (determined, e.g., by a user) are evaluated. Still more preferably, before evaluating candidate probes for specificity, the probes are ranked and/or selected according to one or more of the properties described below, such as size and length, base composition, sequence complexity and/or combinations thereof. In other embodiments, wherein the relative abundances of at least some polynucleotide species in a sample are known, only the most abundant polynucleotide sequences are considered when evaluating specificity, e.g., using Equation 10 above. For example, in certain embodiments, only those polynucleotide sequences in a sample which represent, in toto, at least 50% of the total number of polynucleotide molecules in the sample are considered. Alternatively, only those polynucleotide sequences in a sample which represent, in toto, at least 75%, 80%, 85%, 90%, 95%, or 99% of the total number of polynucleotide molecules in the sample are considered.

In particularly preferred embodiments, a homology search method such as BLAST ("Basic Local Alignment Search Tool") and PowerBLAST (see, in particular, Altschul et al., 1990, *J. Mol. Biol.* 215:403–410; Altschul, 1997, Nucleic Acids Res. 25:3389–3402; and Zhang and Madden, 1997, *Genome Res.* 7:649–656) are first performed against each probe sequence to identify polynucleotides, e.g., in a database of expressed sequences such as the GenBank or the dbEST database, which comprises sequences that are most identical or homologous to each probe's complementary sequence. For example, in preferred embodiments, sequences which are at least 50%, 60%, 70%, 80%, 90%, 95%, or 99% identical to a probe's target sequence are identified using a search algorithm such as BLAST or PowerBLAST according to its default parameters. Preferably the search algorithm is employed using parameters set to detect perfect-match sequences of a seed length of, e.g., 7 to 15 or, more preferably, 7 to 12 bases. Binding energies and binding specificity are then evaluated only for polynucleotide sequences identified in such searches.

Preferably, the database of sequence used in such a homology search is a database of or containing all or substantially all of the polynucleotide sequences that are present or are believed to be present in a polynucleotide sample that the probe or probes are intended to assay. Thus, for example, in embodiments wherein the sample is a polynucleotide sample (e.g., mRNA, cDNA or cRNA) derived from a cell or organism, the database is a database of or containing all or substantially all of the polynucleotide sequences expressed by that cell or organism. Such a database can contain, for example, sequences corresponding to 50%, 60%, 70%, 80%, 90%, 95%, 99% or 100% of the polynucleotide sequences expressed by the cell or organism. The database can also contain 50%, 60%, 70%, 80%, 90%, 95%, 99% or 100% of the gene sequences in the genome of the cell or organism.

In a particularly preferred aspect of this embodiment, polynucleotide sequences that are most identical or homologous to each probe's complementary sequence are identified, e.g., using a homology search method such as BLAST or PowerBLAST and their binding (i.e., cross-hybridization) energies to the probe or probes are evaluated (e.g., using the nearest neighbor model and Equation 1, described above). In this embodiment, the strongest binding energy calculated, which is referred to herein as the "minmax score", is used in place of the score provided in Equation 10, above, as an indication of the probe's predicted cross-hybridization. Preferably, weighting factors are not used in determining the minmax score for a particular probe. However, in embodiments where relative abundances of the polynucleotide sequences in the sample are known or can be estimated, the calculated cross-hybridization energy of each homologous sequence to the probe can be multiplied by a weighting factor that is proportional to the homologous sequence's actual or estimated abundance in the sample. The product of the calculated cross-hybridization energy and the weighting factor is then used to determine the minmax score. Alternatively, in cases when limited abundance information is available the abundances of nontarget polynucleotide sequences under consideration can be classified into a limited number of abundance categories (e.g., high and low), and a simplified set of weighting factors can be used for each category (e.g., 1 and 0 or, alternatively, 10 and 1 for "high" and "low," respectively).

Figure 5A:
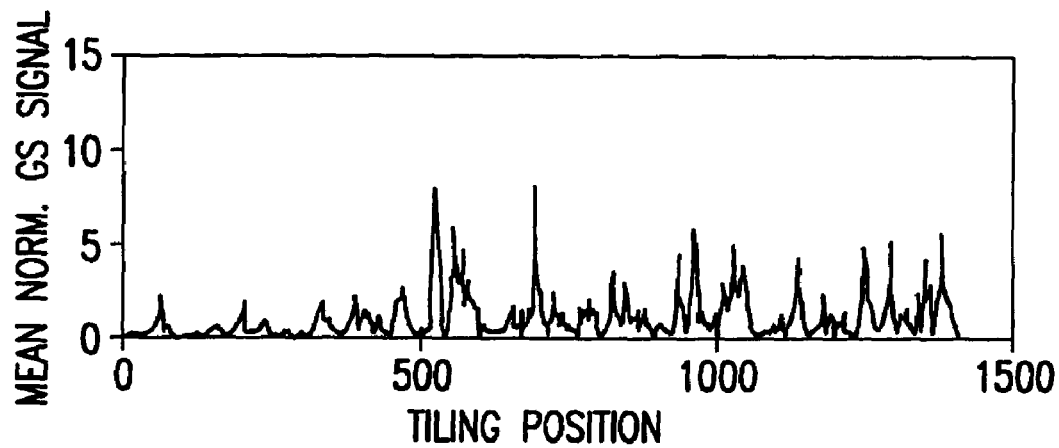
Figure 5B:
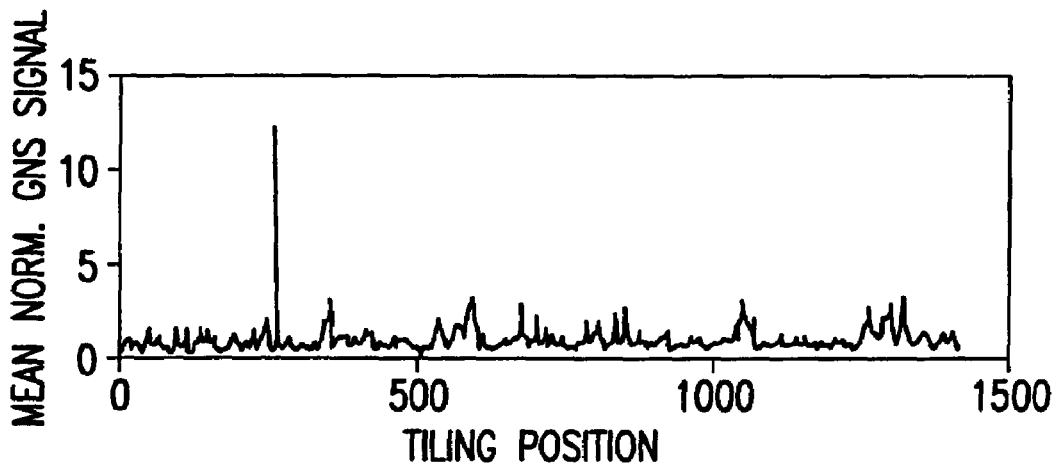
Figure 5C:
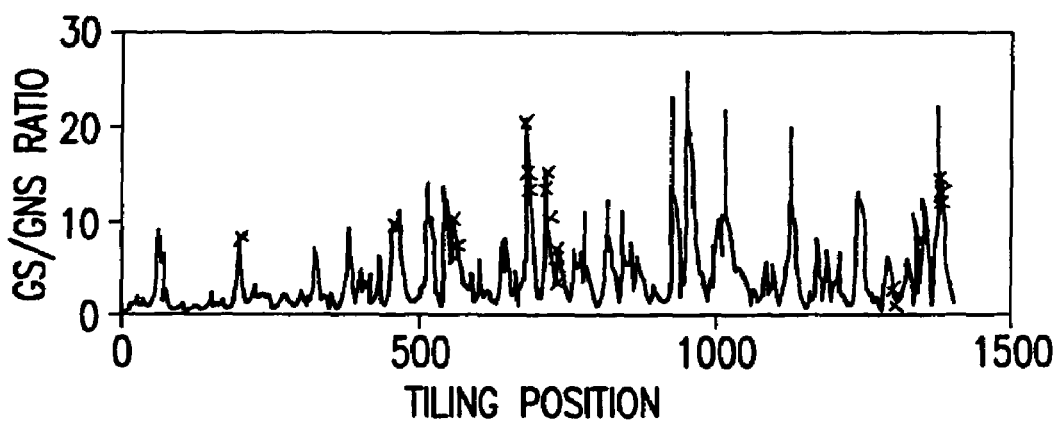
Figure 6A:
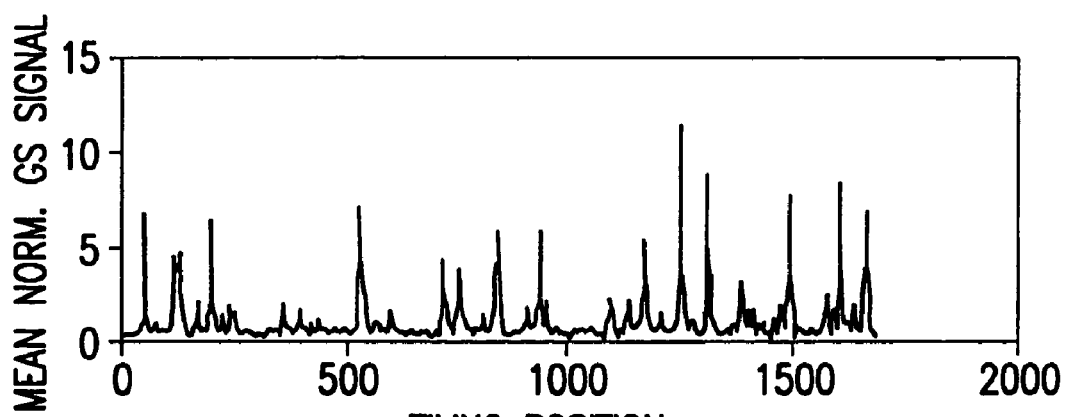
Figure 6B:
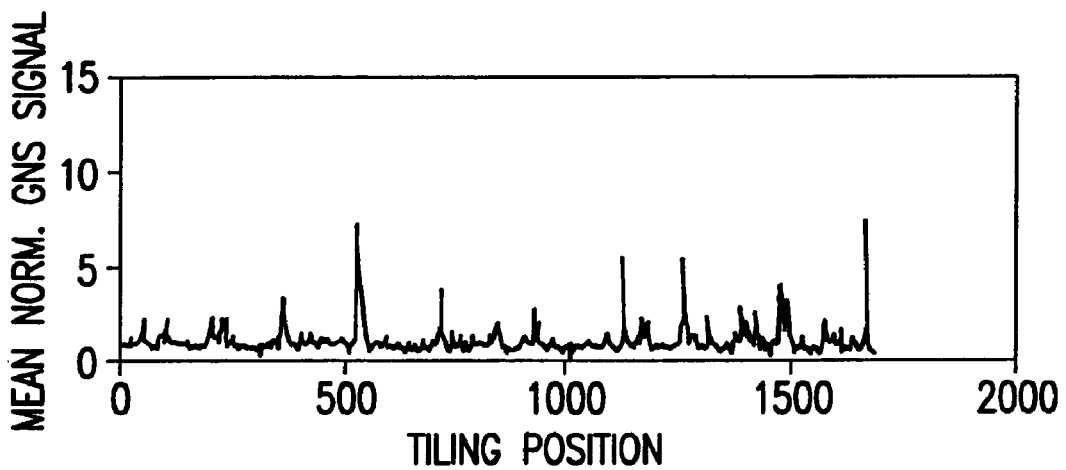
Figure 6C:
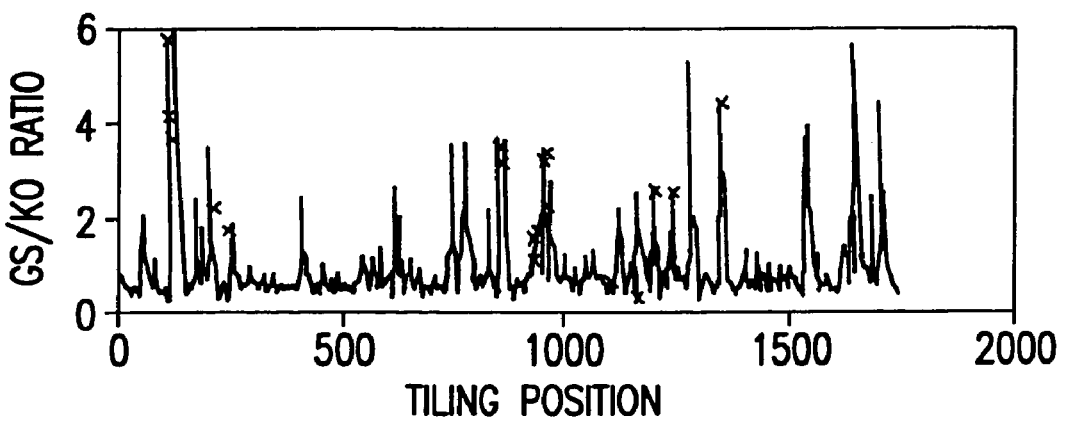

The sensitivity and/or specificity of a particular probe may also be determined experimentally, e.g., using differentially labeled polynucleotide samples. For example, FIGS. 5A and 5B show observed target and non-target hybridization, respectively, to oligonucleotide (25-mer) probes that match different positions along the known *S. cerevisiae* gene YER019W (GenBank Accession No. U18778). FIGS. 6A and 6B show observed target and non-target hybridization, respectively, to oligonucleotide probes that match different positions along the known *S. cerevisiae* gene HXT3 (Ko, C. H. et al., 1993, *Mol. Cell. Biol.* 13:638–648; GenBank Accession No. L07080). The ratios of target to non-target hybridization for probes matched to YER019W and HXT3 are shown in FIGS. 5C and 6C, respectively. Specifically, the data for each figure were obtained by hybridization of two differently-labeled samples to the same oligonucleotide array in accordance with the methods described in copending provisional U.S. Patent Application Ser. No. 60/154,563, filed Sep. 17, 1999. One sample contained only target sequences whereas the other sample was derived from a yeast strain in which the target gene (YER019W or HXT3) was deleted and so represents actual cross-hybridization from the remainder of the genome.

Probe Size and Length:

The present inventors have discovered that both the sensitivity and specificity of oligonucleotide probes increase with oligonucleotide length (i.e., with the number of nucleotide bases in the probe). Thus, oligonucleotide probes can also be ranked and/or selected in the methods and compositions of the present invention according to their size or length.

The probes of the present invention are preferably selected to be at least 15 bases in length, and are more preferably at least 20 bases in length, more preferably at least 30 bases in length, more preferably at least 40 bases in length, more preferably at least 50 bases in length or more preferably 60 bases in length.

Typically, synthetic nucleotide probe sequences (e.g., oligonucleotide sequences) are shorter than 500 bases in length, and are more typically shorter than 100 bases in length. Preferably, the probe lengths selected are short enough that synthesis of pure (i.e., sufficiently pure for use as probes) full-length sequences is practical using existing techniques (such as N-phosphonate or phosphoramidite chemistry techniques described, e.g., in Froehler et al., 1986, *Nucleic Acid Res.* 14:5399–5407; and in McBride et al., 1983, *Tetrahedron Lett.* 24:246–248). Thus, in preferred embodiments, the oligonucleotide probes selected are 100 or fewer bases in length and are more preferably 90 or fewer bases in length, more preferably 80 or fewer bases in length, more preferably 70 or fewer bases in length or more preferably 60 or fewer bases in length. Thus, in a most preferred embodiment, the probe nucleotide sequences of the present invention are 40–70 or 50–60 nucleotides in length.

Base Composition:

The methods and compositions of the present invention can also be used to rank and/or select oligonucleotide probes according to their base composition. "Base composition", as the term is used herein, is understood to refer to the amount or number of nucleotide bases having a particular chemical identity. Thus, for example, oligonucleotide probes can be ranked and/or selected in the methods of the present invention on the basis of the percentage or fraction of bases that are cytosine ("C"), guanine ("G"), thymine ("T"), adenine ("A") or, in embodiments where RNA probes are used, uracil ("U").

Oligonucleotide probes can also be ranked or selected in the methods of the present invention based on any mathematical combination of two or more nucleotide identities. For example, and not by way of limitation, probes can be ranked and/or selected based on the percentage or fraction of bases that are either guanine or cytosine ("G+C %") or, alternatively, based on the percentage or fraction of bases that are either adenine or thymine ("A+T"). In another embodiment, oligonucleotide probes can be ranked or selected according to a differential between the percent or fraction of two or more nucleotide identities, such as the difference between the percent or fraction of bases in a probe that are adenine and the percent or fraction of bases that are cytosine ("A<C %").

In preferred embodiments, oligonucleotide probes are ranked and/or selected to minimize the number of G and C bases. In particular, it is already well known in the art that guanine-cytosine base pairs have a higher stability than do adenine-thymine base pairs and, further, that many guanine containing mismatches have a higher stability than do non-guanine containing mismatches (see, e.g., SantaLucia, 1998, *Proc. Natl. Acad. Sci. U.S.A.* 95:1460–1465). As a result, although the percentage of guanine-cytosine base pairs is therefore somewhat correlated with the perfect match duplex binding energy discussed above, high number of guanine-cytosine base pairs are also correlated with higher levels of cross-hybridization. Thus, probe sequences with a low ratio of G–C base pairs (i.e., a low G+C %) are preferred. Preferably the percentage of G–C base pairs is between 0 and 75%, more preferably between 0 and 55%, and still more preferably between 8 and 45%.

For example, FIG. 16 shows a plot of differential expression (vertical axis) of the gene ETR103 (GenBank Accession No. M62829) in unactivated and activated human lymphoblast cells as reported by several candidate oligonucleotide probes. The fraction of guanine and cytosine bases in the probes is indicated on the horizontal axis. Although the difference in the level of ETR103 expression in unactivated and activated human lymphoblasts is known to be very high, only those probes with a G+C % less than 0.4 (i.e., 40%) report at least a two-fold increase of ETR103 in activated lymphoblasts.

Oligonucleotide probes can also be ranked and/or selected by base composition criteria that allow for more efficient synthesis or preparation of the probes. For example and not by way of limitation, in preferred embodiments of the present invention oligonucleotide probes are selected for use on microarrays that are prepared, e.g., by means of an ink jet printing device for oligonucleotide synthesis (see, e.g., the methods and systems described by Blanchard in International Patent Publication No. WO 98/41531, published Sep. 24, 1998; Blanchard, U.S. Pat. No. 5,028,189 issued Feb. 22, 2000; Blanchard et al., 1996, *Biosensors and Bioelectronics* 11:687–690; and Blanchard, 1998, in *Synthetic DNA Arrays in Genetic Engineering*, Vol. 20, J. K. Setlow, Ed., Plenum Press, New York at pages 111–123). In such embodiments, as nozzles in the inkjet mechanism age, their firing accuracy decreases. In a particular embodiment, nozzles in the inkjet mechanism provide tetrazole activator to pairs of phosphoramidites in combination. Thus, cytosine and adenine receive tetrazole activator from one set of such nozzles while guanine and thymine receive tetrazole activator from another set of such nozzles. As a consequence, aging and/or misfiring nozzles can pull all available cytosine and adenine bases to one side of the spot on the microarray wherein the oligonucleotide probe is being synthesized. Consequently, sequences that are substantially richer in either adenine or cytosine can be synthesized with less purity and having low-complexity sequences (e.g., homopolymers of adenine or cytosine) at the fringe of the spot where they are synthesized on the microarray. In such embodiments, therefore, it is preferable to select probes for which the difference in the percentages of adenine and cytosine bases ("A–C %") is very low or zero.

Exemplary, preferred base compositions values are as follows; G+C %: preferably 0–75%, more preferably 0–55%, still more preferably 8–45%; G %: 0–35%; C %: 0–35%; A %: 0–90%; T %: 0–90%; A–C %: −15 to 60%; T–G %: −15 to 60%.

Sequence Complexity and Information Content:

As is readily appreciated by those skilled in the art, oligonucleotide probes that hybridize most specifically to a particular polynucleotide sequence (e.g., the sequence of a particular gene) are, in general, probes that are complementary to unique portions of the polynucleotide sequence that are not found in other polynucleotide sequences (e.g., in other genes) in a given sample. Such sequences are said to have a high information content since they can identify unique polynucleotide sequences in a given sample (for example, a unique gene in the genome of a cell or organism). Conversely, probe sequences said to have low information content are sequences whose complements can be found many times in a sample (e.g., in the genome of a cell or organism) and which do not, therefore, identify a unique polynucleotide such as a unique gene.

Examples of sequences having a low information content include, but are not limited to, repetitive elements, simple repeats, and runs of contiguous repetition or "runs" of one base. Contiguous runs of a single base are referred to in the art as "polyX" runs or "polyX" repeats, wherein "X" denotes the nucleotide base (e.g., adenine, thymine, guanine or cytosine) that is repeated. Such polynucleotide repeats can be "scored" in a probe sequence, e.g., by simply counting the number of nucleotide bases in the single longest continuous run of any one base or, alternatively, by totaling the cumulative length of bases involved in polyX runs in the probe sequences. For example, when target polynucleotide samples are prepared by a method comprising oligo-dT priming of polyA+ mRNA, a high proportion of polyT sequences may be found at the 3' ends of the resulting polynucleotide molecules. Accordingly, in such embodiments it is preferable to select probes having few or no polyA repeats. Probes can therefore be evaluated or scored for polyA repeats (or for continuous runs of any other particular nucleotide base) by counting the number of contiguous adenines (e.g., at the 5' end) and ranking or selecting the probes so that probes having a lower polynucleotide repeat score are preferably selected. polyX runs can be as short as two bases. However, polyX runs that are more than three, four, five or ten bases in length have particularly low information content and are preferably avoided in oligonucleotide probes ranked and/or selected according to the present invention.

"Simple repeats" refer to tandem repeats of short (e.g., 1–5 bases, more typically 1–3 bases) sequences. By contrast, repetitive elements are longer (e.g., between 20 and 90,000 base pairs, more typically about 1,000 base pairs), more complex sequences that are overrepresented in a polynucleotide sample. For example, it is well known in the art that the genomes of many higher organisms, particularly eukaryotes (in particular, higher eukaryotes such as mammals and including humans) contain complex sequences that occur many times and are overrepresented in the genome. Typically, these complex repeated elements are specific to the evolutionary lineage of the cell or organism.

Both simple repeats and more complex repetitive elements can be readily identified and "scored" by the skilled artisan. For example, in a preferred embodiment, the program RepeatMasker (Available Web Site: http://ftp.genome.washington.edu/cgi-bin/RepeatMasker) can be used to compare a polynucleotide sequence of interest (which is usually entered by a user) to sequences of repetitive elements and/or simple repeats in a database of such sequences. Because such repetitive elements and simple repeats are generally specific to the species of organism from which a polynucleotide sample is derived, preferably the database is a database of repetitive elements and/or simple repeats for an appropriate organism or class of organism (e.g., for primates, rodents, mammals, vertebrates, *Arabidopsis*, grasses or *Drosophila*, to name a few). Typically, such a comparison is done using a "scoring matrix" that can be entered or selected by a user or, alternatively, a default scoring matrix used automatically by the program.

In a preferred embodiment, regions of the nucleotide sequence of interest that align with repetitive element and/or with simple repeat sequences within the database are "masked," e.g., by replacing the aligned bases with "N" or "X" in the program output. A skilled artisan can then select oligonucleotide probes with high information content by selecting oligonucleotide sequences that are complementary to portions of the target sequence that are not masked.

Position:

The candidate polynucleotide probes evaluated according to the methods and compositions of the present invention can be complementary to any region of the target polynucleotide sequence of interest (e.g., to any region of a gene sequence of interest). For example, candidate polynucleotide probes having a nucleotide sequence that is complementary to the nucleic acid sequence of a particular target polynucleotide can be selected or provided by a method that is referred to herein as "tiling." Specifically, polynucleotide probes having a nucleotide sequence of length l are selected by selecting probes having a nucleotide sequence complementary to a sequence of l consecutive bases of the target sequence. For example, a polynucleotide probe can be selected or provided by selecting or providing a polynucleotide probe having a nucleotide sequence complementary to l consecutive bases of the target polynucleotide sequence beginning at the i'th base of the target polynucleotide sequence. Thus, a first polynucleotide probe can be selected or provided by selecting or providing a polynucleotide probe whose polynucleotide sequence is complementary to the nucleotide sequence corresponding to bases i through i+l of the target polynucleotide sequence. A second polynucleotide probe sequence can be selected or provided by selecting or providing a polynucleotide probe whose nucleotide sequence is complementary to the nucleotide sequence corresponding to bases (i+n) through (i+n)+l of the target polynucleotide sequence, and so forth.

As noted above, l specifies the length of the probe's polynucleotide sequence. Therefore, l is a positive integer, preferably having a value between 4 and 200, and more preferably having a value between 15 and 150. In embodiments wherein probes having shorter oligonucleotide sequences are used, l is preferably less than 40, more preferably between 15 and 30. Most preferably, however, probes having longer oligonucleotide sequences are used. In such embodiments, l is preferably between 40 and 80, more preferably between 40 and 70, more preferably between 50 and 60.

n, the "tiling interval," is a positive integer that preferably has a value between 1 and about 10. Particularly preferred values of the tiling interval include n=1, 2, 3, 4 and 5. i, which indicates the starting position within the target polynucleotide sequence, is also a positive integer. In certain preferred embodiments, the starting position is at or near the 5'-end of the target polynucleotide sequence. Thus, i has preferred values less than 50 and more preferably less than 10. The first base in the target polynucleotide sequence is a particularly preferred starting position in such embodiments. Accordingly, a particularly preferred value of the starting position is i=1. In other preferred embodiments, only the 3'-end of the target polynucleotide sequence is tiled. For example, in certain embodiments, only the last 2,000, more preferably the last 1,000, more preferably the last 500 and even more preferably the last 350 bases on the 3'-end of the target polynucleotide sequence are tiled. In such embodiments, the value of the starting position i is adjusted accordingly (e.g., i=L−2,000; i=L−1,000; i=L−500; or i=L−350; wherein L is the length of the target polynucleotide sequence).

In most preferred embodiments, the target polynucleotide samples are prepared by amplifying "template" polynucleotide molecules (e.g., mRNA molecules extracted from cells), as described in Section 5.3.4 to produce a sample of cDNA or cRNA molecules. In such preferred embodiments, amplification of the template polynucleotide molecules is generally initiated at one of the two distinct ends of the template polynucleotide molecules: the 5'-end or the 3'-end. Because such amplification techniques are less than 100% efficient, a portion of the sequence of the template polynucleotide molecule that is closer to the end where amplification is initiated is preferentially amplified and is therefore present in the target polynucleotide sample in greater abundance. By contrast, a portion of the sequence of the template polynucleotide molecule that is further from the end where amplification is initiated are less preferably amplified and is therefore present in the target polynucleotide sample in lower abundance and may even be very rare or absent in the target polynucleotide sample.

In preferred embodiments, therefore, candidate probes are ranked and/or selected according to the distance of their complementary region in the target polynucleotide sequence from the preferentially labeled end of the target polynucleotide sequence. Specifically, candidate probes are ranked and/or selected so that those candidate probes corresponding to complementary regions of the target polynucleotide that are near the preferentially labeled end are chosen over candidate probes corresponding to complementary regions of the target polynucleotide that are far from the preferentially labeled end. In one embodiment, for example, oligonucleotide probes are selected for which the first nucleotide base of the corresponding region of the target polynucleotide is within a chosen distance, referred to herein as the "end-distance," from the preferentially labeled end.

The exact end-distance will depend on the specific amplification technique used to generate the target polynucleotide sample. Preferably, the end-distance used is the distance from the end of the target polynucleotide sequence that is amplified with at least 50%, 60%, 70%, 80%, 90%, 95% or 99% efficiency. Appropriate values for the end-distance can be readily determined by the skilled artisan, e.g., using values in the literature for particular amplification techniques used or, alternatively, through routine gel electrophoresis experimentation to determine the length of amplified fragments.

In addition, because both the sensitivity and specificity of probes for a target polynucleotide sequence will typically vary in a continuous manner as one "tiles" through the target polynucleotide sequence as described above, oligonucleotide probes can also be ranked and/or selected on the basis of their overlap with other candidate polynucleotide probe sequences. That is to say, in certain embodiments candidate polynucleotide probes can be ranked and/or selected according to the amount of sequence they share with other candidate polynucleotide probe sequences for the same target polynucleotide.

For example, in one preferred embodiment candidate probes are first ranked according to one or more of the other properties or parameters described herein (e.g., sensitivity, specificity, perfect match binding energy, base composition, position, etc.). The top ranked probe can then be selected and compared to the second ranked probe.

Specifically, the overlap between the two probes can be evaluated, e.g., by comparing the starting position, i, of each probe within the target polynucleotide sequence. If the overlap between the two probes is above a selected threshold (e.g., if the starting positions differ by more than 2 nucleotide bases, more preferably by more than 5, 10, 20, 30, 40, 50 or 60 nucleotide bases) than the second probe is also selected. However, if the overlap between the two probes is equal to or above the selected threshold, the second probe is rejected and the next probe (i.e. the third probe) is selected and its overlap with the first probe is evaluated. This process can be repeated until all of the ranked candidate probes available have been either selected or rejected or, alternatively, until a specified number of probes have been selected. The selected probes can then be employed, e.g., for use on a microarray or, more preferably, can be further screened according to other conditions and criteria discussed above.

5.1.3. Iterative Ranking of Candidate Probes

Candidate probes of the present invention can be ranked according to a variety of ranking systems. Preferably, the systems are based on at least two, and more preferably a plurality of the properties and parameters described in Section 5.1.2, above. For example, in preferred embodiments, candidate probes are ranked according to both the sensitivity and the specificity with which the probe hybridizes to a target polynucleotide sequence (e.g., using a target binding energy score and a non-target binding or cross hybridization energy score). However in more preferred embodiments, the candidate nucleotide probes can, in fact, be ranked and/or selected according to any combination of properties and parameters described hereinabove, including but not limited to: (a) probe size or length; (b) binding energies, including both the perfect match duplex (i.e., of a probe and its target, complementary nucleotide sequence) and cross-hybridization binding energies; (c) base composition, including, for example, the relative amount or percentage of one or more particular nucleotide bases (e.g., adenine, guanine, thymine or cytosine) in a probe sequence, as well as the relative amount or percentage of any combination of such nucleotide bases; (d) the position of a probe's complementary sequence in the sequence of its "target" polynucleotide or gene sequence; and (e) probe sequence complexity, including the presence or lack of common repetitive elements such as polynucleotide repeats (i.e., simple, contiguous repeats of one or more nucleotide bases) as well as more complicated repetitive elements that are well known in the art. Still other exemplary parameters which can be used in the methods and compositions of the invention for ranking and/or selecting oligonucleotide probes include: (f) self dimer binding energy (i.e., the tendency for a particular probe to hybridize to its own sequence); (g) the structure content of the complementary, target polynucleotide sequence for a particular probe (e.g., the presence or absence of certain structural features or motifs); and (h) the information content of a probe's nucleotide sequence. Other properties and parameters known in the art to influence or be predictive of hybridization and cross-hybridization can also be used to rank and/or select candidate nucleotide probes according to the methods of the present invention.

As an example, and not by way of limitation, threshold values (or ranges of acceptable values) can be selected for one, two, three, four or more of the properties described, e.g., in Section 5.1.2, above. Candidate probes can then be selected that have values of those properties that are above (or below) the thresholds or that are within the selected ranges. The selected probes are then ranked according to some other property such as their perfect-match binding energy scores or, alternatively, their cross-hybridization binding energy scores (e.g. the "minmax" score described in Section 5.1.2 above).

Alternatively, candidate probes can be ranked according to each of two, three, four or more selected properties such as the properties described in Section 5.1.2, above. A combined rank can then be determined for each probe that is based, e.g., on the sum of the individual rankings. Such a sum can be, for example, an unweighted arithmetic sum or, alternatively, a weighted arithmetic sum using appropriate weighting factors.

In yet another alternative embodiment, candidate probes can also be ranked by, first, selecting candidate probes that have values of one, two, three, four or more properties (e.g., selected from the properties described in Section 5.1.2) that are each above (or below) a selected threshold or which, alternatively, are within a selected range of values. The selected probes can then be ranked according to each of two, three, four or more selected properties (e.g., from the properties described in Section 5.1.2) and a combined rank, based, e.g., on the sum of the individual rankings, can be determined for each probe.

In more specific, and non-limiting, exemplary embodiments, given the sensitivity and specificity of each candidate probe, the probes may then be ranked according to a variety of ranking systems which will be readily apparent to those skilled in the relevant art. For example, in one preferred embodiment, a threshold sensitivity or perfect-match binding energy is selected, and those probes whose sensitivity or perfect-match binding energy lies above the threshold are ranked according to their specificity, i.e., so that those probes above the threshold having the highest specificity have the highest rank. Alternatively, an interval (i.e., a range) of sensitivity or perfect-match binding energy values can be chosen and probes within that interval can be ranked according to their sensitivity. Conversely, a threshold specificity value (or range of specificity values) may be used and those probes whose specificity lies above that value (or within that range of values) may be ranked according to their sensitivity or according to their binding energies.

In an alternative preferred embodiment, the probes may be ranked twice: once according to their sensitivity (or according to their perfect-match binding energy) and once according to their specificity. A combined rank may then be determined for each probe which is based upon the sum of the sensitivity (or perfect-match binding energy) rank and the specificity rank. In one aspect of this embodiment, the sum of the sensitivity (or perfect-match binding energy) rank and the specificity rank may be a weighted sum, using appropriate weighting constants. One skilled in the relevant art will readily appreciate how to select appropriate values for such weighting constants depending upon the particular circumstances (e.g., the particular polynucleotide molecules to be analyzed and/or their relative abundances).

Figure 7A:
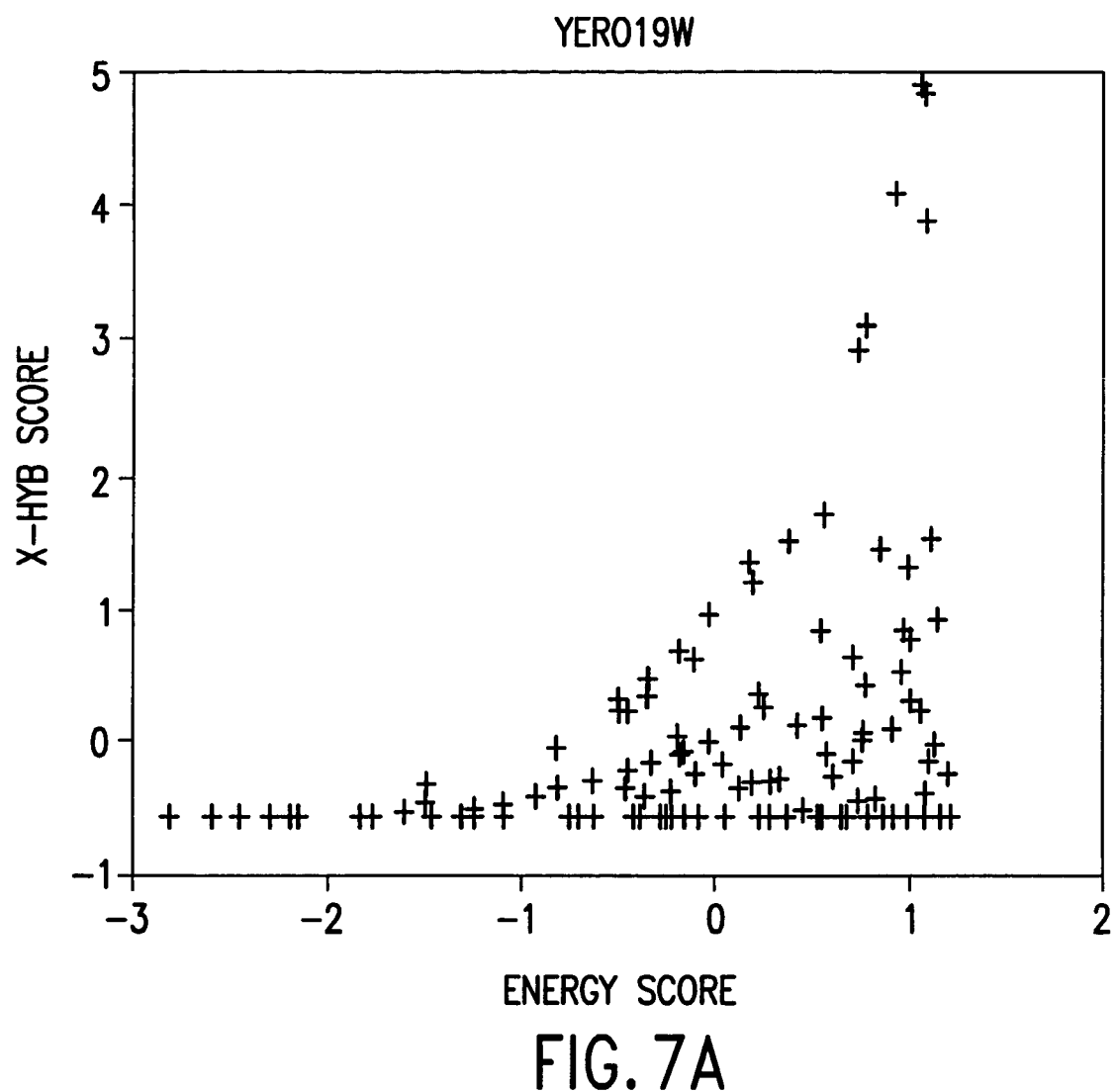
Figure 7B:
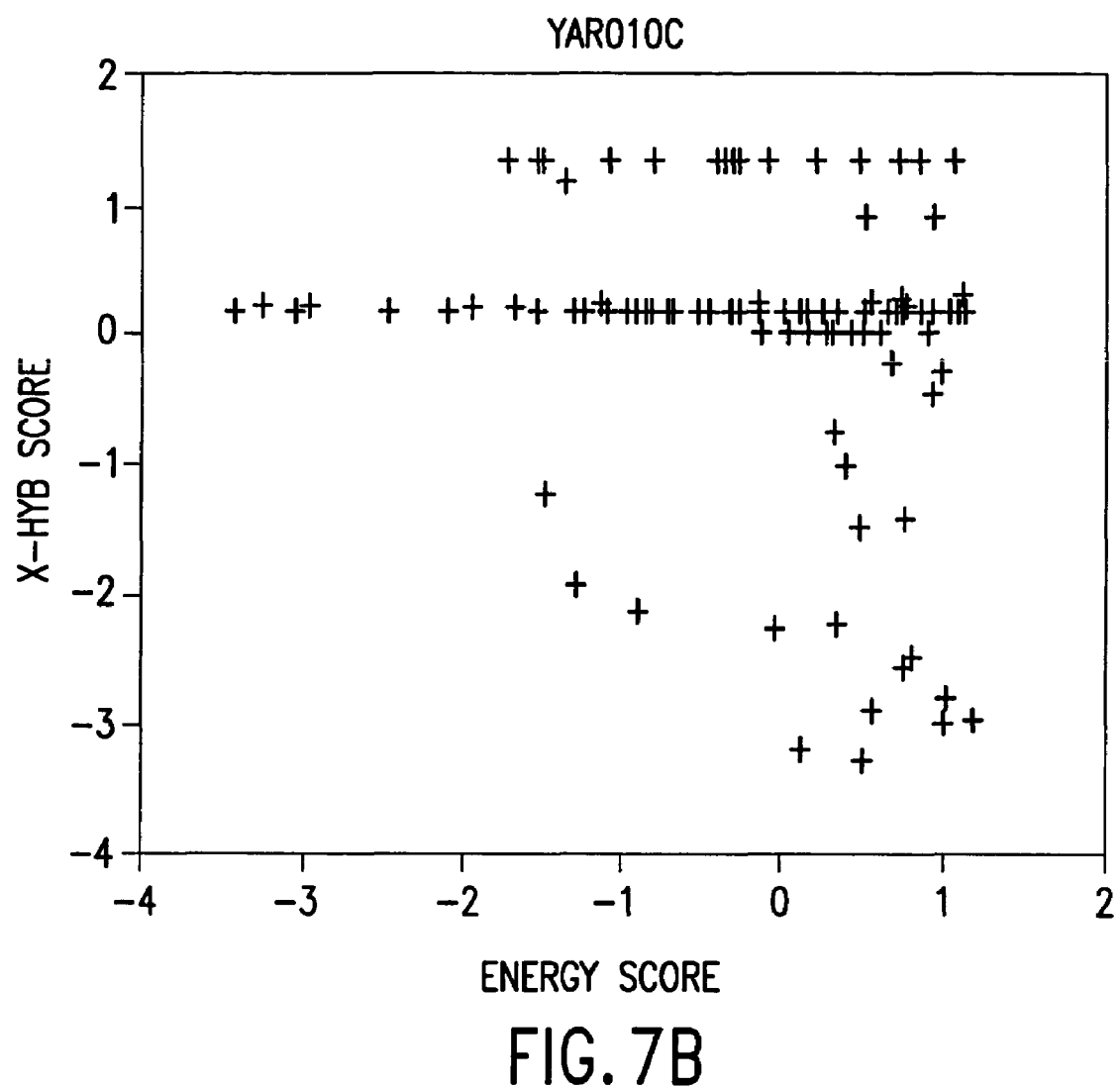

As an exemplary and non-limiting embodiment, FIGS. 7A–B each plot the predicted binding energy score (i.e., the predicted binding energy $\Delta G$) vs. the predicted cross hybridization score (i.e., the predicted value of $X_p/T_p$) for the 10% highest binding energy probes for two *S. cerevisiae* genes: YER019W (FIG. 7A), and YAR010C (FIG. 7B). In particular, the binding energy score was predicted using the nearest-neighbor model (i.e., from Equation 1, above) and the values of $T_p$ and $X_p$ were evaluated from Equations 8 and 9, respectively. SAGE abundance estimates (see, Velculescu et al., 1995, *Science* 270:484–487; and Velculescu et al., 1997, *Cell* 88:243–251) were used to evaluate the abundance term M(c) in Equations 8 and 9. Both the binding energies and the specificity values were normalized to have zero mean and unit variance.

The sensitivity and specificity values of probes for the gene YER019W (FIG. 7A) are typical of those obtained for genes that are fairly unique within a sample, e.g., such as genes that have no close homologs or analogs in the genome of an organism. In particular, probes which have both high binding energy and high specificity can be readily identified, e.g., by visual inspection of FIG. 7A. In such embodiments, ranking systems that select probes having a minimum required specificity (or having a specificity within some range of specificity values) and rank the selected probes according to their sensitivity will be preferred. By contrast, the distribution of sensitivity and specificity values of probes for the gene YAR010C (FIG. 7B) are typical of genes that are members of homology families and to which there are typically similar cross-hybridizing sequences in a sample. In such an embodiment, it is readily difficult to identify probes having both high specificity and high sensitivity by visual inspection of FIG. 7B alone. In embodiments such as this, ranking systems are preferred that select probes having a minimum required sensitivity (or having a sensitivity within some range of sensitivity values) and rank the selected probes according to their specificity.

Figure 8A:
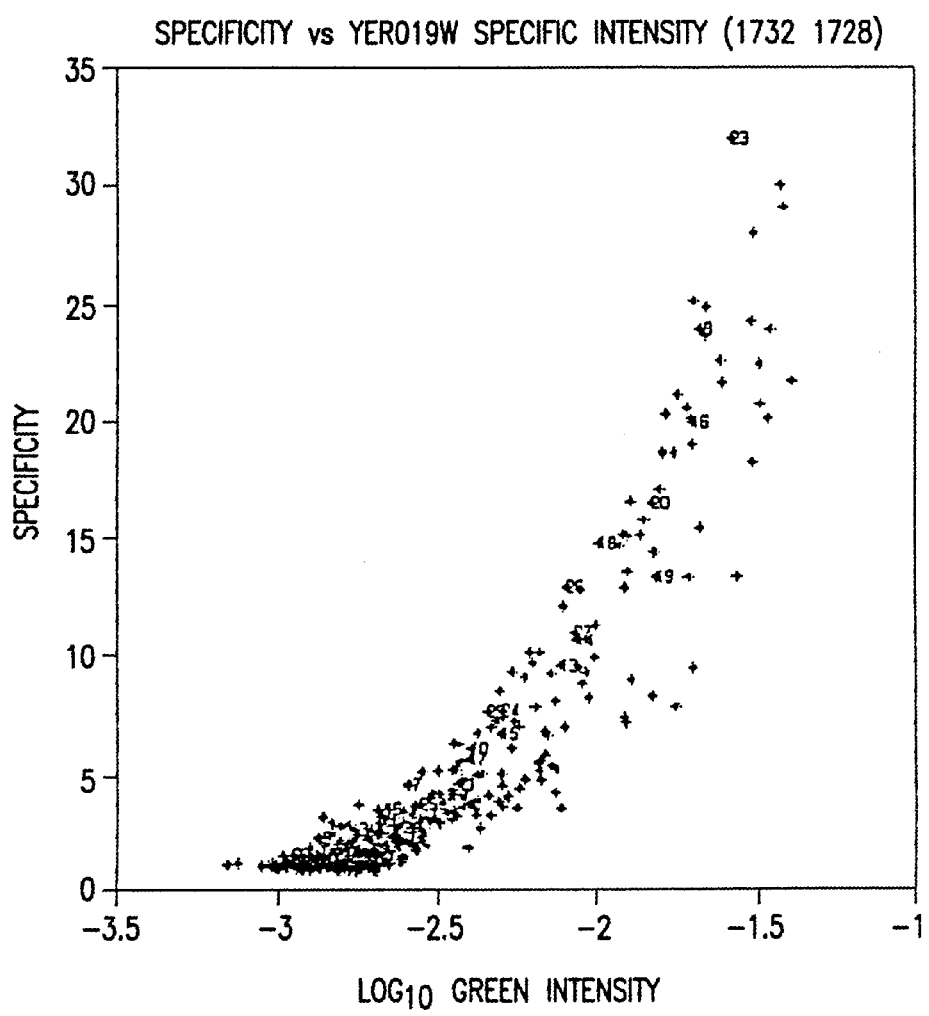
Figure 8B:
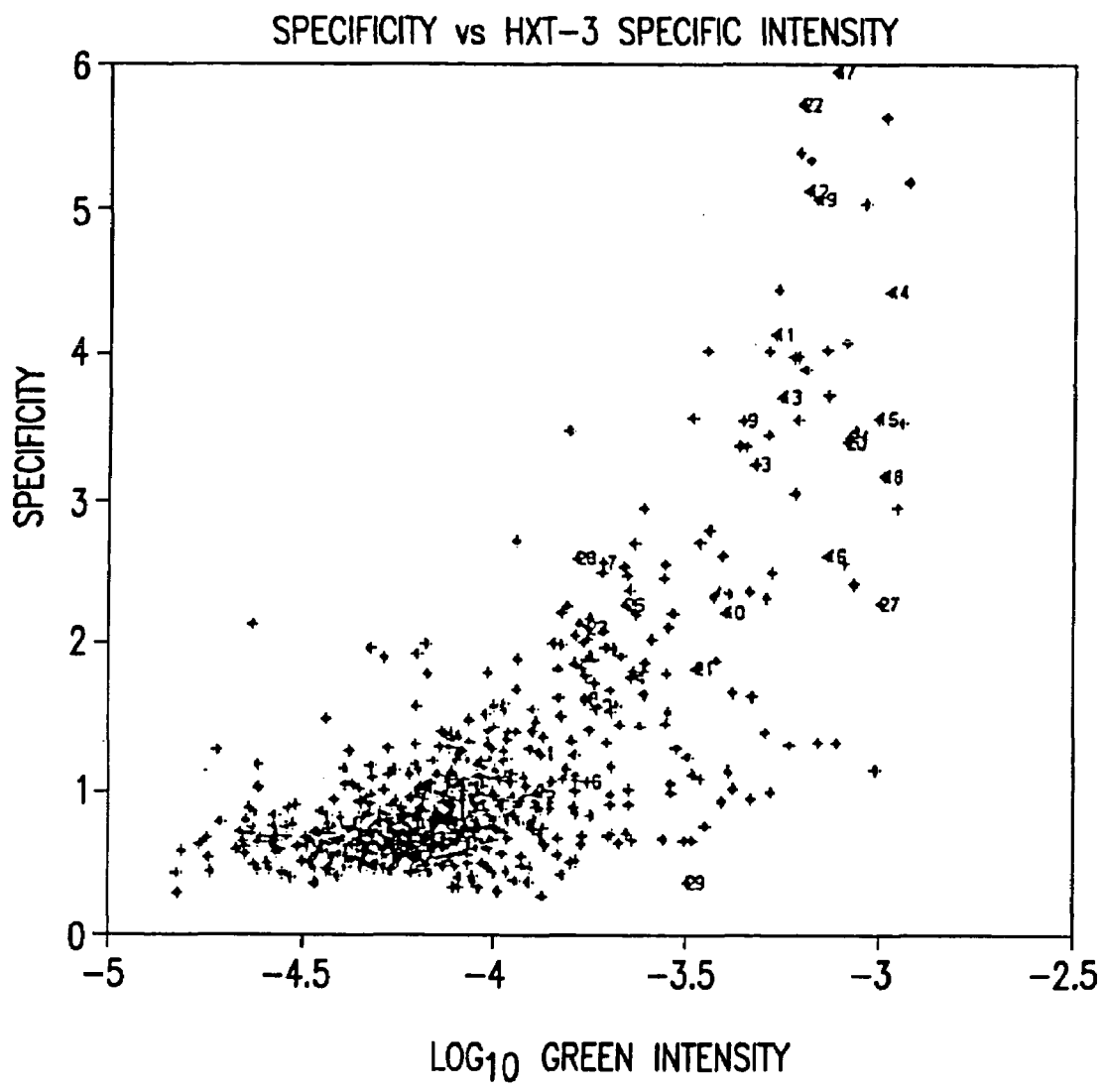

In another exemplary and non-limiting embodiment, the hybridization intensity (i.e., brightness) vs. specificity of the *S. cerevisiae* genes YER019W and HXT3, respectively, are plotted in FIGS. 8A–B using the experimental hybridization data plotted in FIGS. 5 and 6 and discussed above. Those probes which were predicted to rank highest based on the above-discussed ranking functions are indicated in FIGS. 5B and 6B by an (X) symbol. Specifically, the probes were ranked based on a combined ranking function in which both probe specificity and sensitivity were weighted equally. As can be seen in FIGS. 8A–B, the predicted top ranking probes do indeed tend to have higher sensitivity and specificity.

In addition to the analytical ranking systems described above, candidate probes may also be ranked according to empirical, iterative methods. Most preferably, the candidate probes of the invention are ranked according to both analytical and empirical ranking systems and/or methods. In particularly preferred embodiments, candidate oligonucleotide probes are first ranked according to the above-described analytical methods, and such ranking is then empirically refined, at least for the highest ranked probes.

For example, candidate oligonucleotide probes, such as high ranking candidate probes for one or more target polynucleotides, may be empirically ranked by synthesizing one or more microarrays comprising the candidate probes (103) and hybridizing a reference polynucleotide sample thereto (104). Preferably, such hybridization occurs under conditions such as those described in Section 5.1.2, above, so that hybridization intensity (i.e., hybridization signal intensity) correlates with probe specificity. Thus, by empirically selecting for probes with high hybridization intensity (105), the candidate probes are selected for both sensitivity and specificity.

An exemplary and more detailed embodiment of the ranking methods of the invention is shown in FIG. 19. In this particular embodiment, oligonucleotide probes are ranked and (optionally) selected for detecting a particular polynucleotide sequence selected by a user. Usually, the polynucleotide sequence will be the sequence of a gene that is expressed (or suspected of being expressed) by a cell or organism.

Optionally, the complexity or information content of the polynucleotide sequence is first analyzed using a program such a RepeatMasker, described above, to identify portions of the sequence that have low information content such as, but not limited to, portions of the sequence corresponding to repetitive elements or simple repeats. Next, a maximum distance (e.g., a maximum number of nucleotide bases) from the 3'-end of the polynucleotide sequence is selected, and only the portion of the polynucleotide sequence within this selected distance from the 3'-end is further analyzed. Oligonucleotide sequences are then generated, e.g., according to the tiling methods described hereinabove, having a particular sequence length (or, alternatively, a particular range of sequence lengths) that is usually selected by a user.

These oligonucleotide sequences are then evaluated as candidate probe sequences. First, those oligonucleotide sequences corresponding to regions of low information content in the target polynucleotide sequence are removed from consideration. In particular, oligonucleotide sequences that contain, e.g., all or part of a repetitive element or a simple repeat identified by a program such as RepeatMasker are removed. Likewise, oligonucleotide sequences having one or more polyX repeats that are greater than a particular length (e.g. greater than 2, greater than 3, greater than 4, greater than 5, greater than 6, greater than 7, greater than 8, greater than 9, greater than 10, greater than 15 or greater than 20) are removed from consideration. In addition, those oligonucleotide sequences that correspond to unknown or variant sequences of the target polynucleotide sequence (e.g., where one or more allelic variants of the target polynucleotide sequence are known to exist) are also preferably removed from consideration.

The base composition (e.g., G+C %, G %, C %, A %, T %, A–C %, T–G %, etc.) of the candidate sequences is also preferably evaluated. Exemplary, preferred base composition values are as follows; G+C %: preferably 0–75%, more preferably 0–55%, still more preferably 8–45%; G %: 0–35%; C %: 0–35%; A %: 0–90%; T %: 0–90%; A–C %: –15 to 60%; T–G %: –15 to 60%.

The sequences for candidate oligonucleotide probes having been obtained, the perfect-match duplex binding (i.e., hybridization) energy $\Delta G_p$ is than calculated for each candidate oligonucleotide probe p using formulas well known in the art, such as the formulas of the nearest neighbor model and, in particular, Equation 1, above. Optionally, candidate oligonucleotide probes having a calculated value for $\Delta G_p$ that is below a certain threshold or that lies outside a certain range of values are removed from consideration and are not further evaluated. Typically the threshold or range of values will be a range or threshold selected by a user, and one skilled in the art can readily select appropriate values without undue experimentation. Exemplary threshold binding energy values include, e.g., 100, 60 or 23 kcal/mol.

The remaining candidate oligonucleotide probes are then ranked, first according to length (i.e., number of nucleotide bases), and second according to the distance of the probe's nucleotide sequence from the 3'-end of the target polynucleotide sequence. The ranked candidate probes are then "de-overlapped" to select those probes whose sequences overlap the target polynucleotide sequence by no more than a certain number of nucleotide bases selected by the user (e.g, by no more than 2, 5, 10, 30 or 60 nucleotide bases). Such de-overlapping can be performed, e.g., according to the methods described herinabove. Specifically, the top ranked candidate probe can first be selected. The next ranked candidate probe whose sequence overlaps the sequence of the first selected probe by no more than the specified number of bases is also selected, and so forth. Those candidate probes that are not selected are then removed from further consideration.

Preferably, the probe chosen for a given target polynucleotide will, in the worst case scenario, be the probe with the least or least objectionable amount of hybridization with other polynucleotide sequences in a sample. Thus, in preferred embodiments wherein the probes are used to detect expression of particular genetic transcripts from the genome of a cell or organism, the chosen probe will be the probe that hybridizes least favorably (i.e., with the least negative binding energy) to the other sequences in the genome of that cell or organism. Such a probe can be identified, for example, by means of a homology search method such as BLAST (Altschul et al., 1990, J. Mol. Biol. 215:403–410; Altschul, 1997, Nucleic Acids Res. 25:3389–3402; and Zhang and Madden, 1997, Genome Res. 7:649–656). In particular, a BLAST search can be performed against each candidate probe sequence to identify polynucleotide sequences other than the target polynucleotide sequence that are identical or homologous to the probe sequence. For example, sequences that are at least 50%, 60%, 70%, 80%, 90%, 95%, 99% or 100% identical to a candidate probe sequence are identified using a search algorithm such as BLAST. Preferably, the database of sequences used in such an identity or homology search is a database of or containing all or substantially all of the sequence that are present or believed to be present in a polynucleotide sample that the candidate probe or probes are intended to assay. Thus, for example, in embodiments wherein the target polynucleotide is a gene expressed by a particular cell or organism, the database is preferably a database of or containing all or substantially all of the gene sequences expressed by that cell or organism, or a database of all or substantially all of the gene sequences in the genome of that cell or organism. In preferred embodiments, for example, the database may contain at least 50%, at least 60%, at least 70%, at least 80%, at least 90%, at least 95%, at least 99% or 100% of the sequences expressed by the cell or organism. The database can also be a database containing at least 50%, at least 60%, at least 70%, at least 80%, at least 90%, at least 95%, at least 99% or 100% of the gene sequences in the genome of the cell or organism. Publicly available databases of expressed sequences can also be used in such an analysis including, for example, the GenBank or dbEST databases. In addition, because many of the records in such databases are, in fact, duplicate records of the same gene, a cluster filed such as the UniGene cluster file (Schuler, 1997, J. Mol. Med. 75:694–698; Schuler et al., 1996, Science 274:540–546; Boguski & Schuler, 1995, Nature Genetics 10:369–371) can also be used to identify matches to polynucleotide sequence that are, in fact, the target polynucleotide sequence.

Candidate oligonucleotide probes that are found to have 100% sequence identity to a sequence that is not part of the target polynucleotide sequence (i.e., candidate probes that have other perfect-match sequences in the database of expressed sequences) are preferably rejected and eliminated from further analysis or consideration. However, such probes can be used in certain embodiments, e.g., as probes for a family or families of genes whose members share a common sequence or common sequences. For those sequences j in the database that only partially align with the candidate probe sequences (e.g., sequences that are at least 50%, at least 60%, at least 70%, at least 80%, at least 90%, at least 95% or at least 99% identical to a candidate probe sequence), the cross-hybridization binding energy $\Delta G_t$ of these sequences to the candidate probe is also calculated according to the methods described supra for the perfect match binding energy (e.g., using the nearest neighbor model and Equation 1, above). In a particularly preferred embodiment, the most negative cross-hybridization binding energy, which represents a "worst-case" cross-hybridization scenario, is identified and this value is used as the cross-hybridization score for the candidate oligonucleotide probe. In a less preferable embodiment, however, the level of "target" hybridization $T_p$ of the candidate oligonucleotide probe p to the target polynucleotide sequence and the level of cross hybridization $X_p$ of the candidate oligonucleotide probe to non-target sequences (e.g., the sequences identified by BLAST or another sequence homology search algorithm) can be calculated, e.g., according to Equations 8 and 9, above, and used as the cross-hybridization score for the candidate oligonucleotide probe. The remaining candidate oligonucleotide probes can then be re-ranked according to their cross-hybridization scores. Those candidate probes having the the most positive cross-hybridization scores are preferably selected for use, e.g. in the microarrays of the present invention. Preferably, the selected probes are candidate probes that have, not only low cross-hybridization scores, but also have a high perfect-match binding energy.

In preferred embodiments, new microarrays are prepared using the highest ranking probes identified by the above-described methods, and steps 103–105 of FIG. 1 are iteratively repeated to identify those probes with the highest sensitivity and specificity. For example, steps 103–105 of FIG. 1 may be repeated until the number of probes per target polynucleotide has been reduced to some upper limit, e.g., so that the candidate probes for all target polynucleotides may be incorporated on a single microarray (i.e., on a single "chip"). Alternatively, probes may be iteratively ranked according to the above-described methods until some other criteria is satisfied, such as when the selected probes satisfy a minimum (e.g., user determined) required sensitivity and specificity.

In one preferred embodiment, the number of candidate probes for each target polynucleotide is no more than 20, more preferably no more than 10, and more preferably no more than 5, no more than 4, no more than 3, or no more than 2. In particularly preferred embodiments, one candidate probe is identified and/or used for each target polynucleotide.

5.1.4. Screening Chips

The present invention also provides "screening chips" which comprise probes for a large number of different polynucleotides. As used herein, a "chip" comprises a single microarray of polynucleotide probes bound to a solid support. The solid support may be a porous or non-porous support. Microarrays are well known in the art and are described in detail in Section 5.3 below.

In particular, the screening chips of the invention are able to detect, by hybridization, expressed polynucleotide sequences (e.g., mRNA of expressed genes or cDNA derived therefrom) representing the entire genome of a cell or organism. The screening chips of the invention preferably comprise probes that hybridize specifically and distinguishably to at least 50% of the genes in the genome of a cell or organism. More preferably, the screening chips comprise probes that hybridize specifically and distinguishably to at least 75%, at least 80%, at least 85%, at least 90%, at least 95% or at least 99% of the genes in the genome of a cell or organism. In a particularly preferred embodiment, the screening chips comprise probes that hybridize specifically and distinguishably to all (i.e., 100%) of the genes in the genome of a cell or organism In other embodiments, however, the screening chips have probes for those particular genes expressed by a particular cell or cell type of interest. In such embodiments, a screening chip will therefore preferably have probes that hybridize specifically and distinguishably to all of the genes expressed by the cell or cell type of interest, which will often be substantially less than 50% of the genes in the entire genome of the cell or organism (e.g., 20%). The organism may be of any species, including procaryotic organisms, such as *E. coli* and other bacteria, and eukaryotic organisms including, but not limited to, *Saccharomyces cerevisiae*. The organism may also be a higher, multi-cellular organism such as a plant or animal, including a mammalian animal such as a mouse or a human.

In particularly preferred embodiments, the screening chips of the invention include probes for all of the expressed polynucleotide sequences (i.e., for the entire genome) of a cell or organism. In preferred embodiments, therefore, the screening chips contain probes that can hybridize specifically and distinguishably, and can therefore detect, at least about 2000 or at least about 4000 polynucleotide sequences. More preferably, the screening chips contain probes to detect at least about 10,000, at least 15,000, or at least about 20,000 polynucleotide sequences. In particularly preferred embodiments, the screening chips contain probes to detect greater than 80,000, greater than 100,000 or greater than 150,000 polynucleotide sequences.

The screening chips of the invention maximize the number of polynucleotides that may be detected by minimizing the number of probes needed to detect each polynucleotide sequence. In particular, by selecting probe sequences according to the methods and/or having the lengths disclosed hereinabove, the number of probe sequences required to report a particular polynucleotide sequence (e.g., the sequence of a particular gene or gene transcript) may be reduced to as few as one probe sequence. The probe sequences used in the screening chips hybridize specifically and distinguishably to a particular target polynucleotide sequence such as the sequence of a particular gene or gene transcript. Thus, the amount of cross hybridization to other sequences is minimized. In fact, in preferred embodiments the amount of cross hybridization is zero, or is at least negligible. Thus, the amount of hybridization to a particular probe is a reliable indicator of the relative amount of a particular target polynucleotide sequence present in a sample. More specifically, although absolute hybridization intensity values for a target polynucleotide sequence within a sample may vary among different probe sequences, changes (e.g., ratios) of the hybridization levels between perturbed and unperturbed cells (for example, between cells exposed to a drug and cells that are not drug-exposed) are consistent among individual probes. Thus, changes in gene expression can be accurately and reliably measured using a single probe.

Figure 11:
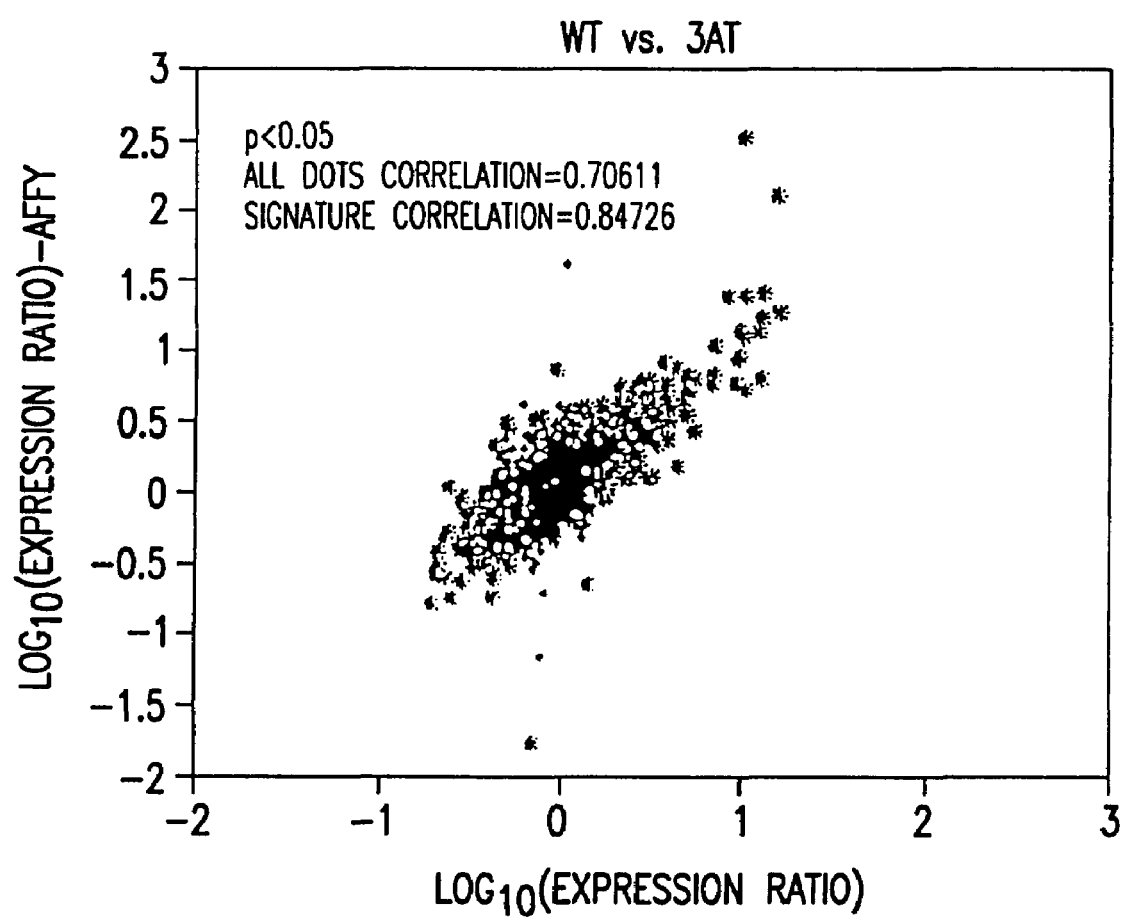
FIG. 11 is a distribution plot comparing expression ratios measured using a screening chip of the invention (horizontal axis) and a standard microarray (vertical axis).

This principle is illustrated by example in FIG. 11 which shows the correlation between data obtained using a screening chip of the present invention and data from a conventional microarray. Specifically, otherwise identical cultures of *S. cerevisiae* were left untreated or were treated with 10 mM 3-amino-1,2,4-triazole(3-AT). The poly A+ fraction of total cellular RNA from each culture was isolated and amplified by in vitro transcription ("IVT") as described by van Gelder et al. (U.S. Pat. No. 5,716,785). IVT products from the drug-treated cell culture were labeled with Cy5, whereas those from the untreated cell culture were labeled with Cy3 according to standard protocols. The labeled samples were hybridized to a screening chip, prepared according to the above-described methods, comprising a single oligonucleotide probe sequence specific for each gene in the yeast genome. Labeled samples were also hybridized, in parallel, to a conventional microarray (a Y36100 Set GeneChip® Yeast Expression Analysis Product from Affymetrix, Santa Clara, Calif.) which comprised 40 oligonucleotide probe sequences for each gene of the yeast genome (20 match sequence probes and 20 mismatch sequence probes). Each of the hybridized chips was scanned using a laser confocal scanner or an Affymetric GeneChip® instrument system, respectively. A distribution plot of the hybridization ratio between treated and untreated cells is shown in FIG. 11. Specifically, the plot compares the expression ratios measured with the screening chip (horizontal axis) and the conventional microarray (vertical axis). The high correlation coefficient r=0.85) obtained demonstrates that the observed expression ratios are very similar for both data sets.

Figure 12:
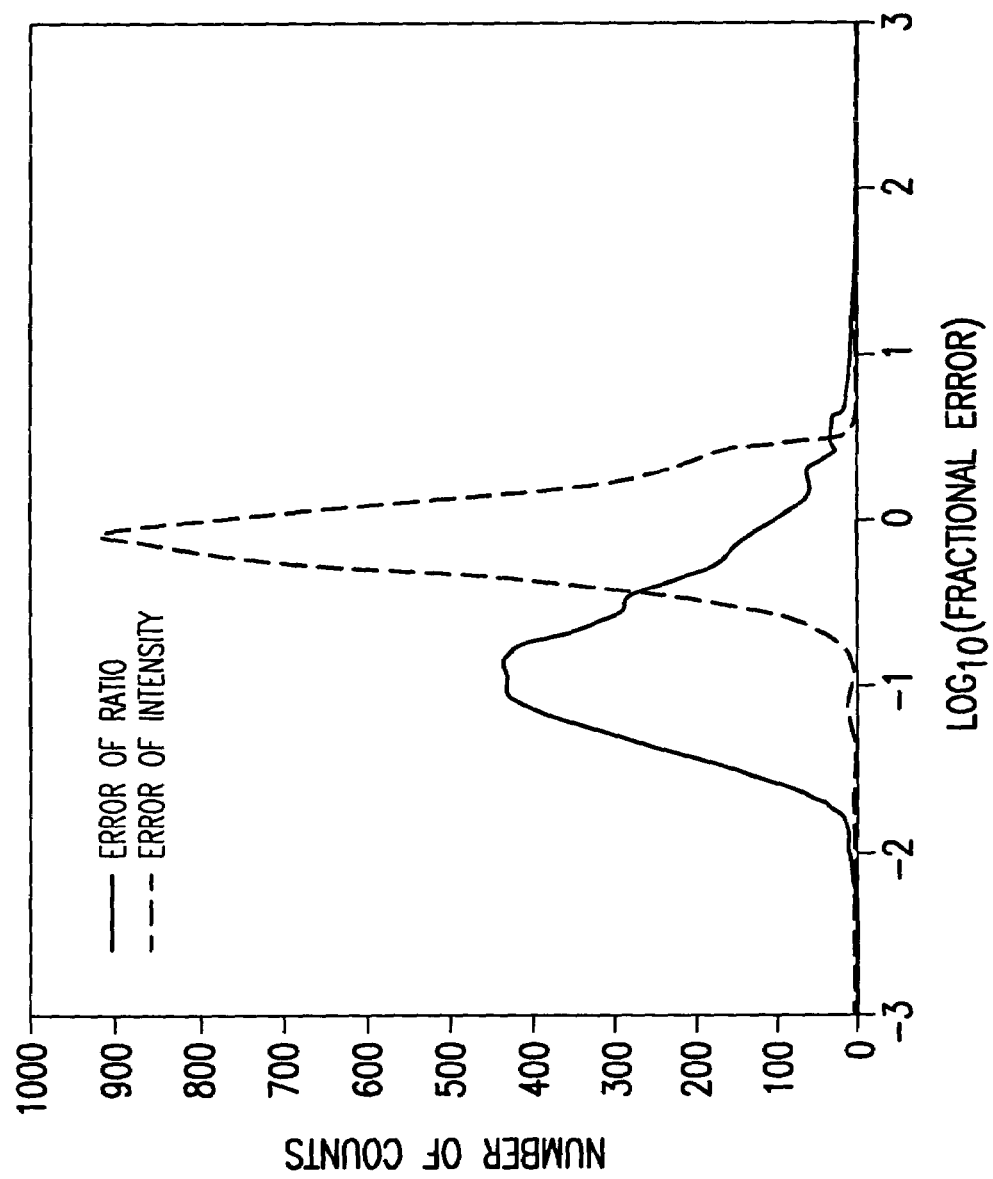
FIG. 12 shows a histogram of the distribution of fractional errors for the absolute hybridization intensities (dashed line) and expression ratios (solid line) from hybridization data measured using a screening chip of the invention.

FIG. 12 shows exemplary data demonstrating the measured expression ratios are consistent among different probes even though absolute intensities of hybridization measured for each probe may vary. In particular, cultures of a wild-type strain of S. cerevisiae and a strain having a homozygous diploid deletion mutation in the pep12 gene were harvested and RNA was isolated and amplified and labeled with Cy3 (wild type) and Cy5 (pep12 deletion) according to the above described methods, and hybridized to a screening chip comprising nine different oligonucleotide probe sequences for each gene of the S. cerevisiae genome. The average and standard deviation of intensities and expression ratios for the probe sequences for each gene were determined and a fractional error (standard deviation divided by the mean) calculated. FIG. 12 shows a histogram of the distribution of fractional errors for the absolute hybridization intensities (dashed line) and expression ratios (solid line) from this data. Fractional errors of absolute hybridization intensities were greater than fractional errors of expression ratios, as can be seen in FIG. 12, suggesting that a single oligonucleotide probe sequence can be used to accurately report changes in gene expression.

In preferred embodiments, the screening chips contain no more than 10 probes for each target polynucleotide sequence. More preferably, the screening chips contain no more than 5, no more than 4, no more than 3, or no more than 2 probes for each target polynucleotide sequence. Most preferably, the screening chips contain only one probe for each target polynucleotide sequence. Accordingly, the probes used in the screening chips must be optimized for sensitivity and specificity, and are thus most preferably selected according to the methods described above in Sections 5.1.1–5.1.3.

The screening chips of the invention are particularly useful for identifying "signature genes" of a cell or organism, i.e.; genes whose expression changes in response to particular changes or perturbations to that cell or organism. Screening chips can therefore be used, e.g., to identify the genes of a cell or organism whose expression is up-regulated or down-regulated, e.g., as a result of exposure to one or more drugs or to a particular class or family of drugs, as a result of a mutation and/or a change in the expression of one or more other genes (e.g., using a controllable promoter such as a titratable promoter), or as a result of changes in the cell or organism's environment including changes in temperature, exposure to moderate doses of radiation and changes in the nutritional environment, such as the presence or absence of certain sugars or amino acid residues, to name a few.

The identification of such signature genes is therefore useful in a variety of applications and methods for characterizing cells and organisms, including testing biological network models (see, in particular, U.S. patent application Ser. No. 09/099,722 filed on Jun. 19, 1998), identifying pathways of drug action (U.S. patent application Ser. No. 09/074,983 filed on May 8, 1998), drug screening methods (see, e.g., Inernational Patent Publication WO 98/38329, published Sep. 3, 1998), determining protein activity levels (U.S. patent application Ser. No. 09/303,082 filed on Apr. 30, 1999), monitoring disease states and therapies (U.S. patent application Ser. No. 09/334,328 filed on Jun. 16, 1999) including determining the therapeutic index of a drug (U.S. patent application Ser. No. 09/222,582 filed on Dec. 28, 1998), and identifying drug targets (U.S. patent application Ser. No. 09/159,352 filed on Sep. 23, 1998) to name a few.

The screening chips of the invention can also be used, e.g., to identify signature genes that correspond to one or more co-varying sets of genes or gene transcripts. That is to say, the screening chips can be used to identify sets of genes or gene transcripts which change together, e.g., by increasing or decreasing their abundances and/or activities, under some set of conditions. Such co-varying genes and gene transcripts include genes and/or gene transcripts that are co-regulated including, for example, genes or gene transcripts that share one or more regulatory elements such as common regulatory sequence patterns. For a detailed description of co-regulated and co-varying gene sets, including methods for identifying co-regulated and co-regulated genesets, see, e.g., U.S. patent application Ser. No. 09/179,569 by Friend and Stoughton, filed on Oct. 27, 1998; U.S. patent application Ser. No. 09/220,275 by Friend et al. filed on Dec. 23, 1998; and U.S. patent application Ser. No. 09/220,142 by Friend et al. filed on Dec. 23, 1998.

Methods for measuring hybridization of polynucleotides to a microarray, which are particularly suitable for identifying signature genes in the methods of the present invention, are also provided below in Section 5.3.6.

5.1.5. Signature Genes and Chips

Figure 9:
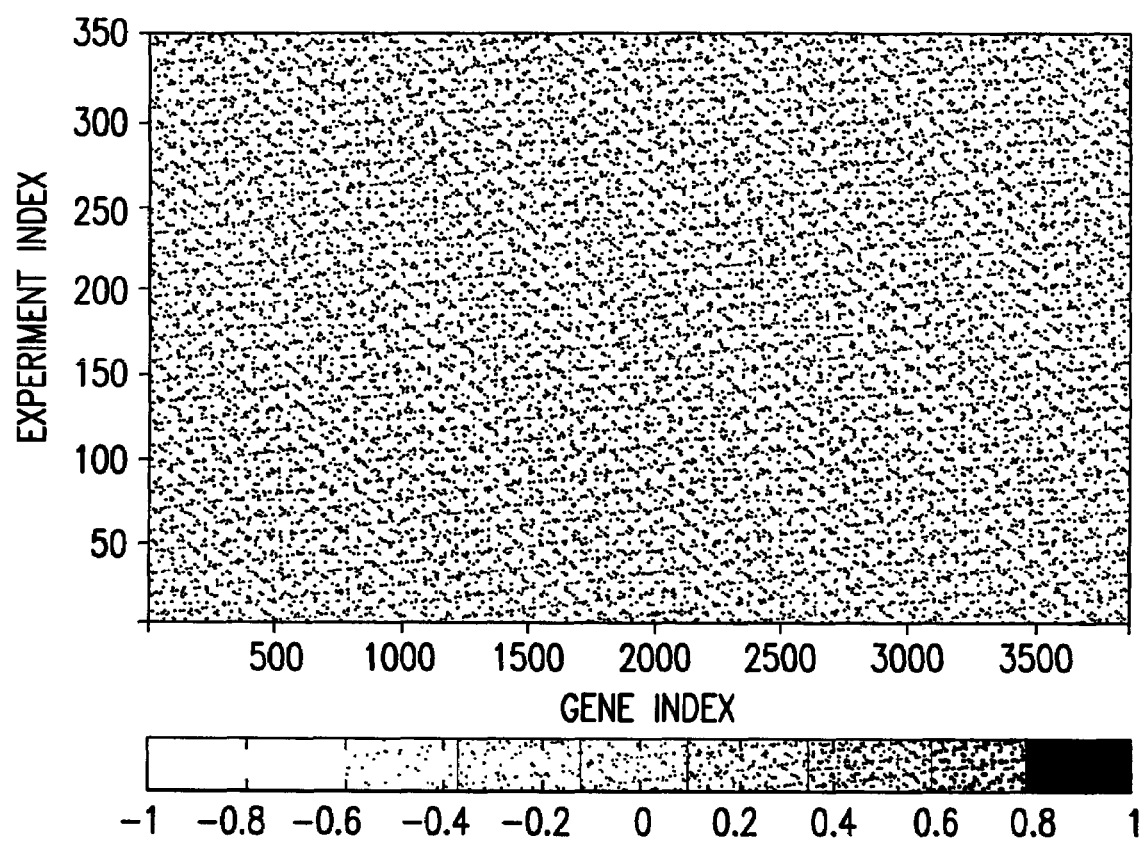
FIG. 9 is a representation of changes in abundances of 4,000 gene transcripts of S. cerevisiae as a result of 350 different changes or perturbations to cells.

As noted above, the methods and compositions of the present invention are particularly useful, e.g., for identifying "signature genes" of a cell or organism; i.e., genes whose expression changes in response to particular changes or perturbations to that cell or organism. In particular, although the screening chips may confer up to $~10^5$ genetic transcripts, in most instances the expression levels of a large part or even a majority of these constituents will not change significantly in response to a particular change or perturbation to the cell or organism, or the change may be small and dominated by experimental error. This point is illustrated, by example, in FIG. 9 which provides a representation of the changes in abundances of 4000 genes as a result of each of 350 different changes or perturbations to cells of S. cerevisiae. Grey indicates no measurable change in the abundance of a gene transcript, whereas black and white indicate an increase or decrease, respectfully, in the abundance of a particular gene transcript, indicated by the "gene index," in response to a particular change or perturbation, which is indicated by the "experiment index." It is generally unhelpful and cumbersome to use these transcripts for most applications, including the applications recited in Section 5.1.4 above. Preferably, therefore, only those genetic transcripts whose abundances do change significantly in response to changes or perturbations to the cell or organism are examined. Such genetic transcripts are referred to herein as "signature genes."

Signature genes are identified, in the methods of the present invention, as those transcripts whose expression changes beyond a selected threshold. For example, in most embodiments changes in the hybridization between untreated and treated cells are quantified in terms of log expression ratios. Thus, in one embodiment a gene may be identified as part of a signature if its log expression ratio is greater than or equal to a factor of two. Alternatively, if error estimates can be derived for the expression ratios, a confidence or probability value may be assigned to each expression ratio representing the probability that it arose by chance or in the absence of any actual change in expression (see, e.g., U.S. patent application Ser. No. 09/222,596 filed on Dec. 28, 1998) a threshold confidence or probability values, e.g., 95% probability, can be used to define the signature genes.

In those embodiments of the invention wherein signature genes are identified using more than one probe per gene sequence, the hybridization intensities for each probe are preferably combined to generate an estimate of the target gene expression levels and/or changes therein. For example, background additive intensity errors can be estimated and subtracted from the hybridization signal, e.g., using the average of negative control probes as an estimate of the background signal, and the hybridization intensities for the probes for a particular target polynucleotide sequence can be averaged or otherwise combined (e.g., additively) to provide a representation of the target polynucleotide's expression level. In one embodiment, outlier rejection is performed before such averaging or combining to remove those signals that vary by more than a certain threshold a (e.g., by more than two to three standards of deviation from the primary or average value). In another embodiment, which is discussed in detail below, each polynucleotide probe occurs in pairs wherein the second member of each pair is an intentional sequence variant (i.e., a mismatch) of the first member. Accordingly, the hybridization intensity of the second member provides an estimate of the level of cross-hybridization to the first member. Subtracting the hybridization intensity of the second member from the intensity of the first member thus provides a correction for the specific hybridization to the first member, at least to the extent that the mismatch variant truely represents the cross-hybridization level.

Once signature genes have been identified for particular changes or perturbations to a cell or organism, probes for detecting polynucleotide molecules corresponding to the signature genes may be selected (108), e.g., using the ranking and selection methods described in Sections 5.1.2–5.1.3, above, and "signature chips" may be constructed (109) with the selected probes according to standard methods for fabricating microarrays, including the methods described in Section 5.3 below. Such signature chips are therefore also considered part of the present invention.

The signature chips of the invention therefore comprise arrays of polynucleotide probes which are selected according to optimal sensitivity and selectivity for a particular set of signature genes. Because the signature chips of the invention contain probes for detecting fewer target polynucleotide sequences (e.g., for fewer genes or gene transcripts), such chips can accommodate a larger number of probes per target polynucleotide sequence. For example, in preferred embodiments the signature chips of the invention comprise at least five probes specific to each target polynucleotide sequence. More preferably, the signature chips contain at least 10 probes specific to each target polynucleotide sequence or, in certain preferred embodiments, at least 20 probes specific to each target polynucleotide sequence (i.e., for each gene or gene transcript). In other preferred embodiments, the signature chips of the invention contain at least 50, at least 100, at least 150 or at least 200 probes specific to each target polynucleotide sequences. This redundancy among the probes of a signature chip can be used to estimate and subtract contributions to the hybridization intensity signal which are due to cross-hybridization and thereby detected hybridization to a particular target polynucleotide sequence (e.g., to a particular gene) more accurately. Thus, the signature chips of the invention are able to detect the actual level of particular polynucleotide sequences in a sample (e.g., the actual level of expression of particular genes or gene transcripts) more accurately than are screening chips.

In one exemplary but non-limiting embodiment the signature chips comprise both match and mismatch probes for a signature gene. Methods for detecting polynucleotides using systems of matched/mismatched probe pairs are known in the art, and are described, e.g., by Lockhart et al., 1996, Nature Biotechnology 14:1675–1680. Specifically, one probe in each pair of probes is a matched sequence probe that is matched to (i.e., complementary to) and therefore specific for a particular target polynucleotide sequence. The other probe in each pair of probes is an intentional mismatch sequence probe which is not matched or complementary to the target polynucleotide sequence of the matched sequence probe, but which does have the same or about the same melting temperature as the melting temperature of the matched sequence probe (i.e., within 5° C. or, more preferably, within 2° C.). For example, in preferred embodiments, a mismatch sequence probe will have between one and 3 single base mismatches to its target polynucleotide sequence. Specifically, in embodiments wherein shorter oligonucleotide probes are used (e.g., less than or equal to about 30 bases in length) single base mismatches are preferred, whereas double or triple base mismatches are preferred for longer oligonucleotide probes (e.g., 50 to 60 base pairs in length or longer).

Averaged over all possible cross-hybridizing sequences, the mismatch and match probes will each have the same intensity from cross-hybridization. Thus, the difference in signal intensity between the match and intention mismatch probe of a particular pair of probes is, in the mean, the hybridization intensity from specific hybridization of the matched sequence probe to the target polynucleotide sequence.

One skilled in the art will appreciate, however, that the actual distribution of cross-hybridizing sequences in a real sample may, in fact, have more over-all homology for one probe in a match/mismatch pair of polynucleotide probes than for the other probe. As a result, there will still be some random amount of signal due to cross hybridization. Accordingly, in preferred embodiments a plurality of match/mismatch probe pairs are used to detect a single signature gene. As signals from the plurality of match/mismatch probe pairs are combined (e.g., averaged), the contribution of cross-hybridization to the combined signal will decrease as the number of probe pairs increases. In particular, the contribution of cross-hybridization to the combined signal will tend to zero in the limit of a large number of probe pairs. For example, in one preferred embodiments, 20 or more probe pairs are used to detect a single signature gene.

In another, particularly preferred embodiment, set of match/mismatch probe sequences are used. Specifically, each set comprises a match sequence probe for a particular target polynucleotide sequence and a plurality of mismatch sequence probes. For example, in one exemplary embodiment, between 10 and 200 match sequence probes may be used on a signature chip that are specific to a particular target polynucleotide sequence such as the sequence of a particular gene. In such an embodiment, the signature chip may also contain as many as 4 to 20, or more mismatch sequence probes for each match sequence probe on the signature chip.

In another exemplary, but also non-limiting embodiment, a large number of matched (i.e., complementary) probe sequences (e.g., preferably between 5–10 or more probe sequences) may be used to detect each gene rather than matched/mismatched probe pairs. In such an embodiment, the amount of a signature gene present in a sample is preferably determined by selecting the probes with the highest hybridization intensity and combining (e.g., averaging) their signals. For example, signature probes may be selected, e.g., by outlier rejection, whose hybridization intensities vary from the mean hybridization intensity by no more than some threshold (e.g., some multiple of fraction of the standard deviation). In particular, by hybridizing polynucleotides to the signature chips of the present invention under the highly stringent conditions discussed in Section 5.1.1, above, hybridization specificity will, in general, correlate with specificity. Thus, those probes having the highest hybridization intensity will generally be the probes which hybridize most specifically to a target polynucleotide sequence. Thus, the contribution of cross-hybridization to the signal will be minimized. However, the contribution of cross-hybridization to the combined (e.g., averaged) signal will not tend to zero in the limit of a large number of probes. However, this second exemplary embodiment is preferred in instances wherein it is more preferable to have small variance than it is to have small bias in hybridization measurements, whereas the first exemplary embodiment is preferred in instances wherein it is more preferable to have small bias than to have small variance in hybridization measurements. For example, in those embodiments wherein there is a large number (e.g., about ten or more pairs) of probes per signal gene, the unbiased match/mismatch embodiment is generally preferred, whereas in those embodiments wherein there is a relatively small number of probes per signal gene (e.g., less than about fifteen to twenty), the second exemplary embodiment is preferred.

5.2. Analytical Systems

Figure 10:
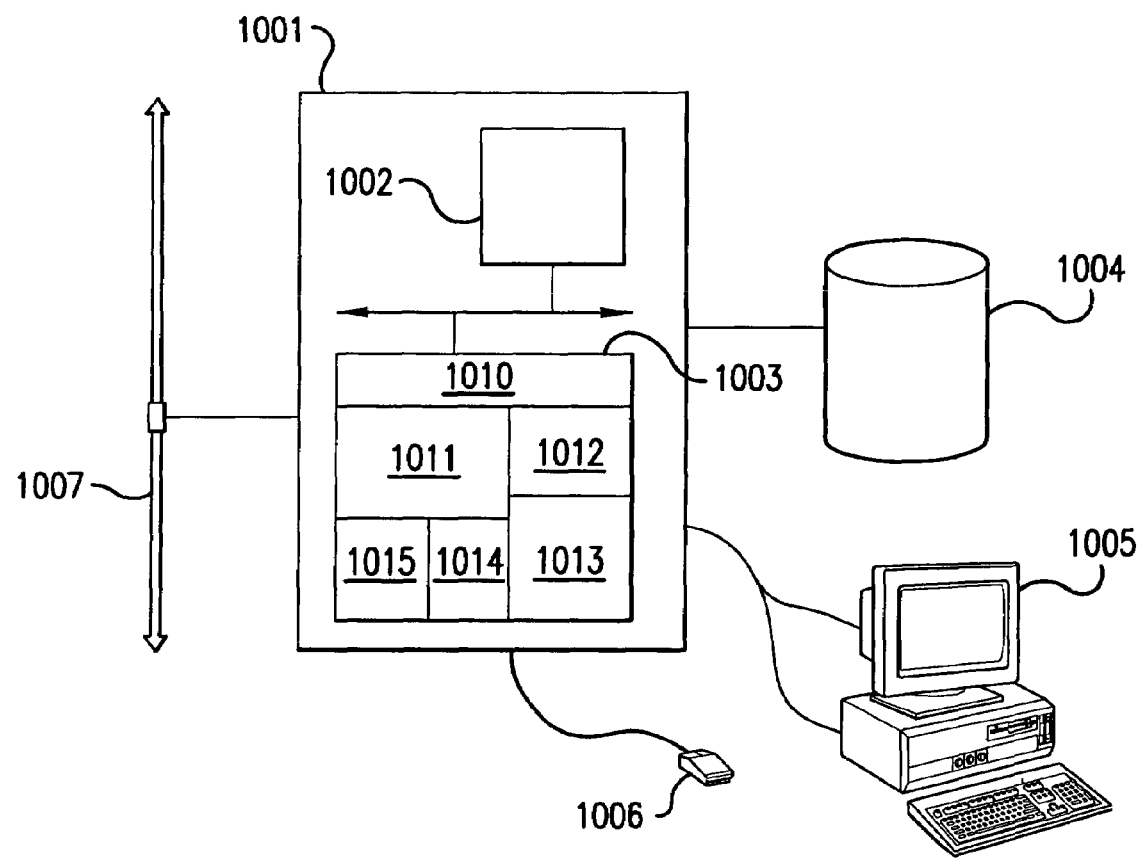
FIG. 10 is a representation of a computer system which may be used to practice the analytical methods of the present invention.

The analytic methods described in Section 5.1 above can preferably be implemented by use of computer systems such as those described herein. FIG. 10 illustrates an exemplary computer system suitable for implementation of the analytic methods of this invention. Computer system 1001 is illustrated as comprising internal components and being linked to external components. The internal components of this computer system include processor element 1002 interconnected with main memory 1003.

It is noted that although the present description and figures refer to an exemplary computer system having a memory unit and a processor unit, the computer systems of the present invention are not limited to those consisting of a single memory unit or a single processor unit. Indeed, computer systems comprising a plurality of processor units and/or a plurality of memory units (e.g., having a plurality of SIMMS or DRAMS) are well known in the art. Indeed, such systems are generally recognized in the art as having improved performance capabilities over computer systems that have only a single processor unit or a single memory unit. For example, in one preferred embodiment, computer system 1001 is an Alta cluster of nine computers; a head "node" and eight sibling "nodes," each having an i686 central processing unit ("CPU"). In addition, the Alta cluster comprises 128 Mb of random access memory ("RAM") on the head node and 256 Mb of RAM on each of the eight sibling nodes. Nevertheless and as the skilled artisan readily appreciate, as such computer systems relate to the present invention, a computer system that has a plurality of memory units and/or a plurality or processor units is, in fact, substantially equivalent to the exemplary computer system depicted in FIG. 10 and having only a single processor and a single memory unit.

The external components include mass storage 1004. This mass storage can be one or more hard disks which are typically packaged together with the processor and memory. Such hard disks are typically of 1 Gb or greater storage capacity and more preferably having at least 6 Gb of storage capacity. For example, in the preferred embodiment described above each node of the Alta cluster comprises a hard drive. Specifically, the head node has a hard drive with 6 Gb of storage capacity whereas each sibling node has a hard drive with 9 Gb of storage capacity. Other external components include user interface device 1005, which can be a monitor and a keyboard together with a pointing device 1006 such as a "mouse" or other graphical input device. Typically, the computer system is also linked to a network link 1007, which can be, e.g., part of an Ethernet link to other local computer systems, remote computer systems, or wide area communication networks such as the Internet. For example, each computer system in the preferred Alta cluster of computers described above is connected via an NFS network. This network link allows the computer systems in the cluster to share data and processing tasks with one another.

Loaded into memory during operation of this system are several software components, which are both standard in the art and special to the instant invention. These software components collectively cause the computer system to function according to the methods of the invention. The software components are typically stored on mass storage 1004. Software component 1010 represents an operating system, which is responsible for managing the computer system and its network interconnections. The operating system can be, for example, of the Microsoft Windows™ family, such as Windows 98, Window 95 or Windows NT. Alternatively, the operating system can be a Macintosh operating system, a UNIX operating system or the LINUX operating system. Software component 1011 represents common languages and functions conveniently present in the system to assist programs implementing the methods specific to the present invention. Languages that can be used to program the analytic methods of the invention include, for example, UNIX or LINUX shell command languages such as C, and C++; PERL; FORTRAN; HTML; and JAVA. The methods of the present invention can also be programmed or modeled in mathematical software packages which allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from Math Soft (Seattle, Wash.). Accordingly, software component 1012 represents analytic methods of the present invention as programmed in a procedural language or symbolic package.

In a preferred embodiment, the computer system contains a software component 1013 which may be software for predicting (i.e., calculating) scores for one or more of the properties or parameters described in Section 5.1.2, above (e.g., base composition, position, perfect-match binding energy and/or cross-hybridization binding energy to name a few) according to the methods described above. Software component 1013 can also contain additional programs, such as RepeatMasker or BLAST, that can also be used in the methods of the present invention to evaluate nucleotide probes, along with appropriate databases of nucleotide sequences for use in conjunction with such programs.

For example the candidate probe sequences may be entered directly by a user (e.g., using a keyboard or some other input device) or may be loaded, e.g., from one or more databases stored on a hard drive, a CD-ROM or some other storage medium, or from other computer systems, e.g., over a the Internet. Alternatively, the computer system may contain additional software components 10014 for generating candidate probe sequences, e.g., by randomly generating sequences of a specified length or, in embodiments wherein candidate probes for a particular target (e.g., for a particular gene or genes) are sought, by generating oligonucleotide sequences, e.g., according to the "tiling" methods described hereinabove, that are complementary to various regions of the target sequences.

The software component 1013 of the computer system also preferably accepts one or more parameters or ranges of parameters for use in selecting nucleotide probes. Exemplary parameters that can be accepted by the software component include: probe length, maximum distance from the 3'-end or 5'-end of the target sequence, the maximum and/or minimum allowable binding energy scores (including perfect-match and/or cross-hybridization binding energies), upper and/or lower limits of acceptable base composition (e.g., G %, C %, A %, T %, G+C %, A–C %), the longest permissible single base run, and the maximum number of base overlap allowed among different probes. The software component can also accept parameters, such as temperature, salt concentration and target polynucleotide concentration, for use in calculating hybridization binding energies. These values can be input, e.g., directly by a user or, alternatively, can be read by the software component from a file.

Next, the user can cause execution of analysis software to calculate one or more parameters or properties for each of the candidate probes. In particular, the software preferably calculates one or more of the particular properties described, e.g., in Section 5.1.2, above, according to the methods and formulas described in that section. For example, and not by way of limitation, the analysis software can cause the processor to calculate, e.g., the predicted sensitivity and specificity of the candidate probes (e.g., according to Equations 8–10, above) or, more preferably, the perfect-match binding energy and the minmax cross-hybridization binding energy for each probe, e.g., using the nearest neighbor model and Equation 1, above. Parameters for use in the nearest neighbor model, particularly the dimer binding energies and initiation parameters, may be entered by a user or loaded, e.g., from a database. Alternatively, the analysis software 1013 may also comprise algorithms for calculating such parameters, e.g., according to Equations 6 or 7 above, and using experimental hybridization data (e.g., hybridization intensities of a test polynucleotide sequence to candidate probe sequences).

Preferably a computer system of the invention also contains an analytical software component 1015 for ranking and/or selecting candidate probes, e.g., for use in screening or signature chips according to the methods described in the above sections. In one preferred embodiment, a computer system may accept data relating to the predicted sensitivities, specificities and other properties (e.g., binding energies, base compositions, etc.) of a plurality of candidate probes and use the data to rank the candidate probes according to the methods described above in Section 5.1.3. These data can be entered directly by a user, loaded from a database or, more preferably determined by a computer system of the invention using an analytical software component 1013 described above.

For example, and not by way of limitation, a computer system may first calculate the sensitivities and specificities of a plurality of candidate probes and then, using the calculated sensitivities and specificities, rank the candidate probes according to the ranking and/or selection algorithms described hereinabove. Alternatively, sensitivities and specificities of a plurality of candidate probes can be calculated by a first computer system, and the results of such calculations can then be transferred, e.g., by a network connection, to a second computer system which ranks and/or selects the candidate probes according to the ranking and/or selection algorithms.

In another preferred embodiment, experimental data describing the sensitivity and specificity of a plurality of candidate probes, such as the experimental data depicted in FIG. 5 or 6, may loaded into a computer, e.g., directly by a user or from a database, and the probes may be ranked according to the above-described ranking and/or selection algorithms.

In a particularly preferred embodiment, the analytical programs of a computer system of the invention cause the processor element to execute the steps of the method depicted in FIG. 19 and described, in detail, in Section 5.1.3, above.

The analytical systems of the invention also include computer program products that contain one or more of the above-described software components such that the software components may be loaded into the main memory of a computer system. Specifically, a computer program product of the invention includes a computer readable storage medium having one or more computer program mechanisms embedded or encoded thereon in a computer readable format. The computer program mechanisms encode, e.g., one or more of the analytical software components described above which can be loaded into the memory of a computer system 1001 and cause the processor of the computer system to execute the analytical methods of the present invention.

The computer program mechanism or mechanisms are preferably stored or encoded on a computer readable storage medium. Exemplary computer readable storage media are discussed above and include, but are not limited to: a hard drive, which may be, e.g., an external or an internal hard drive of a computer system of the invention, or a removable hard drive; a floppy disk; a CD-ROM; or a tape such as a DAT tape. Other computer readable storage media will also be apparent to those skilled in the art that can be used in the computer program mechanisms of the present invention.

Alternative systems and methods for implementing the analytic methods of this invention are intended to be comprehended within the accompanying claims. In particular, the accompanying claims are intended to include alternative program structures for implementing the methods of this invention that will be readily apparent to one of skill in the art.

5.3. Measurement of Hybridization Levels

In general, the hybridization methods of the present invention can be performed using any probe or probes which comprise a polynucleotide sequence and which are immobilized to a solid support or surface. For example, as described supra, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial sequences of genomic DNA, cDNA, or mRNA sequences extracted from cells. The polynucleotide sequences of the probes may also be synthesized nucleotide sequences, such as synthetic oligonucleotide sequences. The probe sequences can be synthesized either enzymatically in vivo, enzymatically in vitro (e.g., by PCR), or non-enzymatically in vitro.

The probe or probes used in the methods of the invention are preferably immobilized to a solid support which may be either porous or non-porous. For example, the probes of the invention may be polynucleotide sequences which are attached to a nitrocellulose or nylon membrane or filter. Such hybridization probes are well known in the art (see, e.g., Sambrook et al., Eds., 1989, *Molecular Cloning: A Laboratory Manual*, 2nd ed., Vol. 1–3, Cold Spring Harbor Laboratory, Cold Spring Harbor, N.Y.). Alternatively, the solid support or surface may be a glass or plastic surface.

5.3.1. Microarrays Generally

In a particularly preferred embodiment, hybridization levels are measured to microarrays of probes consisting of a solid phase on the surface of which are immobilized a population of polynucleotides, such as a population of DNA or DNA mimics, or, alternatively, a population of RNA or RNA mimics. The solid phase may be a nonporous or, optionally, a porous material such as a gel. Microarrays can be employed, e.g., for analyzing the transcriptional state of a cell, such as the transcriptional states of cells exposed to graded levels of a drug of interest, or to graded perturbations to a biological pathway of interest.

In preferred embodiments, a microarray comprises a support or surface with an ordered array of binding (e.g., hybridization) sites or "probes" for products of many of the genes in the genome of a cell or organism, preferably most or almost all of the genes. Preferably the microarrays are addressable arrays, preferably positionally addressable arrays. More specifically, each probe of the array is preferably located at a known, predetermined position on the solid support such that the identity (i.e., the sequence) of each probe can be determined from its position in the array (i.e., on the support or surface). In preferred embodiments, each probe is covalently attached to the solid support at a single site.

Microarrays can be made in a number of ways, of which several are described below. However produced, microarrays share certain characteristics: The arrays are reproducible, allowing multiple copies of a given array to be produced and easily compared with each other. Preferably, microarrays are made from materials that are stable under binding (e.g., nucleic acid hybridization) conditions. The microarrays are preferably small, e.g., between 5 $cm^2$ and 25 $cm^2$, preferably between 12 $cm^2$ and 13 $cm^2$. However, larger arrays are also contemplated and may be preferable, e.g., for use in screening and/or signature chips comprising a very large number of distinct oligonucleotide probe sequences. Preferably, a given binding site or unique set of binding sites in the microarray will specifically bind (e.g., hybridize) to the product of a single gene in a cell (e.g., to a specific mRNA, or to a specific cDNA derived therefrom). However, as discussed supra, in general other, related or similar sequences will cross hybridize to a given binding site. Although there may be more than one physical binding site per specific RNA or DNA, for the sake of clarity the discussion below will assume that there is a single, completely complementary binding site.

The microarrays of the present invention include one or more test probes, each of which has a polynucleotide sequence that is complementary to a subsequence of RNA or DNA to be detected. Each probe preferably has a different nucleic acid sequence, and the position of each probe on the solid surface is preferably known. Indeed, the microarrays are preferably addressable arrays, and more preferably are positionally addressable arrays. Specifically, each probe of the array is preferably located at a known, predetermined position on the solid support such that the identity (i.e., the sequence) of each probe can be determined from its position on the array (i.e., on the support or surface).

Preferably, the density of probes on a microarray is about 100 different probes (i.e., probes of non-identical sequence) per 1 $cm^2$ or higher. More preferably, a microarray of the invention will have at least 550 different probes per 1 $cm^2$, at least 1,000 different probes per 1 $cm^2$, at least 1,500 different probes per 1 $cm^2$ or at least 2,000 different probes per 1 $cm^2$. In a particularly preferred embodiment, the microarray is a high density array, preferably having a density of at least about 2,500 different probes per 1 $cm^2$. The microarrays of the invention therefore preferably contain probes of at least 2,500, at least 5,000, at least 10,000, at least 15,000, at least 20,000, at least 25,000, at least 50,000, at least 55,000, at least 100,000 or at least 150,000 different (i.e., non-identical) sequences.

In one embodiment, the microarray is an array (i.e., a matrix) in which each position represents a discrete binding site for a product encoded by a gene (i.e., an mRNA or a cDNA derived therefrom), and in which binding sites are present for products of most or almost all of the genes in the organism's genome. For example, the binding site can be a DNA or DNA analogue to which a particular RNA can specifically hybridize. The DNA or DNA analogue can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often to at about 75%, more often to at least about 85%, even more often to about 90%, and still more often to at least about 99%. Alternatively, however, "picoarrays" may also be used. Such arrays are microarrays which contain binding sites for products of only a limited number of genes in the target organism's genome. Generally, a picoarray contains binding sites corresponding to fewer than about 50% of the genes in the genome of an organism.

Preferably, the microarray has binding sites for genes relevant to the action of a drug of interest or in a biological pathway of interest. A "gene" is identified as an open reading frame (ORF) which encodes a sequence of preferably at least 50, 75, or 99 amino acids from which a messenger RNA is transcribed in the organism or in some cell in a multicellular organism. The number of genes in a genome can be estimated from the number of mRNAs expressed by the organism, or by extrapolation from a well characterized portion of the genome. When the genome of the organism of interest has been sequenced, the number of ORF's can be determined and mRNA coding regions identified by analysis of the DNA sequence. For example, the genome of *Saccharomyces cerevisiae* has been completely sequenced, and is reported to have approximately 6275 ORFs longer than 99 amino acids. Analysis of these ORFs indicates that there are 5885 ORFs that are likely to encode protein products (Goffeau et al., 1996, *Science* 274:546–567). In contrast, the human genome is estimated to contain approximately $10^5$ genes.

5.3.2. Preparing Probes for Microarrays

As noted above, the "probe" to which a particular polynucleotide molecules specifically hybridizes according to the invention is a complementary polynucleotide sequence. In one embodiment, the probes of the microarray comprise nucleotide sequences greater than about 250 bases in length corresponding to one or more genes or gene fragments. For example, the probes may comprise DNA or DNA "mimics" (e.g., derivatives and analogues) corresponding to at least a portion of each gene in an organism's genome. In another embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of gene segments from genomic DNA, cDNA (e.g., by RT-PCR), or cloned sequences. PCR primers are preferably chosen based on known sequence of the genes or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 50,000 bases, and usually between 300 bases and 1000 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399–5407; McBride et al., 1983, *Tetrahedron Lett.* 24:246–248). Synthetic sequences are typically between about 15 and about 500 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566–568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207–209).

5.3.3. Attaching Probes to the Solid Surface

The probes are attached to a solid support or surface, which may be made, e.g., from glass, plastic (e.g., polypropylene, nylon), polyacrylamide, nitrocellulose, gel, or other porous or nonporous material. A preferred method for attaching the nucleic acids to a surface is by printing on glass plates, as is described generally by Schena et al, 1995, *Science* 270:467–470. This method is especially useful for preparing microarrays of cDNA (See also, DeRisi et al, 1996, *Nature Genetics* 14:457–460; Shalon et al., 1996, *Genome Res.* 6:639–645; and Schena et al., 1995, *Proc. Natl. Acad. Sci. U.S.A.* 93:10539–11286).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767–773; Pease et al., 1994, *Proc. Natl. Acad. Sci. U.S.A.* 91:5022–5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687–690). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids. Res.* 20:1679–1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123. Specifically, the oligonucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes).

5.3.4. Target Polynucleotide Molecules

As described, supra, the polynucleotide molecules which may be analyzed by the present invention may be from any source, including naturally occurring nucleic acid molecules, as well as synthetic nucleic acid molecules. In a preferred embodiment, the polynucleotide molecules analyzed by the invention comprise RNA, including, but by no means limited to, total cellular RNA, poly(A)$^+$ messenger RNA (mRNA), fraction thereof, or RNA transcribed from cDNA (i.e., cRNA; see, e.g., Linsley & Schelter, U.S. patent application Ser. No. 09/411,074, filed Oct. 4, 1999). Methods for preparing total and poly(A)+ RNA are well known in the art, and are described generally, e.g., in Sambrook et al., supra. In one embodiment, RNA is extracted from cells of the various types of interest in this invention using guanidinium thiocyanate lysis followed by CsCl centrifugation (Chirgwin et al., 1979, *Biochemistry* 18:5294–5299). In an alternative embodiment, which is preferred for *S. cerevisiae*, RNA is extracted from cells using phenol and chloroform, as described in Ausubel et al. (Ausubel et al., eds., 1989, *Current Protocols in Molecular Biology*, Vol III, Green Publishing Associates, Inc., John Wiley & Sons, Inc., New York, at pp. 13.12.1–13.12.5). Poly(A)+ RNA can be selected, e.g., by selection with oligo-dT cellulose or, alternatively, by oligo-dT primed reverse transcription of total cellular RNA. Cells of interest include, but are by no means limited to, wild-type cells, drug-exposed wild-type cells, modified cells, diseased cells and, in particular, cancer cells.

In one embodiment, RNA can be fragmented by methods known in the art, e.g., by incubation with $ZnCl_2$, to generate fragments of RNA. In one embodiment, isolated mRNA can be converted to antisense RNA synthesized by in vitro transcription of double-stranded cDNA in the presence of labeled dNTPs (Lockhart et al., 1996, *Nature Biotechnology* 14:1675).

In other embodiments, the polynucleotide molecules to be analyzed may be DNA molecules such as fragmented genomic DNA, first strand cDNA which is reverse transcribed from mRNA, or PCR products of amplified mRNA or cDNA.

5.3.5. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium sarcosine and 30% formamide.

5.3.6 Signal Detection and Data Analysis

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

In preferred embodiments, cDNAs from two different cells are hybridized to the binding sites of the microarray. In the case of drug responses, one cell is exposed to a drug and another cell of the same type is not exposed to the drug. The cDNA derived from each of the two cell types are differently labeled so that they can be distinguished. In one embodiment, for example, cDNA from a cell treated with a drug is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA is thereby detected.

In the example described above, the cDNA from the drug-treated cell will fluoresce green when the fluorophore is stimulated, and the cDNA from the untreated cell will fluoresce red. As a result, when the drug treatment has no effect, either directly or indirectly, on the relative abundance of a particular mRNA in a cell, the mRNA will be equally prevalent in both cells, and, upon reverse transcription, red-labeled and green-labeled cDNA will be equally prevalent. When hybridized to the microarray, the binding site(s) for that species of RNA will emit wavelength characteristic of both fluorophores. In contrast, when the drug-exposed cell is treated with a drug that, directly or indirectly, increases the prevalence of the mRNA in the cell, the ratio of green to red fluorescence will increase. When the drug decreases the mRNA prevalence, the ratio will decrease.

The use of a two-color fluorescence labeling and detection scheme to define alterations in gene expression has been described, e.g., in Shena et al., 1995, *Science* 270:467–470. An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular mRNA in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639–645). In a preferred embodiment, the arrays are scanned with a laser fluorescent scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639–645. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA in two cells or in two cell lines. This can be carried out, as noted above, by calculating the ratio of the emission of the two fluorophores used for differential labeling, or by analogous methods that will be readily apparent to those of skill in the art.

6. EXAMPLE

The following examples are presented as exemplary illustrations of the methods and compositions described hereinabove and are not limiting of that description in any way. In particular, the example presented in Section 6.1, below, describes particular screening chips as well as their use to identify changes in mRNA transcripts in unactivated and activated human lymphocytes, respectively. A comparison of this data with conventional "spotter chips" is also disclosed. Section 6.1 also discloses exemplary signature chips and their use to further analyze changes in signature genes identified using the screening and spotter chips. These data verify that, although the screening chips of the invention may occasionally fail to identify some changes in gene expression, positive results obtained with such chips are indicative of significant changes in gene expression. The chips are therefore useful for screening large numbers of genetic transcripts for changes in expression.

The example presented in Section 6.2 demonstrates the effects of certain other probe design parameters on the reporting properties of candidate oligonucleotide probes. Specifically, the example demonstrates the effects which base composition, information-content and the position of a candidate probe sequence within a target gene sequence have or may have on the reporting properties of a candidate oligonucleotide probe. Thus, these properties are also useful for ranking and/or selecting probes for use, e.g., in the screening chips and signature chips of the present invention.

6.1. Synthesis and Testing of Screening Chips and Signature Chips

Two different types of microarrays or "chips" were used to screen mRNA samples. The first microarray was a screening chip comprising approximately 6,000 different polynucleotide probes that were each 60 bases in length. The polynucleotide sequence of each probe was selected according to the methods described above so that each probe would hybridize sensitively and specifically to a different gene transcript. The probes were synthesized in microarrays using inkjet printing techniques described by Blanchard (see, e.g., International Patent Publication No. WO 98/41531, published Sep. 24, 1998; Blanchard et al., 1996, *Biosensors and Bioelectronics* 11:687–690; Blanchard, 1998, in *Synthetic DNA Arrays in Genetic Engineering*, Vol. 20, J. K. Setlow, Ed., Plenum Press, New York at pages 111–123).

The second microarray, which is referred to herein as a "spotter" chip, was a microarray of probes obtained from fragmented double-stranded cDNA sequences of the same gene transcripts.

Aliquots of the same two RNA samples were hybridized to both types of chips. Specifically, the RNA samples were samples of RNA from unactivated and activated human lymphocyte cells from which mRNA was amplified by PCR, using a primer containing a T7 RNA polymerase promoter, and subsequently transcribed into labeled cRNA (see, U.S. patent application Ser. No. 09/411,074 filed Oct. 4, 1999). A total of 550 genes was identified that changed significantly (P-value<0.01) between the two samples. Significant changes (P-value<0.01) were observed for 164 of these genes on both the screening and spotter chips. However, 237 genes showed significant changes (P-value<0.01) only on the screening chips, and 149 showed significant changes (P-value<0.01) only on the spotter chips.

Signature chips were prepared to examine the behavior of these 550 "signature genes" in more detail. Specifically, the signature chips had, on average, 17 60mer polynucleotide probe sequences for each of the signature genes (standard deviation ±7) which were selected according to the above-described methods of the invention so that each probe would hybridize sensitively and specifically to one of the 550 signature genes. The selected polynucleotide sequences were printed twice on a microarray using the same inkjet printing methods, and the microarrays were hybridized with the same RNA samples as the screening and spotter chips.

FIGS. 14A–C compare the results obtained using the screening and signature chips. Specifically, the figures each show scatter plots of the change in each signature gene from unactivated to activated lymphocytes measured with the signature chip (horizontal axis) and screening chip (vertical axis). FIG. 14A compares the results for the 164 genes that had significant changes on both the screening and spotter chips. The correlation coefficient for the measurements for these particular signature genes obtained using the screening and signature chips was 0.97. FIG. 14B is an identical scatter plot of the 237 genes for which significant changes were observed with the screening chips but not with the spotter chips. The correlation coefficient for the data in this plot is 0.93. Thus, signature genes identified using a single "best" 60mer polynucleotide probe to detect each gene (i.e., on a screening chip) were verified using the signature chips with multiple 60mer polynucleotide probes for each gene. In particular, of the 401 signature genes that were identified on the screening chip, 383 or ~96% were reproducibly detected using the signature chip. Thus, the false positive detection rate of the screening chips was $\leq 4\%$.

A scatter plot comparing the results for the remaining 149 signature genes is shown in FIG. 14C. These signature genes showed significant changes from unactivated to activated lymphocytes on the spotter chips, but not on the screening chips. The correlation coefficient for the changes in expression of these genes measured by the signature and screening chips is only 0.69. Thus, regulation of some genes may not be detected using a single oligonucleotide probe for each gene although it can be detected using multiple oligonucleotide probes per gene. The data from these 149 "false-negatives" was examined more closely by constructing signature plots for each of the 149 signature genes. Specifically, the signature plots compared the log of average intensity of the hybridization signal measured with each probe on the signature chip (horizontal axis) to the log ratio of hybridization intensity between activated and unactivated cells (vertical axis). Exemplary signature plots for four of the 149 gene are shown in FIGS. 15A–D. In each plot, the corresponding probe or probes used on the screening chips are indicated by open circles. In certain cases, however, the exact oligonucleotide used as a probe on the screening chip was not included on the signature chip. Accordingly, open diamonds (e.g., in FIG. 15A) indicate oligonucleotide probes on the signature chip that "bracketed" the probes used on the screening chip and differed from that probe sequence by no more than five bases. The log ratio of the measured signal from the screening chips is indicated in FIGS. 15A–D by a solid line, whereas the log ratio of measured signal from the spotter chips is indicated by a dashed line.

The 149 "false-negative" genes could be generally divided into four classes, with some genes being categorized in more than one class. The first class, depicted in FIG. 15A, was characterized by poor performance of the probe on the screening chip. In particular, although most of the polynucleotide probes on the signature chip exhibited results consistent with those of the spotter chip, the particular probes used for the screening chip did not yield good agreement with the spotter chip. Eighteen of the 149 false-negatives were categorized in this class.

The second class, depicted in FIG. 15B, was characterized by threshold effects. In more detail, the polynucleotide probes used in screening chips to detect genes in this class yielded results that were consistent with results from the polynucleotide probes on the signature chip. However, the fact that these genes are apparently expressed at lower levels made changes in their expression more difficult to detect using 60mer polynucleotide probes. Sixty-six of the false-negative genes belonged to this class.

Polynucleotide probes for genes categorized in the third class (FIG. 15C) did not give a clear consensus for why they gave different results than the spotter chips. Most of the 39 genes categorized in this class also exhibited weak regulation (i.e., <2-fold regulation) on the spotter chips, and therefore may have been misreported by those chips. Finally, for most of the genes categorized in class four (FIG. 15D), the 60mer polynucleotide probes on the signature and screening chips gave different results than probes on the spotter chips. The probes on the spotter chips may have been affected by cross-hybridization and therefore gave inaccurate or misleading results. Thirty genes were categorized in this class.

In conclusion, therefore, of the 149 signature genes that were identified by the spotter chips but not by the screening chips, only 84 of these appear to be true signature genes. Thus the false-negative detection rate of the screening chip appears to have only been about 15% (i.e., 84 false-negatives out of 550 signature genes). 18 of these false-negatives, or ~3%, were apparently caused by selecting the wrong oligonucleotide probe for the screening chip, whereas 66, or ~12%, were because of variable detection or threshold effects.

The data thus demonstrates that the screening chips of this invention can be used, e.g., to screen large numbers of genetic transcripts for changes in expression as a result of a change or perturbation to a cell or organism. The number of both false-positive and false-negative detections are reasonably low, however, the higher rate of false-negative detection suggests that the chips are most preferably used to screen for changes among many transcripts since changes identified by such chips will most likely be significant whereas a failure to detect a change is less certain.

6.2. Testing of Various Probe Design Parameters

This example describes methods and compositions which can be used to assay the effects of various, exemplary oligonucleotide probe parameters on their reporting properties. In particular, the example describes the effects that oligonucleotide base composition, the position of an oligonucleotide probe sequence within a target nucleotide sequence, and sequence information content have on the ability of candidate oligonucleotide probes to reliably detect differential gene expression. The example thus demonstrates that such parameters can be used, e.g., to rank and/or screen candidate probes.

6.2.1. Materials and Methods

Nucleotide sequences representing a plurality of human genes from the NIH UniGene Collection (Available Web Site: http://www.ncbi.nlm.nih.gov/UniGene; see also NCBI News, August 1996, Available Web Site: http://www.ncbi.nlm.nkh.gov/Web/Newsltr/aug96.html; Schuler, 1997, *J. Mol. Med.* 75:694–698; Schuler et al., 1996, *Science* 274: 540–546; Boguski & Schuler, 1995, *Nature Genetics* 10:369–371) were used as sources of oligonucleotide probe sequences for experimental validation of probe design parameters. Multiple 60-mer oligonucleotides were then printed on inkjet chips for each target gene sequence according to the methods described in Section 5.3.3, above, and by Blanchard in International Patent Publication No. WO 98/41531, published Sep. 24, 1998 (see also Blanchard et al., 1996, *Biosensors and Bioelectronics* 11:687–690; and Blanchard, 1998, in *Synthetic DNA Arrays in Genetic Engineering*, Vol. 20, J. K. Setlow, Ed., Plenum Press, New York at pages 111–123 for descriptions of these inkjet printing methods).

Hybridization samples of cRNA were prepared for each assay from total RNA extracted from cells using the method of Linsley and Schelter (U.S. patent application Ser. No. 09/411,074, filed Oct. 4, 1999), and these samples were hybridized to the microarray using conditions and methods described in Section 5.3.5, below. In each assay hybridization levels were measured for each probe using cRNA samples from perturbed and unperturbed cells and the expression ratio of the target gene reported by each probe was evaluated. The expression ratio reported by each oligonucleotide probe was compared to the expected expression change (i.e., the expected expression ratio) of the target gene which had been previously determined, either from cDNA microarray analysis, from the mean behavior of all oligonucleotide probes derived from the target gene sequence or from the literature.

6.2.2. Base Composition

The percentage of guanine (G) and cytosine (C) bases in oligonucleotide probes was compared to expression ratios reported by each probe to evaluate how this parameter (i.e., base composition) effected the probes' reporting properties. Specifically, candidate oligonucleotide probes that are complementary to the human transcription factor ETR103 (GenBank Accession No. M62829) were designed and prepared on microarrays as described hereinabove. cRNA samples from unactivated and activated human lymphoblast cells were prepared and hybridized to the microarrays and the ETR103 expression ration reported by each probe was determined. ETR103 is known to be unexpressed in unactivated lymphoblasts but is highly upregulated in activated lymphoblasts (Shimizu et al., 1992, *J. Biochem.* 111:272–277).

FIG. 16 shows a plot of the ETR103 expression ratio (unactivated lymphoblasts:activated lymphoblasts) reported for each oligonucleotide probe (vertical axis) verses the fraction of G and C bases in the probe (horizontal axis). Inspection of the plot shows that there is a strong negative correlation between G and C content in the oligonucleotide probes and the reliability with which they reported the actual upregulation of ETR103 expression in activated lymphoblasts. Only oligonucleotide probes with a G and C content less than 0.4 (i.e. 40%) reported at least a two-fold increase of ETR103 in activated lymphoblasts.

These data demonstrate, therefore, that the base content of an oligonucleotide probe, such as the relative number of G and C bases, is a parameter which can be used to screen candidate oligonucleotide probes for a target gene. In particular, the data demonstrates that it is preferable to select probes having a relatively low number of G and C bases and, conversely, a relatively high number of adenine (A) and thymine (T) bases.

6.2.3. Target Sequence Position

Microarrays of oligonucleotide probes were also prepared to evaluate how the distance of a probe's complementary sequence from the 3' and 5' ends of its target gene sequence is related to the probe's ability to detect changes in the expression of its target gene. Specifically, "tiling chips" were prepared by selecting oligonucleotide probes complementary to sequences within a target gene that started at every third bases of the target gene. In one particular experiment, described herein in detail, tiling chips were prepared using oligonucleotide sequences complementary to sequences of the target gene AML1b (GenBank Accession No. D43968). cRNA samples were prepared from total RNA extracts from two different human tissue culture cell lines: Jurkat and K562. These cell lines are publicly available from the American Type Culture Collection, (ATCC), 10801 University Boulevard, Manassa, Virgina 20110-2209 (ATCC Accession Nos. TIB-152 and CCL-243, respectively).

AML1b, which is specific to acute myeloid leukemia, is expressed in K562 but not in Jurkat cells (Miyoshi et al., 1995, *Nucleic Acid Res.* 23:2762–2769).

A plot of the expression ratio of AML1b in Jurkat cells: K562 cells reported by each probe (vertical axis) versus the distance of the probe's complementary sequence from the 5' end of the AML1b gene sequence (horizontal axis) is shown in FIG. 17. In general, the reported expression ratios were constant until a threshold distance from the 5' end of the AML1b gene sequence (approximately 4,000 nucleotides) was reached. Probes whose complementary sequences were located at a distance less than about 4,000 nucleotides from the 5' end of the AML1b sequence were effectively unable to detect any change of AML1b expression from Jurkat to K562 cells. This result is due to the fact that the cRNA hybridization samples were prepared by initiating reverse transcription at the 3'-end of the expressed mRNA sequences. However, the generally constant expression ratios shown in FIG. 17 for distances above approximately 4,000 nucleotides from the 5' end are interrupted, at intermittent intervals, by nonspecific oligonucleotide probes within this distance that reported no expression ratio.

Thus, for hybridization samples prepared by reverse transcription initiated at the 3' end of expressed mRNA sequences, oligonucleotide probes used in the compositions and methods of the invention should correspond to complementary sequences of the target gene(s) that are within a certain threshold distance from the 3'end of that target gene's sequence. Preferred, typical threshold distances are generally within 5,000 bases of the 5' end of a target gene sequence, and more preferably within 4,000 bases, within 3,000 bases, within 2,000 bases or, most preferably, within 1,000 bases and still more preferably within 500 of the 3' end of a target gene sequence.

Likewise, and as one skilled in the art readily appreciates, in embodiments of the invention wherein hybridization samples are prepared, e.g., from second strand synthesis initiated at the 5' end of expressed mRNA sequences (for example by SMART RACE), oligonucleotide probes used in the compositions and methods of the invention should correspond to complementary sequences of the target gene(s) that are within a certain threshold distance from the 5'end of that target gene's sequence. Typically threshold distances are generally within 5,000 bases of the 5' end of a target gene sequence, and more preferably within 4,000 bases, within 3,000 bases, within 2,000 bases or within 1,000 bases of the 5' end of a target gene sequence.

6.2.4. Sequence Information Content

Experiments were also performed to evaluate the correlation between the "information content" of an oligonucleotide probe sequence and the specificity with which that probe hybridizes to its target gene sequence. Specifically, the program RepeatMasker (Available Web Site: http://ftp-.genome.washington.edu/cgi-bin/RepeatMasker) was used to identify low information-content sequences in target genes. Such low information-content sequences consist of, e.g., simple repeats of mono to hexanucleotide elements and complex elements found repetitively in the genome. "Tiling chips" were prepared for these target sequences, as described above, and the reported expression ratios of the target genes in different cell types or cell lines were evaluated.

Two particular experiments are described here in detail. In the first experiment, chips were tiled with oligonucleotides complementary to regions of the gene ETR103 (GenBank Accession No. M62829) and were hybridized with cRNA samples prepared from total RNA extracts of activated and unactivated lymphocytes as described in Section 6.2.2, above. The ETR103 gene was also evaluated using Repeat-Masker to identify simple nucleotide repeat elements, such as $(CAG)_n$, $(CGG)_n$ and $(AGGGGG)_n$, within its sequence.

In the second experiment, chips were tiled with oligo-nucleotide complementary to regions of the gene AIM1 (GenBank Accession No. U83115), a gene whose expression is associated with the experimental reversal of tumorgenicity of human malignant melanoma (Ray et al., 1997, $Proc. Natl. Acad. Sci. U.S.A.$ 94:3229–3234) and is expressed in K562 cells but not in Jurkat cells. The AIM1 gene was also evaluated using RepeatMasker, and an ALU complex repetitive element was found within the transcribed portion of this gene.

FIGS. 18A–B show the results from these two experiments. In particular, FIG. 18A is a plot of the reported differential hybridization (vertical axis) verses intensity (horizontal axis) of oligonucleotide probes complementary to the ERT103 gene. Probes that are complementary to regions of the ERT103 gene sequence that were masked by RepeatMasker (i.e., regions containing the repetitive element $(CAG)_n$, $(CGG)_n$ or $(AGGGGG)_n$) are indicated by open circles. FIG. 18B shows a plot of the reported differential hybridization (vertical axis) verses intensity (horizontal axis) of oligonucleotide probes complementary to the AIM1 gene. Probes that are complementary to regions of the AIM1 gene for which greater the 60% of the sequence is contained within the ALU repeat are indicated by open circles.

The results are surprisingly dramatic. FIG. 18A shows that oligonucleotide probes that overlap with simple nucleotide repeats are completely nonspecific and report no differential expression. Likewise, as can be seen in FIG. 18B, overlap of oligonucleotide probes with a complex repetitive element (e.g., the ALU repeat) also decreases the specificity of the probe. However, more than minimal overlap with such a complex repetitive element is required for a complete loss in specificity. Probes for which greater than 60% of the oligonucleotide sequence overlaps with the repetitive element do, however, exhibit a complete loss of specificity. Smaller overlap of probe sequences with such elements result in smaller decreases in the reported expression ratio. Thus, in the probes selected for use in the methods and compositions of the present invention, preferably less than 60% of a probe's sequence overlaps with (i.e., is complementary to) repetitive elements such as simple nucleotide repeats or complex repetitive elements. More preferably, none (i.e., 0%) of a probe's sequence overlaps with repetitive sequence elements.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
   (a) identifying polynucleotide probes in the plurality of different polynucleotide probes that hybridize to the target polynucleotide with a sensitivity above a threshold sensitivity level;
   (b) ranking the identified polynucleotide probes according to the specificity with which each identified polynucleotide probe hybridizes to the target polynucleotide, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches; and
   (c) selecting one or more different polynucleotide probes from the ranked polynucleotide probes.

2. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
   (a) identifying polynucleotide probes in the plurality of different polynucleotide probes that hybridize to the target polynucleotide with a specificity above a threshold specificity level, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches;
   (b) ranking the identified polynucleotide probes according to the sensitivity with which each identified polynucleotide probe hybridizes to the target polynucleotide; and (c) selecting one or more different polynucleotide probes from the ranked polynucleotide probes.

3. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
(a) ranking the plurality of different polynucleotide probes according to the sensitivity with which each polynucleotide probe hybridizes to the target polynucleotide so that a sensitivity rank is obtained for each different polynucleotide probe;
(b) ranking the plurality of different polynucleotide probes according to the specificity with which each polynucleotide probe hybridizes to the target polynucleotide so that a specificity rank is obtained for each different polynucleotide probe, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches;
(c) obtaining a combined rank for each different polynucleotide probe, wherein the combined rank is determined by determining the sum of the sensitivity rank and the specificity rank for each different polynucleotide probe; and
(d) selecting one or more different polynucleotide probes from the plurality of different polynucleotide probes according to the combined rank of the different polynucleotide probes.

4. The method of claim 3 wherein the sum of the sensitivity rank and the specificity rank for each different polynucleotide probe is a weighted sum of the sensitivity rank and the specificity rank for each different polynucleotide probe.

5. The method of any one of claims 1–3 wherein the sensitivity with which a particular polynucleotide probe hybridizes to the target polynucleotide is represented by the binding energy with which the target polynucleotide hybridizes to the particular polynucleotide probe.

6. The method of claim 5 wherein the binding energy with which the target polynucleotide hybridizes to the particular polynucleotide probe is determined according to a nearest neighbor model.

7. The method of any one of claims 1–3 wherein the sensitivity with which a particular polynucleotide probe hybridizes to the target polynucleotide is represented by the level of hybridization of a target polynucleotide sequence to the particular polynucleotide probe.

8. The method of claim 7 wherein the level of hybridization of the target polynucleotide to the particular polynucleotide probe is calculated from the binding energy with which the target polynucleotide hybridizes to the particular polynucleotide probe.

9. The method of claim 8 wherein the binding energy with which the target polynucleotide hybridizes to the particular polynucleotide probe sequence is determined according to a nearest neighbor model.

10. The method of any one of claims 1–3 wherein the sensitivity of a particular polynucleotide probe is represented by the level of hybridization of a target polynucleotide to the particular polynucleotide probe, and wherein said level of hybridization is provided by a method comprising measuring the level of hybridization of the target polynucleotide to the particular polynucleotide probe.

11. The method of any one of claims 1–3, wherein the specificity of a particular probe is represented by said cross-hybridization score, and wherein the the cross-hybridization score is provided by a method which comprises selecting, from a plurality of binding energies, a binding energy that is the most negative binding energy in said plurality of binding energies,
wherein each binding energy in said plurality of binding energies is a binding energy for hybridization of the particular polynucleotide probe to a different polynucleotide, each different polynucleotide also differing from the target polynucleotide, and
wherein the selected binding energy is said cross-hybridization score of the particular polynucleotide probe.

12. The method of claim 11, wherein the binding energy for hybridization of the particular polynucleotide probe to each of the different polynucleotides is determined according to a nearest neighbor model.

13. The method of claim 11, wherein the different polynucleotides comprises polynucleotides expressed by a cell or organism of interest.

14. The method of claim 11, wherein the different polynucleotides consist of polynucleotides comprising sequences with a selected level of identity or homology to a complementary sequence of said particular polynucleotide probe.

15. The method of claim 14, wherein the sequences having the selected level of identity or homology to the complementary sequence of the probe are identified by means of a BLAST or PowerBLAST algorithm.

16. The method of claim 14, wherein the different polynucleotides consist of polynucleotides comprising sequences that are at least 50% identical to the complementary sequence of said particular polynucleotide probe.

17. The method of claim 14, wherein the different polynucleotides consist of polynucleotides comprising sequences that are at least 60% identical to the complementary sequence of said particular polynucleotide probe.

18. The method of claim 14, wherein the different polynucleotides consist of polynucleotides comprising sequences that are at least 70% identical to the complementary sequence of said particular polynucleotide probe.

19. The method of claim 14, wherein the different polynucleotides consist of polynucleotides comprising sequences that are at least 80% identical to the complementary sequence of said particular polynucleotide probe.

20. The method of claim 14, wherein the different polynucleotides consist of polynucleotides comprising sequences that are at least 90% identical to the complementary sequence of said particular polynucleotide probe.

21. The method of claim 14, wherein the different polynucleotides consist of polynucleotides comprising sequences that are at least 95% identical to the complementary sequence of said particular polynucleotide probe.

22. The method of claim 14, wherein the different polynucleotides consist of polynucleotides comprising sequences that are at least 99% identical to the complementary sequence of said particular polynucleotide probe.

23. The method of any one of claims 1–3, said method further comprising a step of rejecting polynucleotide probes comprising one or more sequences corresponding to a repetitive element or a simple repeat.

24. The method of any one of claims 1–3, said method further comprising a step of rejecting polynucleotide probes comprising one or more sequences corresponding to a polyX repeat.

25. The method of any one of claims 1–3, wherein each of the plurality of different polynucleotide probes is complementary to a sequence in a region of the target polynucleotide.

26. The method of claim 25, wherein said region of the target polynucleotide is within a selected distance from the 3'-end of the target polynucleotide.

27. The method of claim 25, wherein said region of the target polynucleotide is within a selected distance from the 5'-end of the target polynucleotide.

28. The method of any one of claims 1–3, further comprising a step of rejecting polynucleotide probes having a fraction of one or more particular nucleotide bases that is above a particular threshold.

29. The method of any one of claims 1–3, further comprising a step of rejecting polynucleotide probes having a fraction of one or more particular nucleotide bases that is below a particular threshold.

30. The method of claim 28, wherein said step of rejecting comprises rejecting polynucleotide probes having a fraction of guanine and cytosine bases above a particular threshold.

31. The method of any one of claims 1–3, further comprising a step of rejecting polynucleotide probes for which a particular mathematical combination of the fraction of two or more particular nucleotide bases present in the polynucleotide probe is above a particular threshold.

32. The method of claim 31 wherein said step of rejecting comprises rejecting polynucleotide probes for which the difference in the fraction of nucleotide bases present in the polynucleotide probe that are cytosine from the fraction of nucleotide bases present in the polynucleotide probe that are adenine is above a particular threshold.

33. The method of any one of claims 1–3, further comprising a step of rejecting polynucleotide probes for which a particular mathematical combination of the fraction of two or more particular nucleotide bases present in the polynucleotide probe is below a particular threshold.

34. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
    (a) hybridizing a reference polynucleotide sample comprising molecules of the target polynucleotide to the plurality of different polynucleotide probes under conditions such that the hybridization intensity of each different polynucleotide probe to the reference polynucleotide sample correlates with the sensitivity and specificity with which each different polynucleotide probe hybridizes to the target polynucleotide, wherein the specificity of a probe is represented by a ratio of target polynucleotide molecules to non-target polynucleotide molecules hybridized to said probe under a particular set of hybridization conditions, wherein said target polynucleotide molecules hybridize with said probe with perfect match, and wherein said non-target polynucleotide molecules hybridize with said probe with one or more mismatches; and
    (b) selecting polynucleotide probes in the plurality of different polynucleotide probes that have the highest hybridization intensity.

35. The method of claim 34 wherein the hybridization temperature is within 5° C. of the mean melting temperature of the plurality of different polynucleotide probes from the target polynucleotide.

36. The method of claim 35 wherein the hybridization temperature is within 2° C. of the mean melting temperature of the plurality of different polynucleotide probes from the target polynucleotide.

37. The method of claim 34 wherein the steps of hybridizing and selecting are iteratively repeated.

38. The method of claim 37 wherein the number of different polynucleotide probes selected is no more than 20.

39. The method of claim 38 wherein the number of different polynucleotide probes selected is no more than 10.

40. The method of claim 39 wherein the number of different polynucleotide probes selected is no more than 5.

41. The method of claim 40 wherein one polynucleotide probe is selected from the plurality of different polynucleotide probes.

42. The method of any one of claims 1–3 or 34 wherein the plurality of different polynucleotide probes comprises polynucleotide sequences between 15 and 500 bases in length.

43. The method of claim 42 wherein the polynucleotide sequences are between 20 and 100 bases in length.

44. The method of claim 43 wherein the polynucleotide sequences are between 40 and 60 bases in length.

45. A system for selecting one or more different polynucleotide probes from a plurality of different polynucleotide probes of different nucleotide sequence according to the sensitivity and specificity with which each polynucleotide probe hybridizes to a target polynucleotide, said system comprising:
    (a) a memory; and
    (b) a processor element interconnected with the memory, wherein the memory encodes one or more programs causing the processor to perform a method comprising
        (i) identifying polynucleotide probes in the plurality of different polynucleotide probes that hybridize to the target polynucleotide with a sensitivity above a threshold sensitivity level; and
        (ii) ranking the identified polynucleotide probes according to the specificity with which each identified polynucleotide probe hybridizes to the target polynucleotide, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches.

46. A system for selecting one or more different polynucleotide probes from a plurality of different polynucleotide probes of different nucleotide sequence according to the sensitivity and specificity with which each polynucleotide probe hybridizes to a target polynucleotide, said system comprising:
    (a) a memory; and
    (b) a processor element interconnected with the memory, wherein the memory encodes one or more programs causing the processor to perform a method comprising (i) identifying polynucleotide probes in the plurality of different polynucleotide probes that hybridize to the target polynucleotide sequence with a specificity above a threshold specificity level, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches; and (ii) ranking the identified polynucleotide probes according to the sensitivity with which each identified polynucleotide probe hybridizes to the target polynucleotide.

47. A system for selecting one or more different polynucleotide probes from a plurality of different polynucleotide probes of different nucleotide sequence according to the sensitivity and specificity with which each polynucleotide probe hybridizes to a target polynucleotide, said system comprising:

(a) a memory; and (b) a processor element interconnected with the memory, wherein the memory encodes one or more programs causing the processor to perform a method comprising (i) ranking the plurality of different polynucleotide probes according to the sensitivity with which each polynucleotide probe hybridizes to the target polynucleotide so that a sensitivity rank is obtained for each different polynucleotide probe;

(ii) ranking the plurality of different polynucleotide probes according to the specificity with which each polynucleotide probe hybridizes to the target polynucleotide so that a specificity rank is obtained for each different polynucleotide probe, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches; and (iii) obtaining a combined rank for each different polynucleotide probe, wherein the combined rank is determined by determining the sum of the sensitivity rank and the specificity rank for each different polynucleotide probe.

48. The system of claim 47 wherein the sum of the sensitivity rank and the specificity rank for each different polynucleotide probe is a weighted sum of the sensitivity rank and the specificity rank for each different polynucleotide probe.

49. The system of any one of claims 45–47 wherein the sensitivity with which a particular polynucleotide probe hybridizes to the target polynucleotide is represented by the binding energy with which said particular polynucleotide probe hybridizes to the target polynucleotide.

50. The system of claim 49 wherein the programs cause the binding energy with which the target polynucleotide hybridizes to the particular polynucleotide probe to be calculated according to a nearest neighbor model.

51. The system of any one of claims 45–47, wherein the specificity of a particular probe is represented by said cross-hybridization score, and wherein said programs further cause the processor to determine the cross-hybridization score by a method which comprises selecting, from a plurality of binding energies, a binding energy that is the most negative binding energy in said plurality of binding energies, wherein each binding energy in said plurality of binding energies is a binding energy for hybridization of the particular polynucleotide probe to a different polynucleotide, each different polynucleotide also differing from the target polynucleotide, and wherein the selected binding energy is said cross-hybridization score of the particular polynucleotide probe.

52. The system of claim 51 wherein said programs further cause the processor to perform steps of calculating the binding energies in said plurality of binding energies according to a nearest neighbor model.

53. The system of claim 51 wherein the different polynucleotides consist of polynucleotides comprising sequences with a selected level of identity or homology to a complementary sequence of said particular polynucleotide probe.

54. The system of claim 53 wherein said programs cause the processor to identify sequences having the selected level of identity or homology to a complementary sequence of said particular polynucleotide probe by means of a BLAST or PowerBLAST algorithm.

55. The system of any one of claims 45–47 wherein said programs further cause the processor to perform a step of rejecting polynucleotide probes comprising one or more sequences corresponding to a repetitive element or a simple repeat.

56. The system of any one of claims 45–47 wherein said programs further cause the processor to perform a step of rejecting polynucleotide probes comprising one or more sequences corresponding to a polyX repeat.

57. The system of any one of claims 45–47 wherein said programs further cause the processor to perform a step of selecting polynucleotide probes comprising a sequence that is complementary to a sequence within a particular distance from the 3'-end of the target polynucleotide.

58. The system of any one of claims 45–47 wherein said programs further cause the processor to perform a step of selecting polynucleotide probes comprising a sequence that is complementary to a sequence within a particular distance from the 5'-end of the target polynucleotide.

59. The system of any one of claims 45–47 wherein said programs further cause the processor to perform a step of rejecting polynucleotides probes having a fraction of one or more particular nucleotide bases that is above a particular threshold.

60. The system of any one of claims 45–47 wherein said programs further cause the processor to perform a step of rejecting polynucleotide probes having a fraction of one or more particular nucleotide bases that is below a particular threshold.

61. The system of any one of claims 45–47 wherein said programs further cause the processor to perform a step of rejecting polynucleotide probes for which a particular mathematical combination of the fraction of two or more particular nucleotide bases present in the polynucleotide probes is above a particular threshold.

62. The system of any one of claims 45–47 wherein said programs further cause the processor to perform a step of rejecting polynucleotide probes for which a particular mathematical combination of the fraction of two or more particular nucleotide bases present in the polynucleotide probes is below a particular threshold.

63. A computer program product for use in conjunction with a computer having a memory and a processor, the computer program product comprising a computer readable storage medium having a computer program mechanism encoded thereon, wherein said computer program mechanism may be loaded into the memory of a computer and cause a processor of the computer to execute the steps of:
  (a) identifying polynucleotide probes in a plurality of different polynucleotide probes of different nucleotide sequence that hybridize to a target polynucleotide with a sensitivity above a threshold level; and
  (b) ranking the identified polynucleotide probes according to the specificity with which each identified polynucleotide probe hybridizes to the target polynucleotide, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches.

64. A computer program product for use in conjunction with a computer having a memory and a processor, the computer program product comprising a computer readable storage medium having a computer program mechanism encoded thereon, wherein said computer program mechanism may be loaded into the memory of a computer and cause a processor of the computer to execute the steps of:
  (a) identifying polynucleotide probes in a plurality of different polynucleotide probes of different nucleotide sequence that hybridize to a target polynucleotide with a specificity above a threshold level, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches; and
  (b) ranking the identified polynucleotide probes according to the sensitivity with which each identified polynucleotide probe hybridizes to the target polynucleotide.

65. A computer program product for use in conjunction with a computer having a memory and a processor, the computer program product comprising a computer readable storage medium having a computer program mechanism encoded thereon, wherein said computer program mechanism may be loaded into the memory of a computer and cause a processor of the computer to execute the steps of:
  (a) ranking a plurality of different polynucleotide probes of different nucleotide sequence according to the sensitivity with which each polynucleotide probe hybridizes to a target polynucleotide so that a sensitivity rank is obtained for each different polynucleotide probe;
  (b) ranking the plurality of different polynucleotide probes according to the specificity with which each polynucleotide probe hybridizes to the target polynucleotide so that a specificity rank is obtained for each different polynucleotide probe, wherein the specificity of a probe is represented by a quantity selected from the group consisting of (i) a ratio of target polynucleotide molecules to non-target polynucleotide molecules hybridized to said probe under a particular set of hybridization conditions and (ii) a cross-hybridization score based on calculated binding energies of said probe to non-target polynucleotide molecules, wherein said target polynucleotide molecules hybridize with said probe with perfect match, and wherein said non-target polynucleotide molecules hybridize with said probe with one or more mismatches; and
  (c) obtaining a combined rank for each different polynucleotide probe, wherein the combined rank is determined by determining the sum of the sensitivity rank and the specificity rank for each different polynucleotide probe.

66. The computer program product of claim 65 wherein the sum of the sensitivity rank and the specificity rank for each different polynucleotide probe is a weighted sum of the sensitivity rank and the specificity rank for each different polynucleotide probe.

67. The computer program product of any one of claims 62–65 wherein the sensitivity with which a particular polynucleotide probe hybridizes to the target polynucleotide is represented by the binding energy with which said particular polynucleotide probe hybridizes to the target polynucleotide.

68. The computer program product of claim 67 wherein said computer program mechanism may be loaded into the memory and further cause the binding energy with which the target polynucleotide hybridizes to the particular polynucleotide probe to be calculated according to a nearest neighbor model.

69. The computer program product of any one of claim 63–65 wherein the specificity of a particular probe is represented by said cross-hybridization score, and wherein said computer program mechanism can be loaded into the memory and further cause the processor to determine the cross-hybridization score by a method which comprises selecting, from a plurality of binding energies, a binding energy that is the most negative binding energy in said plurality of binding energies,
  wherein each binding energy in said plurality of binding energies is a binding energy for hybridization of the particular polynucleotide probe to a different polynucleotide, each different polynucleotide also differing from the target polynucleotide, and
  wherein the selected binding energy is said cross-hybridization score of the particular polynucleotide probe.

70. The computer program product of claim 69 wherein said computer program mechanism can be loaded into the memory and further cause the processor to perform steps of calculating the binding energies in said plurality of binding energies according to a nearest neighbor model.

71. The computer program product of claim 69 wherein the different polynucleotides consist of polynucleotides comprising sequences with a selected level of identity or homology to a complementary sequence of said particular polynucleotide probe.

72. The computer program product of claim 71 wherein said computer program mechanism can be loaded into the memory and further cause the processor to identify sequences having the selected level of identity or homology to a complementary sequence of said particular polynucleotide probe by means of a BLAST or PowerBLAST algorithm.

73. The computer program product of any one of claims 63–65 wherein said computer program mechanism can be loaded into the memory and further cause the processor to perform a step of rejecting polynucleotide probes comprising one or more sequences corresponding to a repetitive element or a simple repeat.

74. The computer program product of any one of claims 63–65 wherein said computer program mechanism can be loaded into the memory and further cause the processor to perform a step of rejecting polynucleotide probes comprising one or more sequences corresponding to a polyX repeat.

75. The computer program product of any one of claims 63–65 wherein said computer program mechanism can be loaded into the memory and further cause the processor to perform a step of selecting polynucleotide probes comprising a sequence that is complementary to a sequence within a particular distance from the 3'-end of the target polynucleotide.

76. The computer program product of any one of claims 63–65 wherein said computer program mechanism can be loaded into the memory and further cause the processor to perform a step of selecting polynucleotide probes comprising a sequence that is complementary to a sequence within a particular distance from the 5'-end of the target polynucleotide.

77. The computer program product of any one of claims 63–65 wherein said computer program mechanism can be loaded into the memory and further cause the processor to perform a step of rejecting polynucleotides probes having a fraction of one or more particular nucleotide bases that is above a particular threshold.

78. The computer program product of any one of claims 63–65 wherein said computer program mechanism can be loaded into the memory and further cause the processor to perform a step of rejecting polynucleotide probes having a fraction of one or more particular nucleotide bases that is below a particular threshold.

79. The computer program product of any one of claims 63–65 wherein said computer program mechanism can be loaded into the memory and further cause the processor to perform a step of rejecting polynucleotide probes for which a particular mathematical combination of the fraction of two or more particular nucleotide bases present in the polynucleotide probes is above a particular threshold.

80. The computer program product of any one of claims 63–65 wherein said computer program mechanism can be loaded into the memory and further cause the processor to perform a step of rejecting polynucleotide probes for which a particular mathematical combination of the fraction of two or more particular nucleotide bases present in the polynucleotide probes is below a particular threshold.

81. The method of any one of claims 1–3, further comprising a step of rejecting polynucleotide probes having 100% sequence identity to a sequence that is not part of the sequence of said target polynucleotide.

82. The system of any one of claims 45–47, wherein said programs further cause the processor to perform a step of rejecting polynucleotide probes having 100% sequence identity to a sequence that is not part of the sequence of said target polynucleotide.

83. The computer program product of any one of claims 63–65, wherein said computer program mechanism can be loaded into the memory and further cause the processor to perform a step of rejecting polynucleotide probes having 100% sequence identity to a sequence that is not part of the sequence of said target polynucleotide.

84. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
  (a) identifying polynucleotide probes in the plurality of different polynucleotide probes that hybridize to the target polynucleotide with a sensitivity above a threshold sensitivity level;
  (b) ranking the identified polynucleotide probes according to the specificity with which each identified polynucleotide probe hybridizes to the target polynucleotide, wherein the specificity of a probe is represented by a ratio of target polynucleotide molecules to non-target polynucleotide molecules hybridized to said probe under a particular set of hybridization conditions, wherein said target polynucleotide molecules hybridize with said probe with perfect match, and wherein said non-target polynucleotide molecules hybridize with said probe with one or more mismatches, and wherein the ratio is calculated from quantities provided by a method that comprises:
    (i) determining the level of hybridization of the target polynucleotide to the particular polynucleotide probe; and
    (ii) determining the level of cross hybridization of non-target polynucleotides to the particular polynucleotide probe; and
  (c) selecting one or more different polynucleotide probes from the ranked polynucleotide probes.

85. A method for selecting one or more different polynucleotide probes from a plurality of different polynucleotide probes of different nucleotide sequence according to the sensitivity and specificity with which each different polynucleotide probe hybridizes to a target polynucleotide, said method comprising:
  (a) identifying polynucleotide probes in the plurality of different polynucleotide probes that hybridize to the target polynucleotide with a specificity above a threshold specificity level, wherein the specificity of a probe is represented by a ratio of target polynucleotide molecules to non-target polynucleotide molecules hybridized to said probe under a particular set of hybridization conditions, wherein said target polynucleotide molecules hybridize with said probe with perfect match, and wherein said non-target polynucleotide molecules hybridize with said probe with one or more mismatches, and wherein the ratio is calculated from quantities provided by a method that comprises:
    (i) determining the level of hybridization of the target polynucleotide to the particular polynucleotide probe; and
    (ii) determining the level of cross hybridization of non-target polynucleotides to the particular polynucleotide probe;

(b) ranking the identified polynucleotide probes according to the sensitivity with which each identified polynucleotide probe hybridizes to the target polynucleotide; and (c) selecting one or more different polynucleotide probes from the ranked polynucleotide probes.

86. A method for selecting one or more different polynucleotide probes from a plurality of different polynucleotide probes of different nucleotide sequence according to the sensitivity and specificity with which each different polynucleotide probe hybridizes to a target polynucleotide, said method comprising:

(a) ranking the plurality of different polynucleotide probes according to the sensitivity with which each polynucleotide probe hybridizes to the target polynucleotide so that a sensitivity rank is obtained for each different polynucleotide probe;

(b) ranking the plurality of different polynucleotide probes according to the specificity with which each polynucleotide probe hybridizes to the target polynucleotide so that a specificity rank is obtained for each different polynucleotide probe, wherein the specificity of a probe is represented by a ratio of target polynucleotide molecules to non-target polynucleotide molecules hybridized to said probe under a particular set of hybridization conditions, wherein said target polynucleotide molecules hybridize with said probe with perfect match, and wherein said non-target polynucleotide molecules hybridize with said probe with one or more mismatches, and wherein the ratio is calculated from quantities provided by a method that comprises:

(i) determining the level of hybridization of the target polynucleotide to the particular polynucleotide probe; and (ii) determining the level of cross hybridization of non-target polynucleotides to the particular polynucleotide probe;

(c) obtaining a combined rank for each different polynucleotide probe, wherein the combined rank is determined by determining the sum of the sensitivity rank and the specificity rank for each different polynucleotide probe; and (d) selecting one or more different polynucleotide probes from the plurality of different polynucleotide probes according to the combined rank of the different polynucleotide probes.

87. The method of claim 84, 85 or 86, wherein the level of hybridization of the target polynucleotide to the particular polynucleotide probe is calculated from the binding energy with which the target polynucleotide hybridizes to the particular polynucleotide probe.

88. The method of claim 84, 85 or 86 wherein the binding energy with which the target polynucleotide hybridizes to the particular polynucleotide probe is provided according to a nearest neighbor model.

89. The method of claim 84, 85 or 86, wherein the level of cross hybridization of non-target polynucleotides to the particular polynucleotide probe is calculated from the binding energies with which non-target polynucleotides cross-hybridize to the particular polynucleotide probe.

90. The method of claim 89 wherein the binding energies with which non-target polynucleotides cross-hybridize to the particular polynucleotide probe are determined according to a nearest neighbor model.

* * * * *